US010835304B2

(12) United States Patent
Shadduck

(10) Patent No.: US 10,835,304 B2
(45) Date of Patent: *Nov. 17, 2020

(54) MEDICAL ABLATION DEVICES AND METHODS

(71) Applicant: John H. Shadduck, Menlo Park, CA (US)

(72) Inventor: John H. Shadduck, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,500

(22) Filed: Apr. 6, 2020

(65) Prior Publication Data

US 2020/0229859 A1    Jul. 23, 2020

Related U.S. Application Data

(63) Continuation of application No. 16/407,010, filed on May 8, 2019, now Pat. No. 10,610,282.

(60) Provisional application No. 62/668,815, filed on May 9, 2018.

(51) Int. Cl.
*A61B 18/04* (2006.01)
*A61B 18/00* (2006.01)

(52) U.S. Cl.
CPC .... *A61B 18/04* (2013.01); *A61B 2018/00577* (2013.01); *A61B 2018/00589* (2013.01); *A61B 2018/046* (2013.01)

(58) Field of Classification Search
CPC .......... A61B 18/04; A61B 2018/00577; A61B 18/00321; A61B 2018/00434; A61B 2018/0047; A61B 2018/00589; A61B 2018/046; A61B 18/1477; A61B 18/1492; A61B 18/20; A61B 2018/00011; A61B 2018/00547; A61B 2018/00625; A61B 2018/00714; A61B 2018/00744; A61B 2018/00791; A61B 2018/00982; A61B 2018/044; A61B 2018/1425; A61B 2090/062; A61B 2090/064; A61B 2090/0807; A61B 2218/002

See application file for complete search history.

(56) References Cited

U.S. PATENT DOCUMENTS

| | | | |
|---|---|---|---|
| 10,610,282 | B2 | 4/2020 | Shadduck |
| 2003/0028189 | A1 | 2/2003 | Woloszko et al. |
| 2008/0132826 | A1 | 6/2008 | Shadduck et al. |
| 2012/0046656 | A1 | 2/2012 | Brannan |
| 2019/0343571 | A1 | 11/2019 | Shadduck |
| 2019/0365460 | A1 | 12/2019 | Shadduck |

*Primary Examiner* — Daniel W Fowler
*Assistant Examiner* — Tigist S Demie
(74) *Attorney, Agent, or Firm* — Levine Bagade Han LLP

(57) ABSTRACT

Ablation devices, more specifically needle injectors configured to deliver flowable thermal treatment media into an interface with tissue and that can provide a single dose of ablative energy.

16 Claims, 35 Drawing Sheets

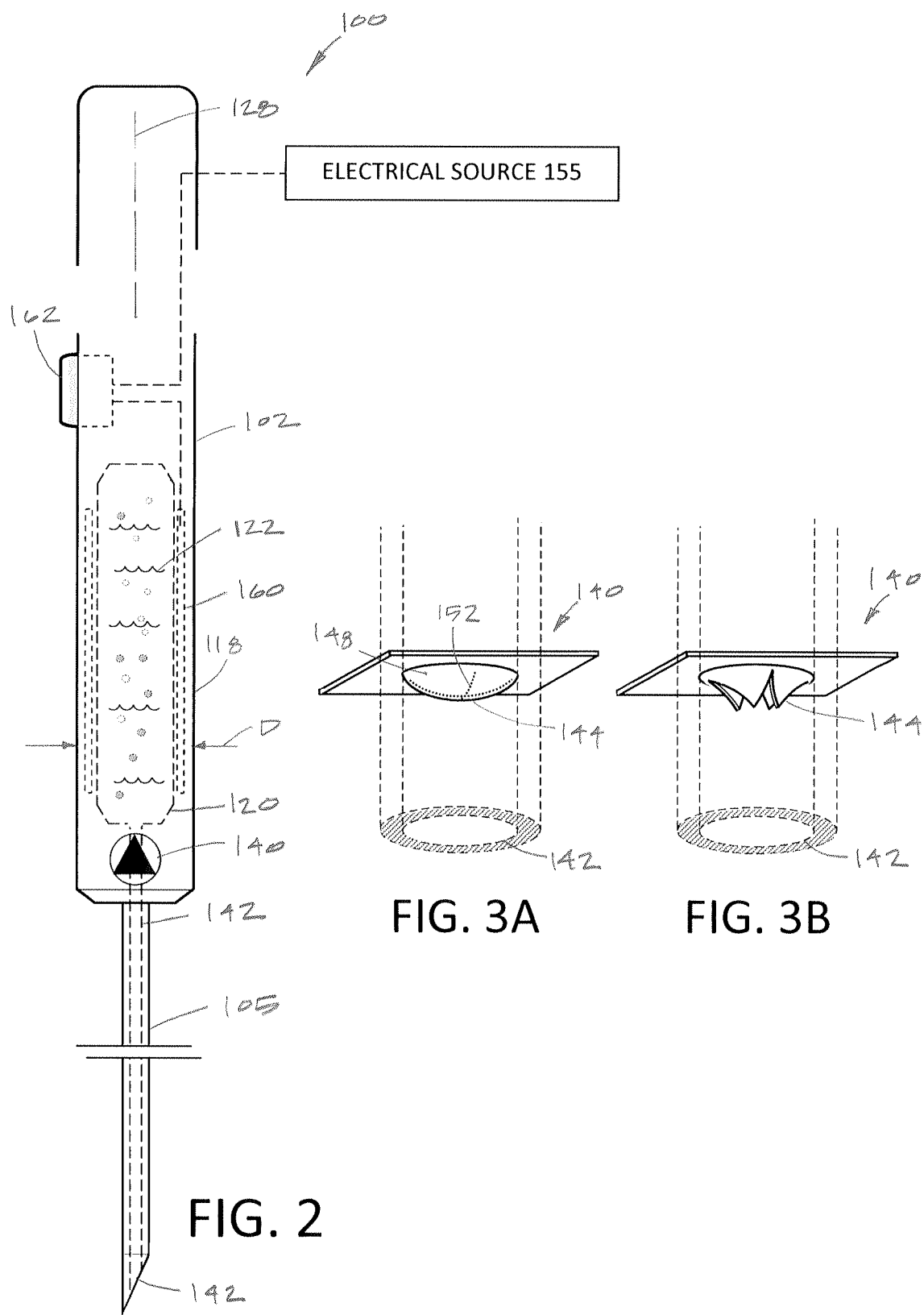

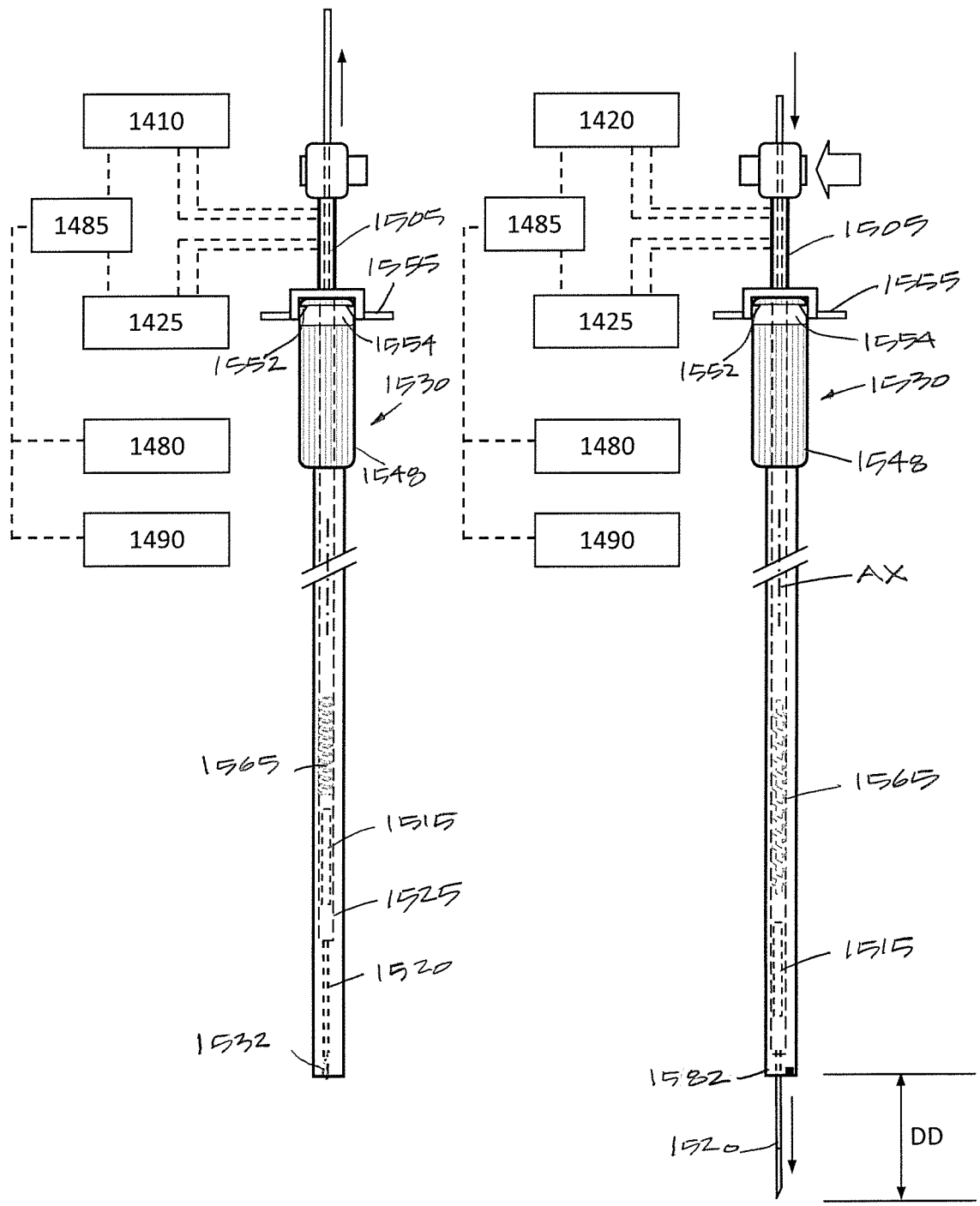

INTRODUCING AN ENDOSCOPE SHAFT WITH A DISTAL IMAGING SENSOR THROUGH A BODY LUMEN TO A SITE, WHEREIN THE INSERTION PROFILE OF THE ENDOSCOPE SHAFT IS LESS THAN 7 MM IN CROSS SECTION AND THE ENDOSCOPE SHAFT HAS A CHANNEL THEREIN WITH A CURVED DISTAL SECTION FOR DIRECTING A FLEXIBLE NEEDLE ADVANCED THERETHROUGH

INSERTING A INJECTOR INTO THE CHANNEL, THE INJECTOR HAVING AN INTERIOR CHAMBER COMMUNICATING WITH A FLOW OUTLET IN A NEEDLE MEMBER, THE INTERIOR CHAMBER CONTAINING A PRE-SELECTED VOLUME OF CONDUCTIVE LIQUID

OBSERVING THE SITE WITH THE IMAGING SENSOR AND ACTUATING THE INJECTOR TO ADVANCE THE NEEDLE MEMBER THROUGH THE CURVED CHANNEL AND THE LUMEN WALL INTO TARGETED TISSUE

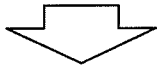

EJECTING SUBCRITICAL LIQUID FROM THE INTERIOR CHAMBER TO PROVIDE A SUBCRITICAL LIQUID FLOW THROUGH THE FLOW OUTLET AND COUPLING ELECTRICAL ENERGY TO SAID FLOW TO IONIZE THE FLOW WHEREIN THE IONIZED FLOW DELIVERS ABLATIVE ENERGY TO THE TARGETED TISSUE

FIG. 33

MEDICAL ABLATION DEVICES AND METHODS

CROSS-REFERENCE TO RELATED APPLICATION

This application is a continuation of U.S. patent application Ser. No. 16/407,010, filed May 8, 2019, which claims benefit of priority to U.S. provisional application No. 62/668,815 filed May 9, 2018, the entirety of each of which is incorporated by reference herein.

BACKGROUND OF THE INVENTION

1. Field of the Invention

This invention relates to tissue ablation devices, and more specifically relates to needle injectors that are configured to deliver flowable thermal treatment media into an interface with tissue and that can provide a single dose of ablative energy.

2. Description of the Background Art

Many types of ablation systems and devices have been developed for delivering thermal energy to tissue, including radiofrequency (RF) devices, laser devices, microwave devices, resistive heating devices and the like. Typically, such energy delivery systems are complex and require expensive generators and control systems.

What is needed for many ablation procedures is a system that can controllably deliver precise, limited amounts of energy to tissue for purposes of localized ablations, for example to ablate nerves, vascular malformations, tumors, warts, scar tissue, hypertrophic or hyperplastic tissue and the like.

SUMMARY OF THE INVENTION

The present invention relates to tissue ablation devices and related methods of use. Variations of the invention will now be described to provide an overall understanding of the principles of the form, function and methods of use of the systems disclosed herein. In general, the present invention provides devices or injectors that are configured to apply or inject a pre-set amount of ablative energy into tissue, typically interstitially but variations of this disclosure include energy delivery applied in any manner based on the application, including but not limited to an intraluminal treatment or a topical treatment. A variation of the devices described herein can comprise single-use devices. Some aspects of the devices (also referred to as "ablation sticks") includes (i) delivery of a selected total amount of energy over a selected brief time interval, and (ii) delivery of a selected energy dose at a predetermined rate, e.g., in calories/sec, over a multi-second interval. This description of the general principles of the invention is not to limit the inventive concepts in the appended claims. In addition, one application of the systems described herein includes ablation of tissue. However, in many cases the devices and methods can apply for coagulative, or therapeutic modes of energy delivery that do not result in ablation of tissue.

In one example, systems described herein include one or more single-use, inexpensive, disposable probes that have a rigid or flexible body extending to a distal needle portion wherein an interior chamber in the probe body contains subcritical water as a thermal flow media for treating tissue. The probe body includes a release mechanism allowing the thermal flow media to flow through the needle portion to interface with the targeted tissue. The probe or "ablation stick" can be connected to an energy source, such as a battery, which is configured to energize a heating mechanism in the probe body to provide subcritical water in the interior chamber.

In a first variation, a probe can be configured as a single-use disposable probe with a sealed interior chamber having a predetermined fluid volume configured to provide a predetermined energy dose. For example, in such a variation the interior chamber can have a volume ranging between 0.005 ml and 5.0 ml or more often between 0.010 ml and 2.0 ml. Variations of the devices can include the predetermined energy doses of at least 10 calories. Alternate variations can include the total energy dose is between 10 cal. and 1,000 cal.

In another aspect, a probe or ablation stick is configured for delivering a predetermined energy dose at a rate ranging between 1 cal/sec and 200 cal/sec, and often at a rate ranging between 5 cal/sec and 100 cal/sec.

Variations of the devices and methods include a heat transfer mechanism, which provides flow media in the interior chamber having a fluid pressure of at least 1.5 bar and often at least 2 bar or at least 5 bar. In some variations, such fluid pressure is at least 10 bar and the flow media can have a corresponding temperature of at least 110° C., and often at least 120° C. or at least 140° C.

The devices and methods can also include release mechanisms that release flow media from the interior chamber. Such mechanisms can include an instant release mechanism. Additional variations can include a single-use rupture disc or a magnetically-responsive pressure relief valve. Alternatively, or in combination, the release mechanism can comprise a valve adapted to pulse the release of thermal flow media.

In additional variations, the probe carries a needle that has an initial non-extended position and is ballistically extendable to an extended position by fluid pressure from the interior chamber.

Variations of the probes described herein can include a source for providing a thermal fluid media from a source that is less than 10 cm from an outflow aperture in the working end.

In additional embodiments, ablations sticks can be integrated into a system that includes (i) a flexible or rigid endoscope with a distal imaging sensor, wherein the endoscope is less than 6 mm in diameter and more often less than 5 mm in diameter, (ii) an articulating sleeve assembly that can be introduced through or integrated into the endoscope, and (iii) a kit of one or more flexible ablation sticks for the delivery of one or more preset energy doses. In this system embodiment, the endoscope can be navigated through a body lumen or passageway to reach a targeted site, and thereafter the articulating assembly can be manipulated to introduce a needle portion of the ablation stick at any angle into targeted tissue for a subsequent ablation.

An additional variation of a probe carries a fluid-filled chamber proximate to the needle assembly wherein an energy source coupled with fluid in the chamber can be explosively vaporized to ballistically move the needle assembly from a non-extended position to an extended position. Additionally, the energy source that is utilized to ballistically drive a needle assembly from a non-extended position to an extended position can be controlled to provide a plurality of selected energy delivery levels to thereby allow different rates of the needle acceleration to penetrate different needles in different tissues.

Additional advantages of the invention will be apparent from the following description, the accompanying drawings and the appended claims.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 2 is a schematic view of a device as in FIG. 1A-1B which includes a body portion having an interior chamber configured for containing subcritical water and a valve or release mechanism for releasing the subcritical water from the interior chamber into a flow passageway to provide a fluid flow through a distal aperture, and further illustrating an energy source for heating the contents of the interior chamber.

FIG. 3A is perspective view of a release mechanism for releasing the subcritical water from the interior chamber which comprising a rupture disc in an initial, non-ruptured configuration that seals the interior chamber.

FIG. 3B is a view of the rupture disc of FIG. 3A in a secondary, ruptured configuration for releasing subcritical water from the interior chamber.

FIGS. 20A-20C illustrate individual functional components and sterile packaging of a treatment kit corresponding to the invention wherein the key functional components at separate rather than integrated as described in previous variations, wherein FIG. 20A illustrates an elongated flexible endoscope component, FIG. 20B illustrates an elongated catheter with a distal articulating region for introducing through a working channel of the endoscope component of FIG. 20A, and FIG. 20C illustrates an elongated ablation probe with an extendable needle portion, wherein the probe adapted for introduction through the articulating catheter component of FIG. 20B.

FIGS. 21A-21C illustrates individual functional components of a treatment kit similar to that of FIGS. 20A-20C, wherein FIG. 21A illustrates an endoscope component that consists of a relatively short, rigid member rather than an elongated flexible member as in FIG. 20A, FIG. 21B depicts an articulating sleeve component, and FIG. 21C illustrates an ablation probe.

FIG. 30A is an illustration of the ablation stick of FIG. 28A latched to an endoscope with the needle member in a retracted, cocked position.

FIG. 30B is an illustration of the ablation stick and endoscope of FIG. 30A with the needle member in a released extended position.

FIG. 33 is a diagram showing the method of the invention relating to the use of the endoscope in the ablation stick of FIGS. 31A-32.

DESCRIPTION OF THE INVENTION

The present invention relates to energy delivery devices and related methods of use. Variations of the invention will now be described to provide an overall understanding of the principles of the form, function and methods of use of the devices disclosed herein. In general, the present invention provides single-use devices or injectors that are configured to apply or inject a pre-set amount of ablative energy into tissue, typically interstitially but alternatively the energy delivery can be an intraluminal treatment or a topical treatment. The single-use devices or ablation sticks can be designed (i) to deliver a selected total amount of energy over a selected interval, and (ii) to deliver a selected energy dose with a predetermined amount of energy per/second over a multi-second interval. This description of the general principles of this invention is not meant to limit the inventive concepts in the appended claims.

Figure 1A:
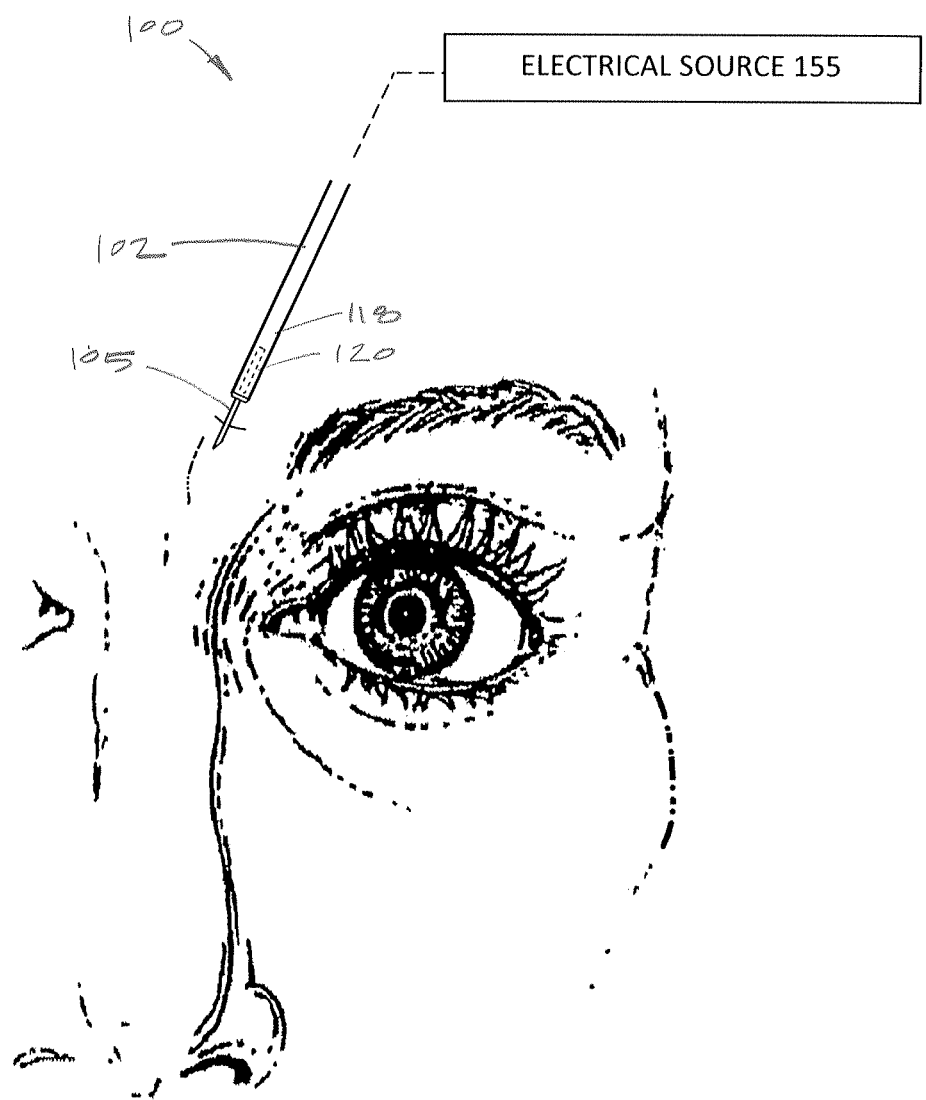
FIG. 1A is an illustration of a method of the invention for treating deep wrinkles in a patient's forehead by introducing a needle tip of a device into a targeted site and thereafter ejecting subcritical water from an interior chamber in the device to provide a flow through an aperture in the needle tip to ablate targeted nerves.
Figure 1B:
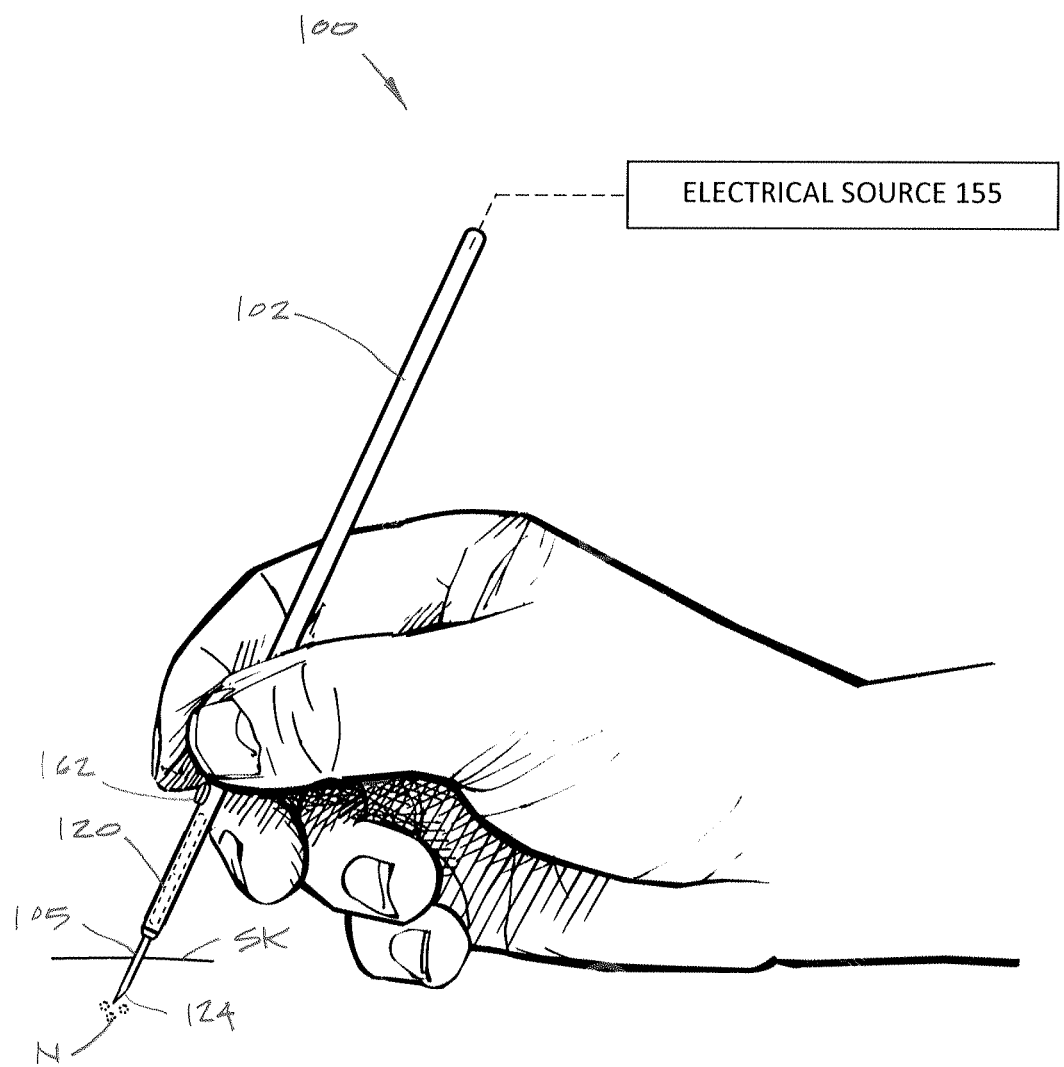
FIG. 1B is a schematic illustration of a method as in FIG. 1A wherein the device handle is shown and the needle tip is introduced into the site proximate targeted nerves.

FIGS. 1A, 1B and 2 are illustrations of a variation of an ablation system 100 that is adapted for the treatment of deep wrinkles. The system includes a handheld device with has a body portion 102 and a distal needle portion 105 that is introduced into at targeted site. A distal region 118 of the body portion 102 has an interior chamber 120 that carries subcritical water 122 that can be releases therefrom to flow through at least one aperture 124 in the needle portion 105 to interface with tissue and thereby ablate targeted nerves N underlying skin SK (see FIG. 1B). The ablation of nerves with the method corresponding invention to treat wrinkles is adapted to function similar to a Botox treatment. Such an ablation treatment as depicted in FIGS. 1A-1B ablates nerves to block signals from the nerves which can thereby weaken facial muscles in the skin of the forehead, thus easing the tension that causes wrinkles to form. The ablation treatment of the invention can be longer lasting than Botox and can be used for treatment of moderate-to-severe glabellar lines (frown lines between eyebrows) and other facial creases.

FIG. 2 is a schematic view of a single-use hand-held device 100 as in FIG. 1 which shows an elongated a body or handle portion 102 extending along axis 128 and is coupled to distal needle portion 105. The body portion 102 can have any suitable cross-section dimension D for gripping with a human hand and fingers or alternatively can be configured for coupling to a robotic system for controlled insertion of the needle portion 105 into a patient's body. The interior chamber 120 is configured to carry a pressurized heated fluid, which in one variation is heated, pressurized or subcritical sterile water 122. The device 100 also carries a subcritical water release mechanism 140 which can be a valve other type of release mechanism as described in more detail below. The release mechanism 140 provides a valve-closed configuration or seal to seal a flow passageway 142 extending from the interior chamber 120 through the needle portion 105 to the at least one outflow aperture 124. In a variation, the release mechanism 140 is a pressure relief valve as is known in the art which opens at a predetermined pressure within pressure ranges described in more detail below.

In a variation shown in FIGS. 3A-3B, the release mechanism 140 comprises a rupture disc 144 in flow passageway 142 which is a non-reclosing pressure relief mechanism or valve adapted for a single use, wherein the disc 144 in an initial form (FIG. 3A) ruptures at a selected pressure to provide a valve-open position (FIG. 3B) to thereby release subcritical water from the interior chamber 120. Thus, the rupture disc 144 of FIGS. 3A-3B is a sacrificial component or one-time-use membrane that fails at the selected fluid pressure in interior chamber 120. The disc 144 can be fabricated of a metal but other materials such as plastics and elastomers or layers of different materials can be used as alternatives. The rupture disc 144 provides an instant response which can occur in milliseconds to allow release of subcritical water from interior chamber 120. In FIG. 3A, it can be seen that a disc 144 has a dome region 148 facing distally that comprises a metal that is weakened by precision cuts or scores 152 in the material, for example by using lasers to etch the scores 152 to a precise depth in the material. The rupture of disc 144 about the scores 152 occurs when tensile forces exceed the ultimate tensile stress of the disc material as shown in FIG. 3B.

In a variation, referring again to FIG. 2, the interior chamber 120 has a very limited capacity, for example, from about one-half drop of water to 40 drops of water, or about 0.025 ml to 2 ml. More often, the interior chamber capacity is from about 1 drop of water to 20 drops of water (0.05 ml, to 1.0 ml). FIG. 2 further illustrates schematically that an electrical source 155 is coupled to a heating mechanism 160 configured to delivery energy to the interior chamber 120 to provide subcritical water 122 therein. In a variation, the device 100 with the interior chamber 120 is pre-packaged and sealed wherein the fluid pressure may be slightly higher than ambient pressure. After applying energy from heating mechanism 160, the fluid pressure of subcritical water 122 in chamber 120 is at least 1.5 bar, at least 2 bar or at least 5 bar. Often, the fluid pressure is at least 10 bar or at least 15 bar. As an example, the fluid pressure would be approximately 16 bar (232 psi) at 200° C. As a comparison, at room temperature, a common $CO_2$ canister used is some medical devices has an internal pressure of over 850 psi. Typically, the single-use devices 100 corresponding to the invention are provided with small capacity interior chambers 120 that are adapted for higher subcritical water pressures than devices with larger capacity interior chambers. The term subcritical water as used herein refers to water maintained in a liquid phase (typically held by pressure) at temperatures above the atmospheric boiling point (100° C.) and up to the critical temperature (374° C.) of water. As can be understood, subcritical water is stable in the interior chamber 120 because of the overpressure raises the boiling point. Variations of the devices and methods described herein can include various subcritical liquids and/or or solutions in addition to or in place of water.

It also can be understood that the amount of applied energy, for example measured in calories, required to ablate nerves to subdue muscle contraction as in FIGS. 1A-1B is exceedingly small. Further, the amount of energy carried in subcritical water is very high so that the total volume of subcritical water released from the interior chamber 120 to thereafter interface with tissue (FIGS. 1 and 3) can be less than one-half drop or less than one drop of subcritical water. The duration of treatment, that is, the time interval over which the subcritical water is interfaces with tissue after flow into at least one aperture 124 in needle portion 105 may be less than one-half second, or less than one second. Longer duration flows are described with other device variations and treatments below. The corresponding flow rate of subcritical water may be from 0.25 ml per minute to 2.5 ml per minute. All these variables are predetermined by the design of an individual device 100 (see FIG. 2) and the operating parameters of the heating mechanism 160 and energy applied thereto. More in particular, devices may be provided in a variety of configurations which are optimized for particular treatments. For example, a device 100 and the energy source 155 coupled to interior chamber 120 can be designed to provide (i) a predetermined number of calories delivered, (ii) a predetermined treatment interval, and/or (iii) a predetermined flow rate through the at least one aperture in the needle portion 105. In such a variation, the flow rate of subcritical water to the needle portion 105 can be predetermined by the dimensions of the flow passageway 142 extending away from the interior chamber 120 and the dimensions of at least one outflow aperture 124 in the needle portion 105 (see FIG. 2). It should be appreciated that there may be a single outflow aperture 124 the distal tip of the needle 105, or a plurality of outflow apertures around the distal tip of the needle 105 or microporosities in a microporous needle tip region.

In the variation shown in FIG. 2, the energy source 155 and heating mechanism 160 can comprise any suitable system configured for rapidly heating the fluid content of interior chamber 120 to provide subcritical water 122 with selected parameters therein. In FIG. 2, an actuation button 162 is provided to activate the heating mechanism 160. In a typical example, the heating mechanism 160 can comprise a resistive heating element that heats a wall around interior chamber 120 or a resistive electrical element that is immersed in fluid content of the interior chamber 120. In another variation, a coil coupled to an electrical source can be configured for inductively heating metallic walls of the interior chamber or inductive elements that interface with the fluid content of the interior chamber 120. In other variations, a laser or microwave mechanism may be used to heat the fluid content of the interior chamber.

Still referring to the schematic illustration of FIG. 2, the needle portion 105 typically comprises a needle shaft ranging in size from about 18 ga to 32 ga but may range up to 14 ga. The length of the needle portion 105 can range from about 2 mm to 20 mm or more for different applications, but typically may be 5 mm to 15 mm. The needle typically can be metal but polymeric needles also may be used and can be fabricated from a material such as PEEK. Ceramic microneedles are also known and can be used in the needle portion 105, or needles can be fabricated of a combination of a metal, polymer and/or ceramic. Often, a flexible polymeric needle may be used.

In one aspect of the invention, referring to FIG. 2, a device 100 is adapted to deliver a predetermined amount of energy dose to tissue, for example measured in total calories, and thus an inventory of energy delivery sticks can be provided which then allows for selection of a particular device for a particular procedure. In another aspect of the invention, a device 100 is adapted to deliver an energy dose at a predetermined rate, for example, in calories/second over a time interval. Such a predetermined rate of energy delivery is provided, in part, by selecting the dimensions of the flow channel in the needle portion 205 and the dimensions of outflow apertures in the needle portion. The rate of energy delivery is further controlled by the fluid pressure provided in the interior chamber, and the selected pressure at which the release mechanism releases the fluid. The rate of energy delivery through the 14 ga to 32 ga needles described above can range from about 1 cal/sec to 200 cal/sec, but typically would range between 5 cal/sec and 100 cal/sec.

In general, the predetermined energy dose is provided by a predetermined fluid capacity in the interior chamber 120 which in turn determines the amount of energy, or a range of energy, that may be delivered from such a single-use device 100. A single-use pre-packaged device 100 then can deliver a precise energy dose while eliminating the need for a control system or complex controller for controlling fluid flow rates from a pump, fluid pressure, constant or varied applied energy over a time interval, etc. It can be understood that the energy capable of being delivered can be calculated based on the fluid capacity in combination with the temperature of the subcritical water when released to flow through an aperture 124. Thus, for example, a physician with experience will become knowledgeable about the amount of applied energy that is optimal to achieve a particular ablation treatment, for example to ablate nerves, keloids, warts, skin lesions, sweat glands, hyperplastic or hypertrophic tissue, hemorrhoids, etc., and then a particular single-use device 100 can be selected which has the appropriate energy delivery capacity, or alternatively a plurality of devices can be used wherein each device has an energy capacity that can be additive in the treatment.

In one aspect, it is important to provide single-use devices 100 such as in FIGS. 2-3 that are configured with an interior chamber 120 with a predetermined fluid capacity that is quite limited, for example, less than 2 ml, less than 1 ml or less than 0.5 ml. As described above, the interior chamber 120 (FIG. 2) can be under a relatively high pressure so that there will be a possibility that the chamber 120 could rupture and release the pressurized fluid, which could have adverse effects on a patient or the physician. However, by design, the volume of subcritical water is very small so that the rupture of an interior chamber 120 that carries only a limited number of drops of subcritical water will not be catastrophic, while at the same the volume can carry enough for energy for many treatments.

In general, a method of ablating tissue corresponding to the invention comprises introducing an injector working end with at least one outflow aperture into a targeted site in an interior of a patient's body and ejecting subcritical water from an interior chamber in the injector to provide a flow through the at least one outflow aperture to interface with tissue in the site thereby delivering a dose of ablative energy to the tissue. In this method, the volume of the interior chamber is configured to provide a predetermined energy dose, which is greater than 10 calories. In variations of the single-use device, the deliverable energy dose can be between 10 calories and 1000 calories, and more often between 10 calories and 500 calories. In some variations, the energy dose can be between 10 calories and 250 calories. In this method of the invention, the subcritical water in the interior chamber has a volume ranging between 0.005 ml and 5.0 ml or more often between 0.010 ml and 2.0 ml. Further, in this method, the subcritical water has a temperature of at least 110° C., or at least 120° C. or at least 140° C.

In another aspect of the invention, the source of thermal fluid media or subcritical water is within close proximity to the needle portion and outflow aperture therein, which allows for little or no change in the temperature of the fluid media after release from the source or interior chamber until the flow reaches one or more outflow apertures. For example, in some embodiments, the source of fluid media is less 10 cm from an outflow aperture, and often the source is less than 5 cm from an outflow aperture. In general, a system corresponding to the invention for ablating tissue in a medical treatment comprises providing a probe having a working end adapted for introduction into a patient's body, a source carried by the probe adapted for providing a thermal fluid media capable of ablating tissue wherein said source is less than 10 cm an outflow aperture in the working end, or the source is less than 5 cm from such an outflow aperture. In this variation, a valve mechanism again is carried distally of the fluid media source to control fluid flow to the outflow aperture in the working end. In this variation, the fluid media source again has a fluid volume ranging between 0.005 ml and 5 ml and the system includes a heating mechanism operatively coupled to the source.

Figures 4A, 4B, 4C:
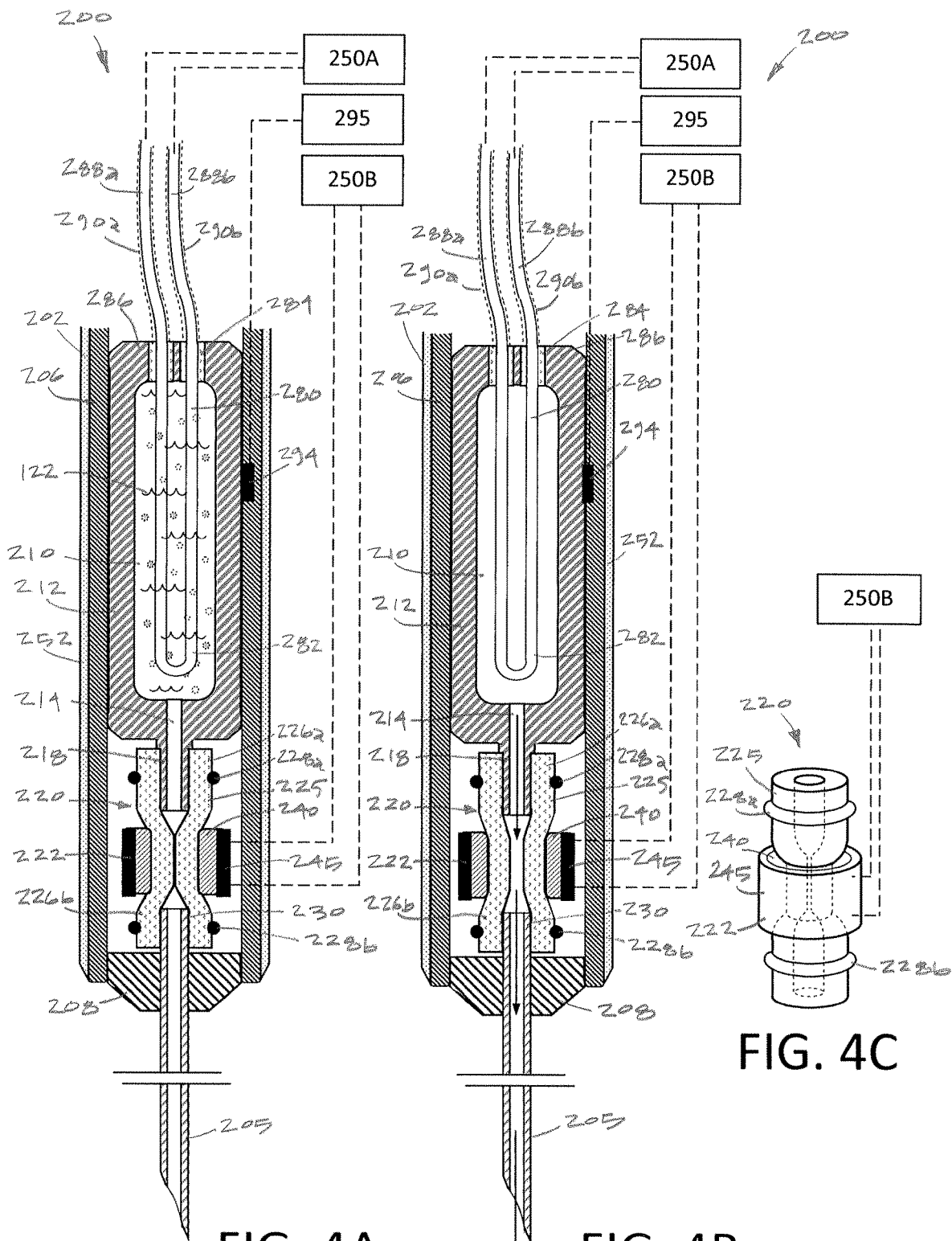
FIG. 4A is a sectional view another variation of a device similar to that FIG. 2 in a first configuration which includes a body portion having a cartridge with an interior chamber configured for containing subcritical water, a release mechanism for releasing the subcritical water from the interior chamber wherein the release mechanism comprises a squeeze valve shown in a valve-closed position that can be actuated to open by application of energy from an electrical source and further illustrating a resistive heating mechanism for heating the fluid contents of the interior chamber.
FIG. 4B is a sectional view of device of FIG. 4A in a second configuration wherein the squeeze valve is shown in a valve-open position.
FIG. 4C is a perspective view of the squeeze valve of FIGS. 4A-4B separated from the device body.

Now turning to FIGS. 4A-4C, a more detailed variation of a device 200 is shown that has an elongate device body 202 with needle portion 205 extending therefrom. The device body 202 comprises a stainless steel or polymer sleeve 206 with endcap 208 fixed thereto. Needle member 205 is fixed to and extends distally from endcap 208. In this variation, the interior chamber 210 is within a cartridge 212 carried in the device body 202. The cartridge 212 is configured to contain the subcritical water 122 in interior chamber 210 with an outlet 214 in a neck 218 of the cartridge 212. The cartridge 212 can be fabricated of a suitable metal such as stainless steel or can be a plastic material.

In the variation of FIGS. 4A-4C, the valve mechanism or subcritical water release mechanism comprises a form of squeeze valve 220 that comprises a compression-release collar 222 that squeezes a resilient elastomeric tubing 225 to provide a valve-closed position as shown in FIG. 4A. The compression-release collar 222 can be actuated to relax compression on the resilient tubing 225 to provide a valve-open position as shown in FIG. 4B. Thus, the valve 220 is a single-use valve that has an initial valve-closed position (FIG. 4A) and is openable one time to the valve-open position (FIG. 4B).

FIG. 4C shows a perspective view of the squeeze valve 220 separated from the assembly of FIGS. 4A and 4B. The elastomeric tubing 225 can be a biocompatible tubing such as silicone that has sufficiently strong walls to contain the above-described fluid pressures in the interior chamber 210 and can be compressed to provide the valve-closed position of FIG. 4A. The proximal end 226a of the elastomeric tubing 225 is fixed to the neck 218 of the cartridge by adhesives and/or mechanical clamps, for example, ring-clamp 228a (FIG. 4A). The distal end 226b of elastomeric tubing 225 is fixed to the proximal end 230 of the needle portion 205 by adhesives and/or mechanical clamps, for example, ring-clamp 228b (FIG. 4A).

The compression-release collar 222 can be any of several types of one-time use collars that can be expandable, meltable, frangible, sacrificial or the like and that can be actuated typically by energy delivery to release compression on the elastomeric tubing 225. In one variation, the collar 222 can consist of a shape memory alloy core 240 surrounded by a resistive heating element 245. The NiTi core 240 which can have a "temporary" contracted configuration as in FIG. 4A wherein energy can be applied to the NiTi to heat the collar beyond a transition temperature to be altered from its temporary configuration to an expanded "memory" configuration to thereby provide the valve-open position of FIG. 4B. Shape memory alloy or NiTi actuators are well known in the art, and using similar principles are known of in the form of valves, pin-pullers, pin-pushers, and frangibolts (see, e.g., http://wwwainiaerospace.com/products.html). The NiTi is actuated from it temporary shape to its memory shape by heating, which can be heat migrating from the subcritical fluid 122 which is heated by a heating mechanism coupled to electrical source 250A. Alternatively, as shown in FIGS. 4A-4C, the resistive heating element 245 that surrounds the NiTi core 240 is connected to an electrical source 250B, which can be the same as electrical source 250A when used with a controller configured to control energy delivery for the two different functions. Each of the electrical sources 250A and 250B can consist of batteries to provide system portability. The resistive heating element 245 can consist of a resistive coil, a conductive polymer or a PTCR material (positive temperature coefficient of resistance) as is known in the art of such heating elements.

In other variations, the compression-release collar 222 can comprise (i) a collar of a shape memory polymer actuated by heating to move from a temporary shape to a memory shape, (ii) a collar with a discontinuity therein that has a sacrificial weld across the discontinuity of a fusible conductive polymer that will burn up upon energy delivery or (iii) a polymer collar that is meltable upon heat delivery to release compression on the tubing 225. In another variation, a handle of the device can have a moveable grip or lever actuator that can be used to mechanically release the collar. In another variation, a simple pressure relief valve can be used that opens at a predetermined pressure.

It should further be appreciated that the device body 202 and needle portion 250 can be covered with thermally insulative materials. FIGS. 4A-4B show insulator layer 252 surrounding the device body 202 which can be any suitable thickness. In particular, the needle portion 250 can have a thin ceramic coating (not shown) which can assist in preventing heat transmission through the shaft of the needle portion. Further, the interior chamber 210 and the flow passageway extending from the interior chamber through the needle portion 205 can have a thermally insulative coating, such as a ceramic to limit heat transfer from the fluid to the device body 202 and the body of the needle portion.

4A-4B, the heating mechanism for providing the subcritical water 122 comprises a resistive wire 280 that extends in a loop portion 282 through the interior chamber 210 and the liquid content of the chamber. The wire loop portion 282 can be a NiChrome wire or a similar material known in the art. The wire 280 passes through insulator sleeves 284 in the wall 286 of the cartridge 212 in the case in which the cartridge body is fabricated of a metal rather than a plastic. The electrical leads 288a and 288b extend from the loop portion 282 to the electrical source 250A which can be a battery or other electrical source. Each of the electrical leads 288a and 288b has an outer insulator layer shown in phantom view at 290a and 290b. While the resistive wire is shown with a loop portion 282 in FIGS. 4A and 4B, it should be appreciated that the resistive wire in interior chamber 210 can be coiled, looped or otherwise bent and packed to occupy a substantial space within the interior chamber 210 to maximize the surface area of the wire relative to the fluid volume to provide practically instant heat transfer to provide subcritical water. Other forms of heat transfer elements besides wires also can be used such as reticulated metal structures that carry the subcritical water in the pores or passageways therein.

Alternatively, a plurality of resistive rods or balls functioning as heat transfer elements can be packed in interior chamber 210 and configured for electrical or inductive heating to provide increased surface area of the heated elements for effective heat transfer.

FIGS. 4A-4B further show that the device 200 includes a temperature sensor 294 that is positioned in the device body 205 proximate the cartridge 212 to thereby determine the temperature of subcritical water in chamber 210 and to provide a signal of the temperature to a controller 295 or to a display (not shown).

In use, for example to treat nerves as in FIGS. 1A-1B in which limited ablation energy is required, the physician can first determine the amount of energy desired for the treatment as described above. Then, the physician can select a device 200, for example of the type shown in FIGS. 2-4A, that has an appropriate range of ablation capacity that brackets the targeted energy requirement. The ablation capacity of each device 200 is determined by the volume of subcritical water 122 that is released from an interior chamber to flow to an aperture in the needle portion 210 (see FIG. 4B) and the temperature of the subcritical water. It should be appreciated that the amount of subcritical water released from chamber 210 to interface with tissue (and the corresponding ablation capacity) will be less than the total capacity of the interior chamber. That is, the subcritical water is released under the interior fluid pressure of chamber 210 and when pressure inside the chamber is equalized with external pressure, then the flow will terminate. In use, the physician can optionally program a controller 295 to modulate the heating mechanism 250A after observation of signals from the temperature sensor 294. In one variation, the controller 295 may be configured actuate the release valve 222 in response to a signal from temperature sensor 294 that a targeted temperature has been achieved, for example a selected temperature between about 105° C. and 300° C.

Figure 5:
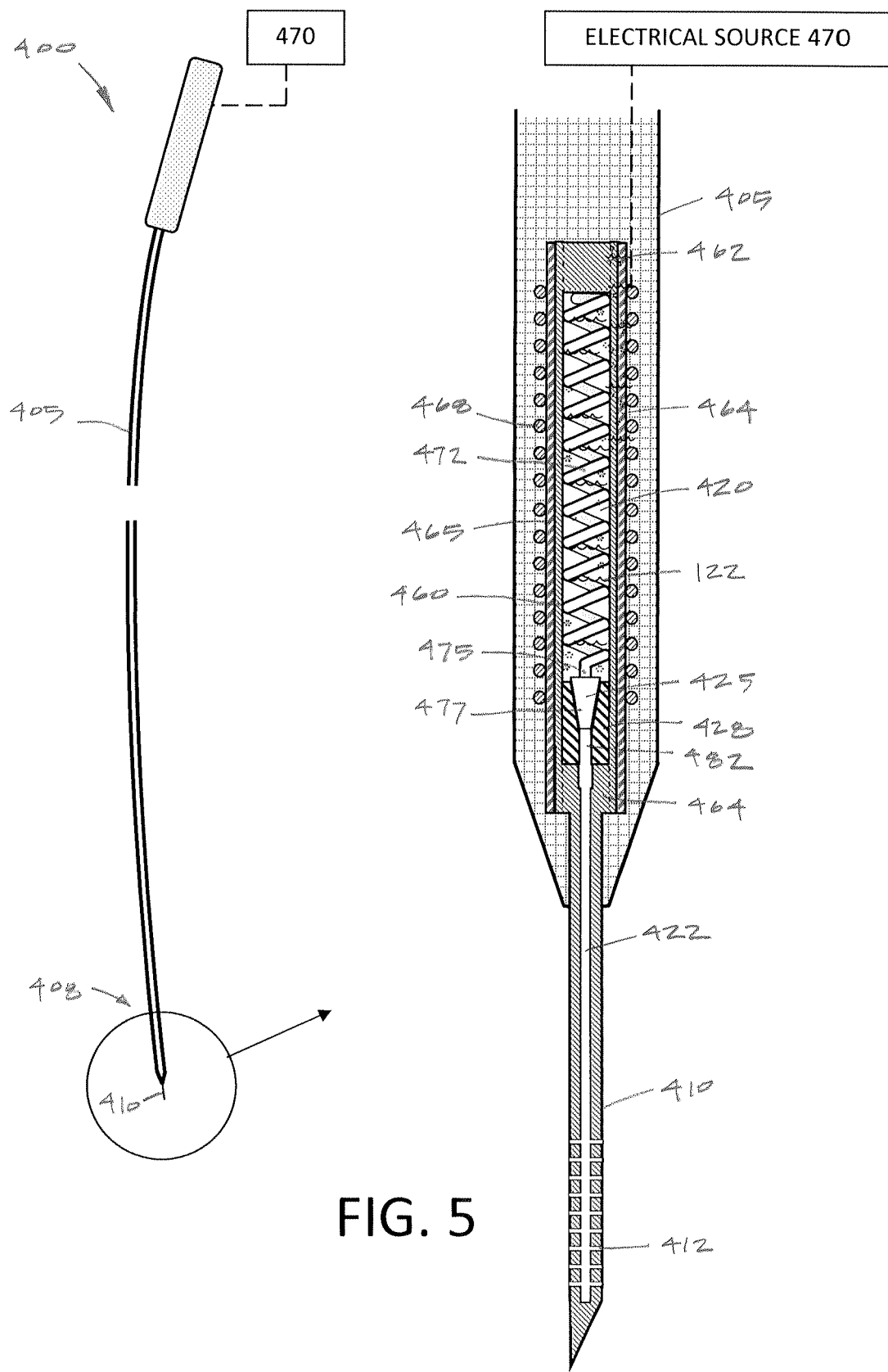
FIG. 5 is another variation of a probe similar to that of FIGS. 4A-4B, with a sectional view of an interior chamber configured for containing subcritical water, a shape memory alloy valve mechanism for releasing subcritical water from the interior chamber and an inductive heating mechanism for providing subcritical water.
Figures 6A, 6B:
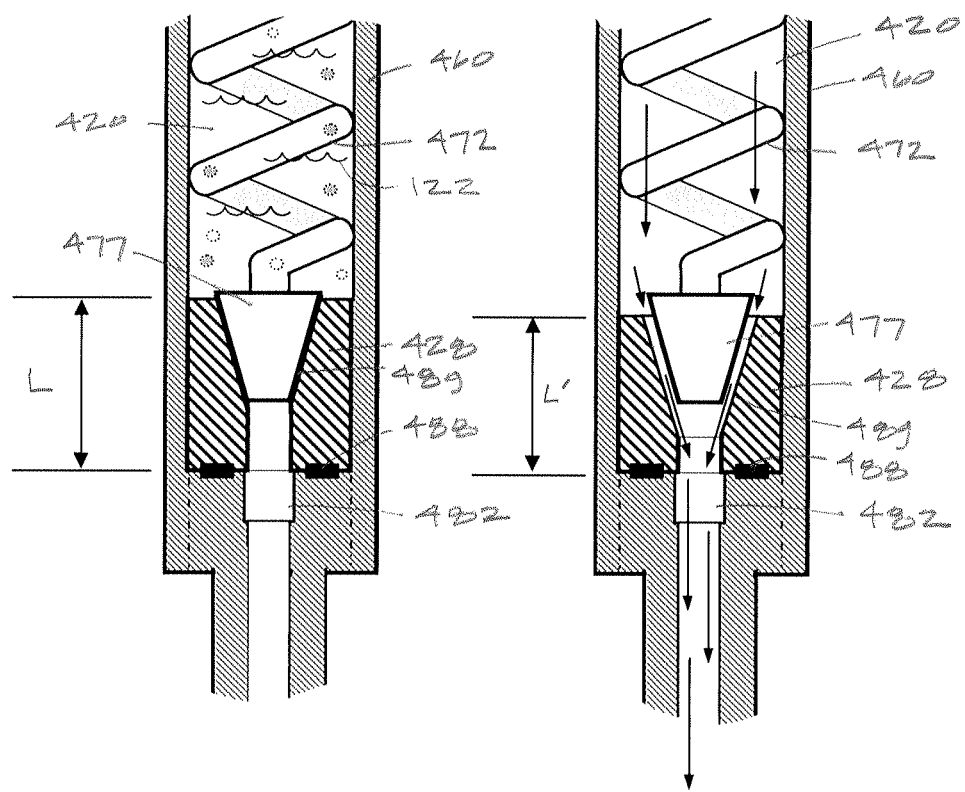
FIG. 6A is an enlarged sectional view of the valve mechanism of FIG. 5 in a valve-closed position.
FIG. 6B is a sectional view of the valve mechanism of FIG. 6A in a valve-open position.

Now turning to FIGS. 5 and 6A-6B, another variation of device 400 is shown that comprises an elongated flexible catheter body 405 that has a distal end portion 408 that carries a needle portion 410 with outflow ports or apertures 412 in a working end 415 thereof. An interior chamber 420 communicates though flow channel 422 with the needle portion 410 which is similar to the previous embodiment. Again, the capacity of the interior chamber 420 can be small and can contain from less than one drop to about 10 drops of subcritical water 122 when ready for use in ablating tissue. In this variation, the release mechanism for releasing the subcritical water from interior chamber 420 comprises a single-use valve or fluid release mechanism 425 that has an actuatable shape memory alloy (SMA) valve seat 428 described in more detail below, however, any suitable type of valve known in the art that is capable of containing the fluid pressures described above can be used.

Figure 7:
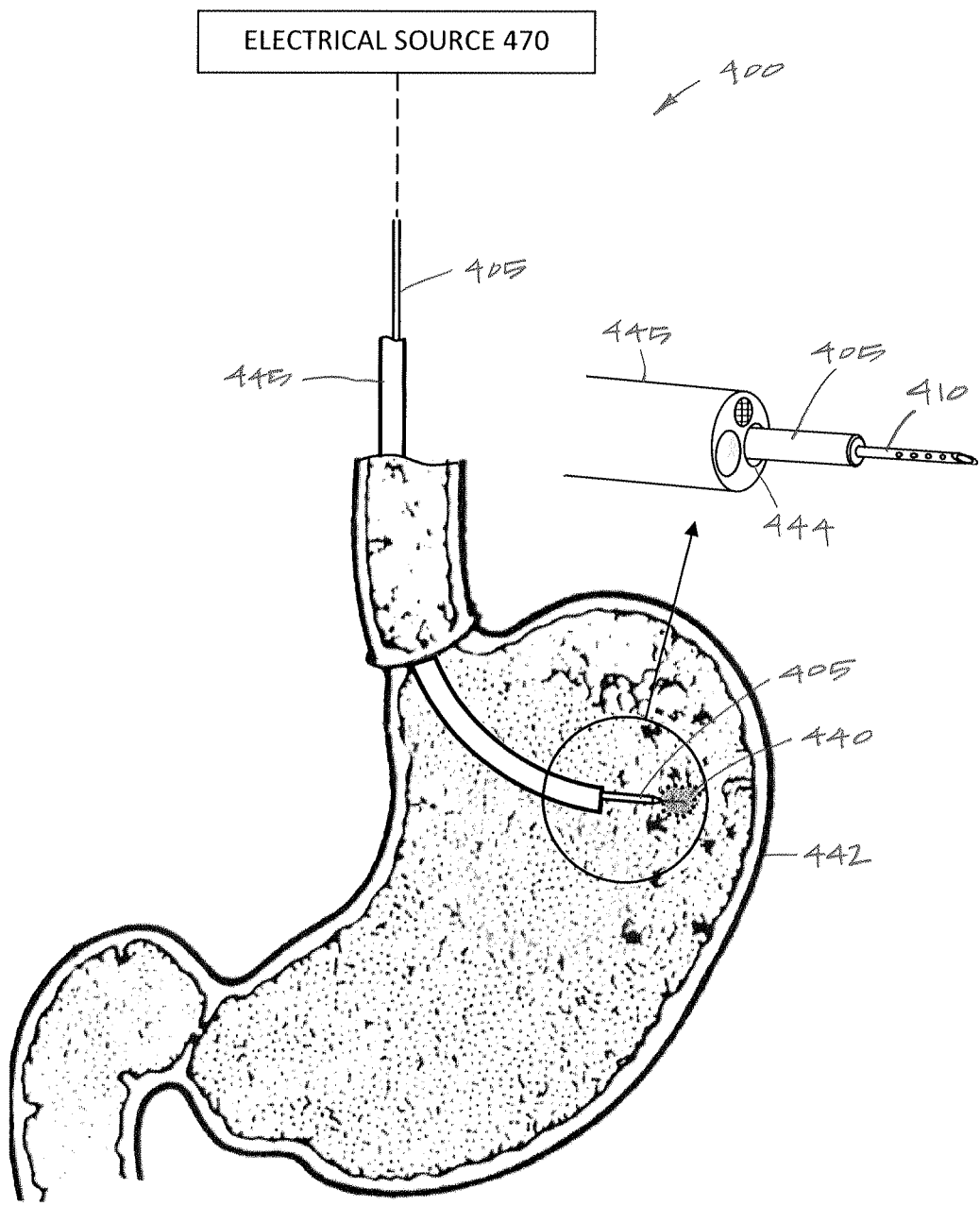
FIG. 7 is a schematic cut-away view of a method of using the probe of FIG. 5 to ablate abnormal tissue in a patient's stomach wall.

As can be seen in FIGS. 5 and 7, the device has a flexible catheter body 405 that can have any suitable length for reaching a targeted site a patient's body, typically by navigation through a body lumen or body cavity. FIG. 7 illustrates an exemplary ablation of a targeted site 440, such as an ulcer, lesion or tumor in a stomach 442 with the device 400 of FIG. 5. It should be appreciated that a catheter device 400 as in FIG. 5 can be navigated through any body lumen or passageway to treat tissue, such as an esophagus, a stomach, an intestine, a nasal passageway, a cervical canal, an airway or a passageway in a lung, a urethra, a ureter, bladder or the like. Typically, the catheter body 405 as depicted in FIG. 7 is introduced through the working channel 444 of an endoscope 445 or adjacent to an endoscopic viewing mechanism. In FIG. 7, an articulating endoscope or gastroscope 445 has been introduced through the esophagus 448 into the patient's stomach 442. The articulating endoscope 445 is manipulated to view the targeted tissue 440 and thereafter the catheter body 405 is introduced through the working channel 444 of the endoscope 445 to interface with the targeted tissue 440. With the endoscope 445 in the correct position, the physician then can advance the needle portion 410 of the device 400 into the target 440. Thereafter, the valve mechanism is opened to release the subcritical water to ablate the targeted tissue 440. As described previously, the dimensions of the targeted tissue 440 can be evaluated in advance and the physician can select a device 400 that has a preselected ablation capacity to match the ablation requirements.

Now turning back to FIG. 5, the sectional view of the distal end portion 408 of the catheter body 405 illustrates the heating mechanism and valve or subcritical water release mechanism 425. In this variation, the flexible catheter body 405 can comprise any polymer extrusion that is known in the art of fabricating catheters. The interior chamber 420 can comprise the bore of a rigid stainless steel hypotube 460 with a proximal end cap 462 welded therein and a distal endcap 464 which is connected to needle portion 410. The hypotube 460 is surrounded by an insulator or dielectric layer 465, which can be a polymer or ceramic. Again, the fluid capacity of the of interior chamber 420 is limited, for example, less than 20 drops or less than 10 drops. In other variations described below, the interior chamber 420 can be carried in an articulating or bendable slotted metal hypotube with a flexible polymer liner (see FIG. 9).

As can be seen in FIG. 5, the heating mechanism in the device 400 comprises an inductive heating coil 468 coupled to electrical source 470. The inductive coil 468 extends helically around the hypotube 450 and is adapted to inductively heat the hypotube 450 together with a heat transfer element 472 that can be inductively heated in the interior chamber 420. Thus, in this variation, the subcritical water in interior chamber 420 can be provided by heat transfer from either or both of the wall 474 of hypotube 460 around the interior chamber 420 and at least one heat transfer element 472 in the interior chamber 420.

In the embodiment of FIG. 5, the heat transfer element 472 is also a component of the valve or subcritical water release mechanism. As shown in the sectional view of FIGS. 5 and 6A-6B, the distal end 475 of heat transfer element 472 is linear with a tapered valve end 477 that extends into the shape memory alloy (SMA) valve seat 428 that has passageway 482 extending therethrough. FIGS. 6A-6B illustrate only the hypotube 450 and valve mechanism of the variation of FIG. 5 without the heating mechanism or catheter body. The SMA valve seat 428 is fixed in distal endcap 464 by welds 488. FIG. 6A shows the SMA valve seat 428 has a first valve-closed shape in which the SMA valve seat 428 has a temporary extended length L so that tapered valve end 477 extends into seat surface 489 of valve seat 480 to thereby close off the interior chamber 420. FIG. 6B shows the SMA valve seat 428 can be transitioned to a second valve-open or memory shape with length L' in which the valve seat 428 moves so that the valve seat surface 489 is away from the tapered valve end 477 to thereby open the interior chamber 420 to allow a flow of subcritical water 122 through passageway 482 to the needle portion 410. The SMA valve seat 428 is configured for transition from the elongated shape of FIG. 6A to the shortened shape of FIG. 6B by heat transfer from the subcritical water 122 while still contained in the interior chamber 420. Thus, the heating mechanism has dual functions, that is, first to heat the contents of the interior chamber to provide subcritical water 122 which then in turn actuates the SMA valve seat 428 to thus the valve to release the subcritical water as shown in FIGS. 6B and 8.

In a typical TiNi alloy, the transition temperature may be 30° C. to 40° C. but other shape memory alloys can have higher temperatures for thermal hysteresis and are useful for the valve mechanism described above, such as a ternary NiTiNb alloy that includes Niobium which can increase the transition temperature to 120° C. or more.

The shape memory alloy valve mechanism in FIGS. 5 and 6A-6B shows a valve seat 428 that can be transitioned between a temporary shape and a memory shape to close and open a valve, but it should be appreciates that the element carrying tapered valve end 477 also (or alternatively) can comprise a shape memory material which can transition to a memory shape to open the valve mechanism.

Figure 8:
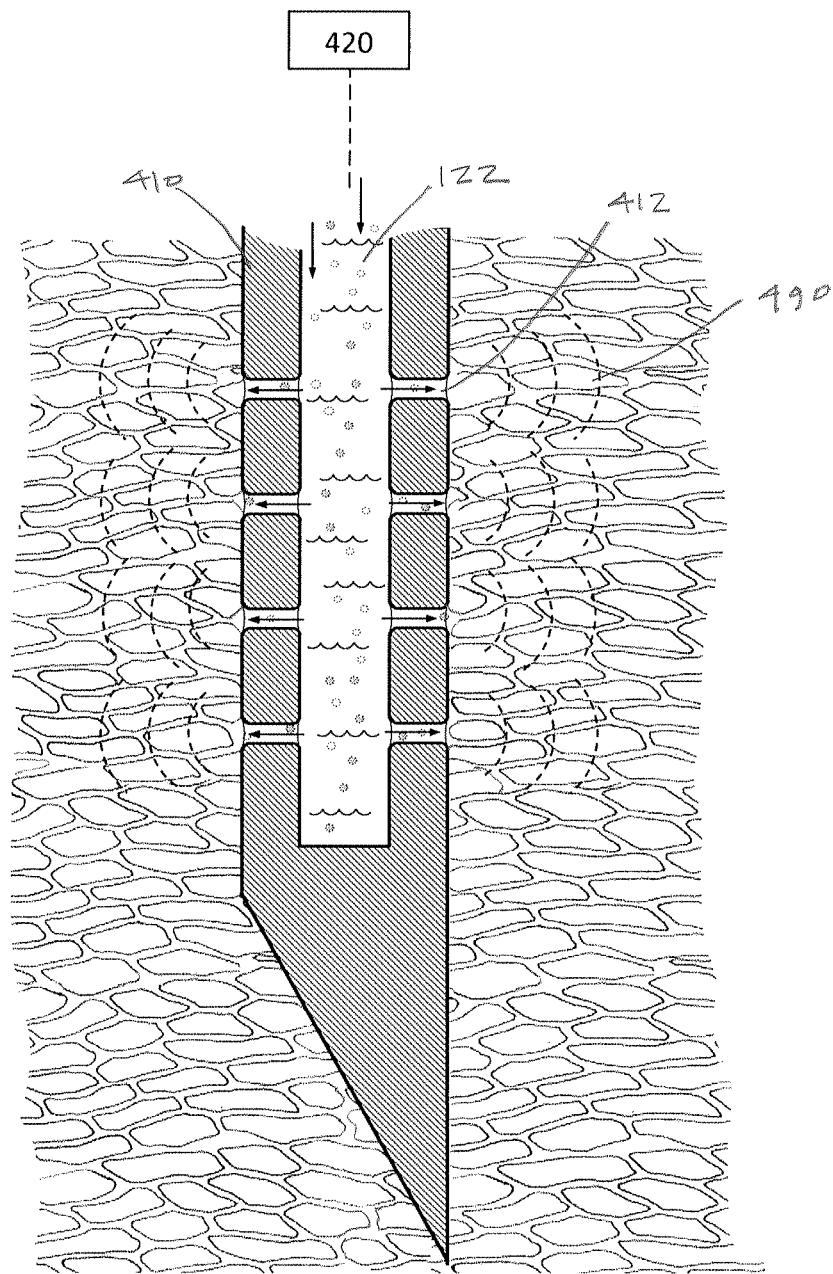
FIG. 8 is a sectional schematic view of the needle portion of the probe of FIG. 5 illustrating the release of subcritical water from an interior chamber to provide a flow into and through a flow passageway and apertures to interface with tissue.

FIG. 8 schematically illustrates the flow of subcritical water 122 from interior chamber through passageway 482 to outflow apertures 412 in the needle portion 410 which interfaces with tissue 490. In general, a method as shown schematically in FIGS. 7 and 8 comprises introducing the working end of an energy delivery device of FIG. 5 into a targeted site in an interior of a patient's body and providing a flow of subcritical water 122 from an interior chamber 420 through at least one aperture 412 in the needle portion 410 to thereby interface with tissue and deliver ablative energy to the targeted site 440.

Figure 9:
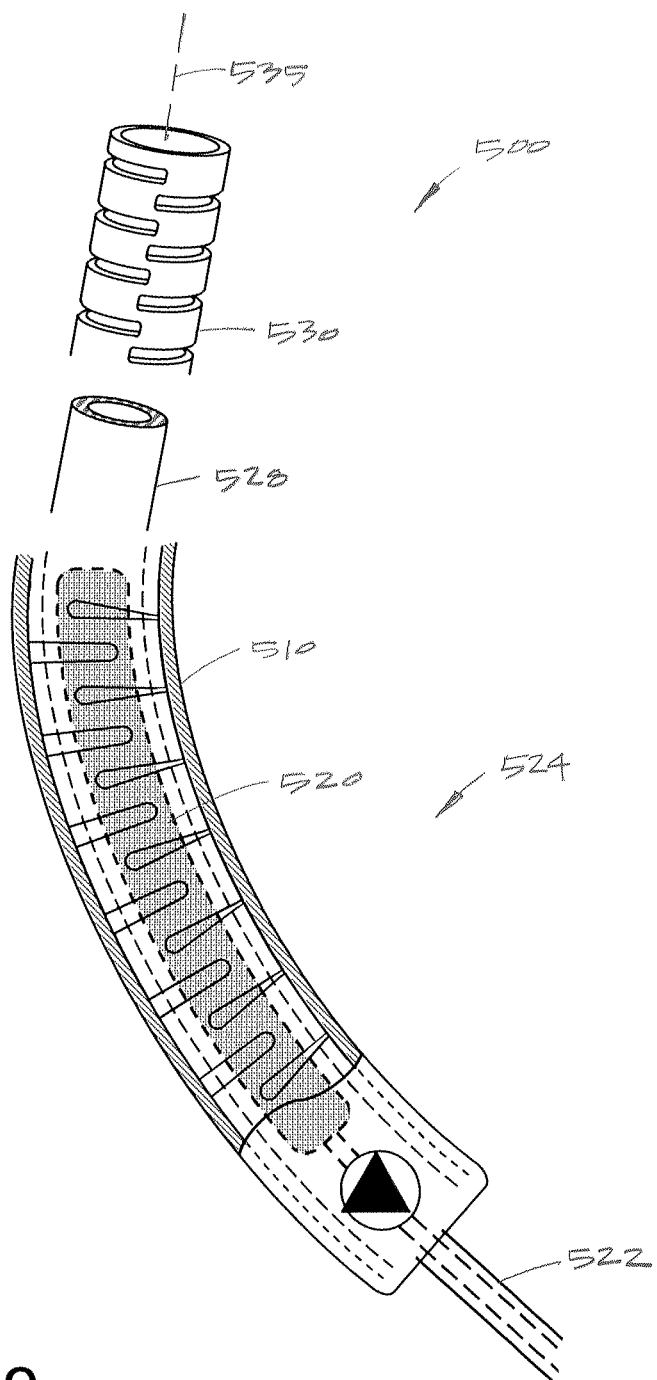
FIG. 9 is a sectional view of another variation of a probe similar to that of FIG. 5 with an interior chamber that is flexible.

FIG. 9 is a schematic view a distal portion of an alternative catheter 500 that again has a catheter body 510 that carries an interior chamber 520 adapted to carry subcritical water. The catheter body 510 again transitions in the distal direction to a needle portion 522. In this variation, the working end 524 including the interior chamber 520 is flexible to allow the catheter body 510 to flex when in a working channel of an articulating endoscope. In this variation, the interior chamber 520 can be within a flexible polymer sleeve 528, for example fabricated of PEEK tubing or another similar material. The polymer sleeve 528 is carried within the bore of a slotted metal hypotube or sleeve 530 as is known in the art for providing an articulating metal sleeve. In FIG. 9, the slotted sleeve 530 is shown in a form that allows for bending in one plane, but it should be appreciated that the sleeve can be slotted for flexing in any direction. As can be understood, the slotted metal sleeve 530 thus provides substantial strength surrounding the PEEK tubing 528 so that the pressure in the interior chamber 520 cannot expand the PEEK tubing radially outward from the axis 535 of the catheter. In this schematic illustration of FIG. 9, the heating mechanism is not shown, however, the heating mechanism can be a resistive heating element in interior chamber 520 of the type shown in FIG. 4A or an inductive heating system as shown in the embodiment of FIG. 5 were in the inductive coil would add another layer to the exterior of the catheter body 510 as shown in FIG. 9.

In another variation, first and second concentric slotted tubes (not shown) can be used with distal ends of such tubes welded together and a handle mechanism to axially move the first tube relative to the second tube to provide an articulating catheter working end that carries interior chamber 520.

Figure 10A:
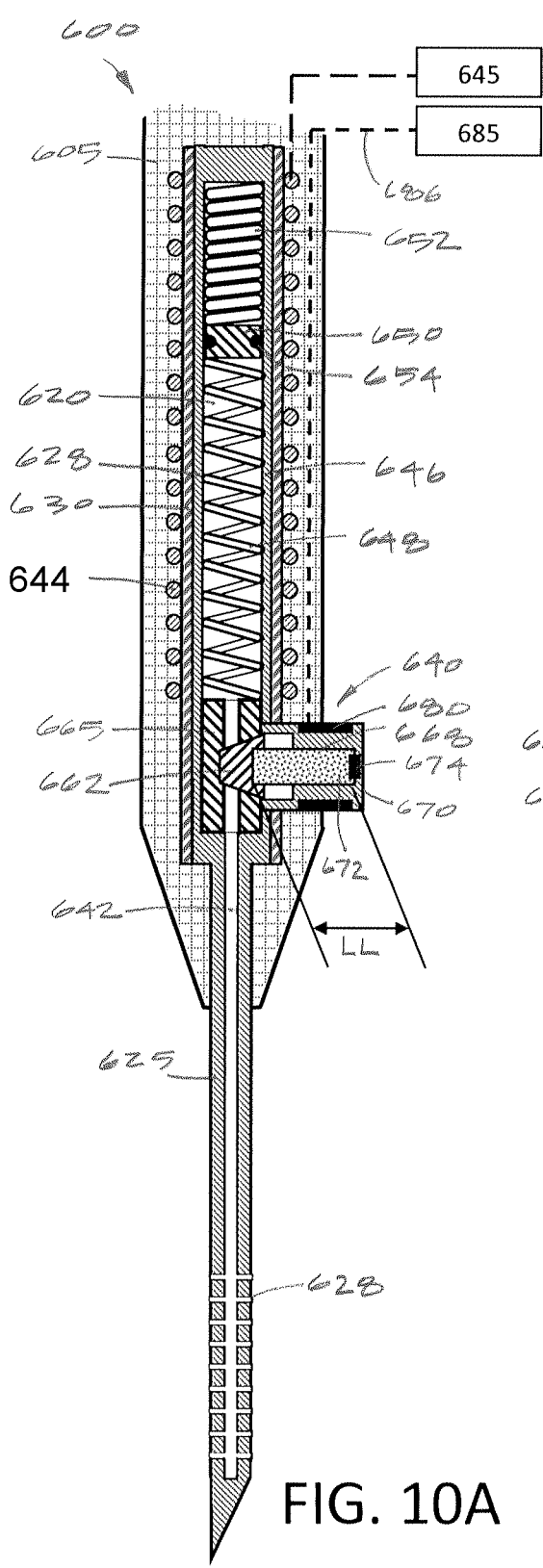
FIG. 10A is a sectional view of a working end of another variation of a probe similar to that of FIGS. 5 and 9 illustrating a different valve mechanism in a valve-closed position.
Figure 10B:
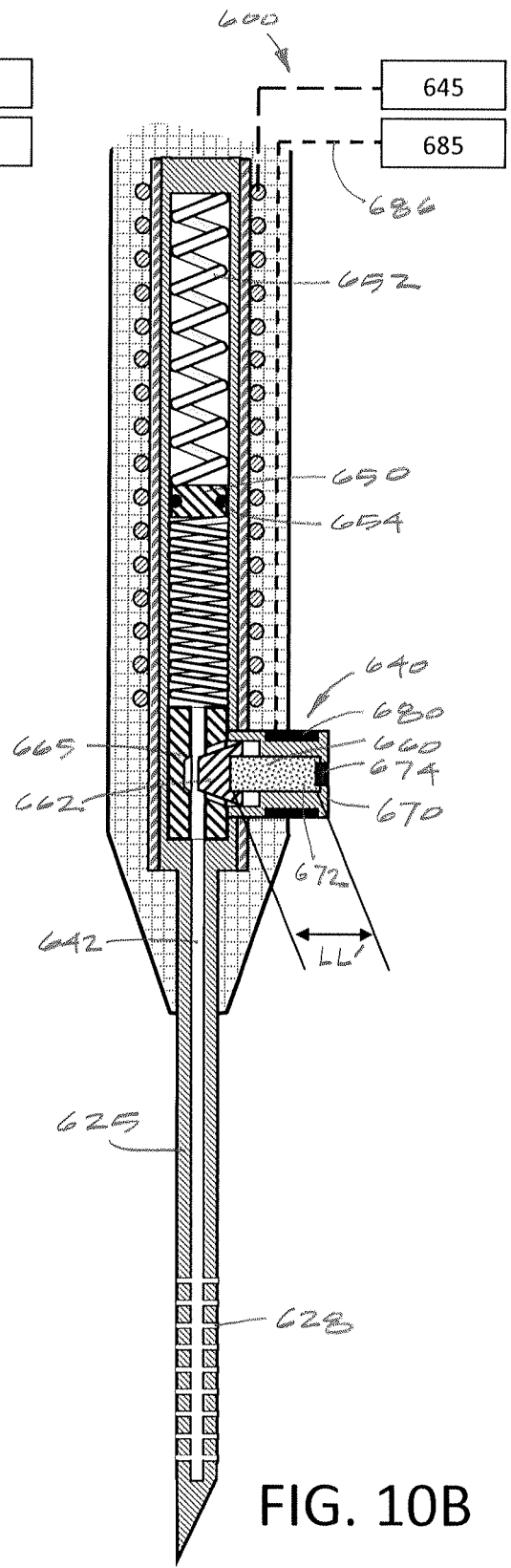
FIG. 10B is a sectional view of the valve mechanism of FIG. 10A in a valve-open position.

FIGS. 10A-10B illustrate another variation of a similar treatment device 600 with a working end of a probe body 605 carrying an interior chamber 620 and a distal needle portion 625. The interior chamber 620 can be carried within metal sleeve member 625 with a dielectric surrounding layer 630. The interior chamber 620 again is adapted to carry subcritical water and a valve or release mechanism 640 is adapted for releasing subcritical water into a flow passageway 642 extending through the needle portion 625 to at least one aperture 628 therein. The heating mechanism can be in the form as described previously where a helical coil 644 outward from dielectric layer 630 is coupled to electrical source 645 and is configured to inductively heat a wall 646 around the interior chamber 620 as well as heat transfer element 648 carried within the interior chamber. In this variation, the heat transfer element 648 is a helical spring element.

The variation of FIGS. 10A-10B differs from previous embodiments in two ways. First, the interior chamber 620 includes a piston 650 that is urged in the distal direction by a spring 652 wherein the fluid contents of the interior chamber when under pressure compress the piston 650 and spring 652. The piston 650 is illustrated with o-ring 654. As can be easily understood, during use, as the valve mechanism 640 (described below) can be opened to allow release of subcritical water, and then the piston 650 and spring 652 will be urged the distal direction under the force of spring 652 to eject a significant percentage of the total volume of subcritical water from interior chamber 620, which was not the case in previous embodiments. Further, the heat transfer element 648 carried within interior chamber 620 which is adapted for inductive heating can be a collapsible spring-like member which is far weaker than the piston spring 652.

The variation shown in FIGS. 10A-10B differs from previous embodiments in a second aspect, relating to the valve mechanism 640. In this variation, the valve mechanism 640 includes an actuatable valve shaft 660 adapted to move a tapered valve stem 662 relative to a valve seat 665 which moves transversely relative to the axis of the flow passageway 642. As can be seen in FIG. 10A, the valve shaft 660 is slidably disposed in a bore 668 in valve body 670. The outward end 672 of valve shaft 660 is coupled by weld 674 to the outward end of bore 668 in the valve body 670.

The tapered valve stem 662 is fixed to the SMA valve shaft 660 which again can be any shape memory alloy such as NiTi described previously. The SMA valve shaft 660 has a first temporary extended length LL shown in FIG. 10A and a second shortened memory length LL' shown FIG. 10B. In other words, the tapered valve stem 662 is seated in valve seat 665 in FIG. 10A when the SMA valve shaft 660 is in its temporary shape to provide a valve-closed position. Thereafter, heating the SMA valve shaft 660 will cause it to shorten to its memory shape to move the valve stem 662 away from valve seat 665 to provide a valve-open position which thus releases subcritical water from the interior chamber 620. The heating mechanism for heating the SMA valve shaft 660 can be a resistive heating element 680 coupled to electrical source 685 as shown in FIGS. 10A-10B which is coupled by electrical leads in cable 686 indicated schematically.

Figure 11:
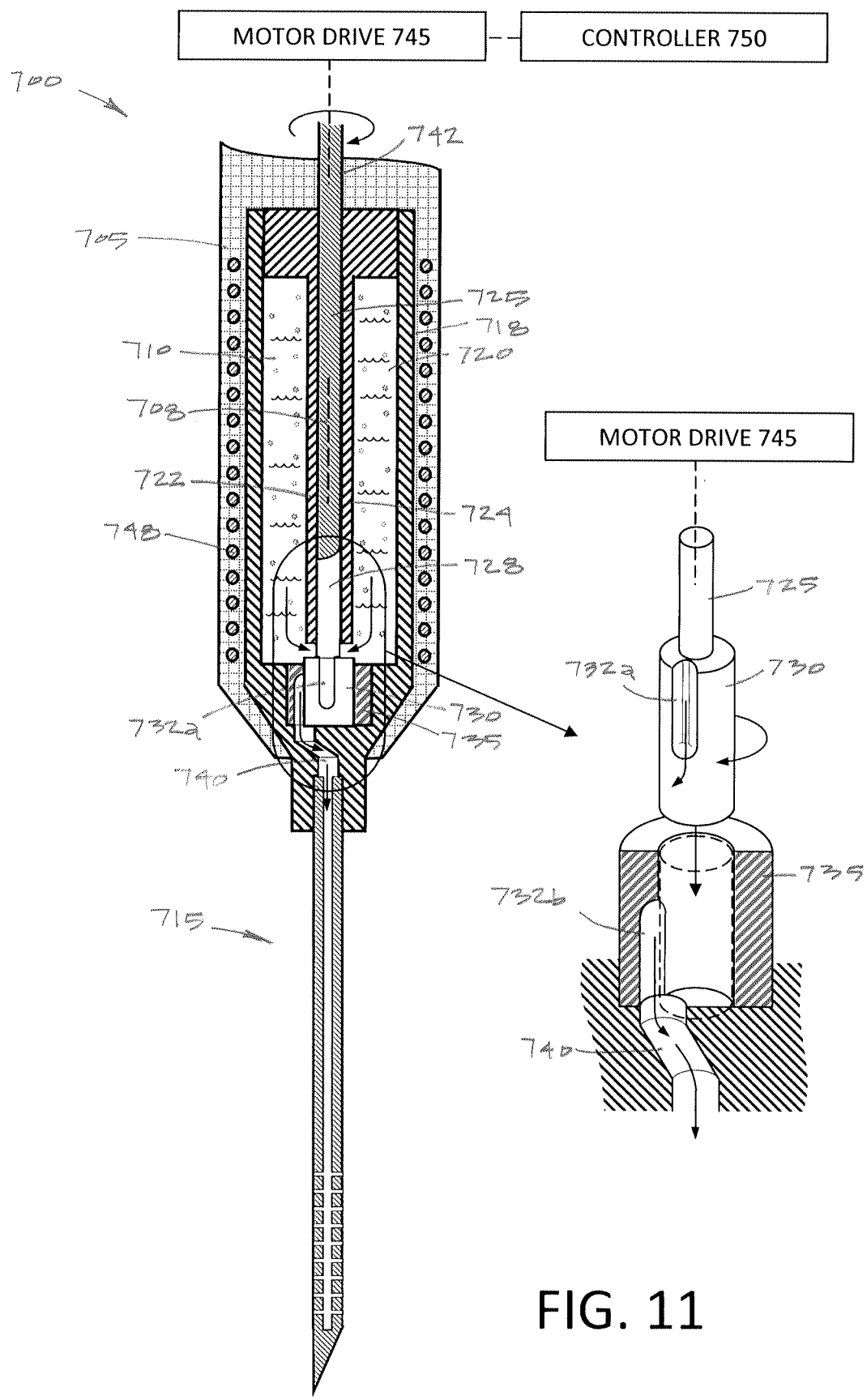
FIG. 11 is a sectional view of a working of another variation of a probe similar to that of FIGS. 10A-10B illustrating a different valve mechanism that is configured for pulsing the release of subcritical water from an interior chamber in a device body.

FIG. 11 illustrates another variation of a treatment probe 700 with a working end body 705 extending about axis 708 that again carried an interior chamber 710 and is connected to a distal needle portion 715. The probe of FIG. 11 differs from previous embodiments in that it additionally provides a pulsing mechanism for pulsing the release of subcritical water from the interior chamber 710. In the probe of FIG. 11, the interior chamber 710 has metal walls 718 surrounding a generally annular chamber portion 720 wherein a central wall portion 722 has a bore 724 with a motor-driven rotatable valve shaft 725 therein. The distal end 728 of the shaft 725 transitions to a rotating valve member 730 which flow channel 732a therein that when rotated will align with flow channel 732b in valve seat 735 to provide respective valve-closed and valve-open positions. An enlarged, exploded view of the rotating valve member 730 and valve seat 735 is shown on the right side of FIG. 11. The valve seat 735 has a distal end 736 that transitions to the interior passageway 740 in the needle portion 715 as in previous embodiments.

FIG. 11 illustrates the proximal end 742 of valve shaft 725 being coupled to a typical motor drive 745 which can rotate that shaft at selected speeds to rapidly move between valve-open and valve-closed positions to thereby pulse the flow of subcritical water 122 from the interior chamber 710 through the valve seat 735. In the variation of FIG. 11, an inductive coil 748 of the type described previously is shown connected to an electrical source and controller 750. The pulse rate can vary from 1 pulse/sec to 500 pulses/sec. The valve shaft can 725 can be stopped with the rotating valve member 730 in the valve-closed position by using a controller 750 and a motor drive 745 with an encoder or a spring mechanism can be used to stop rotation of the shaft 725 in a selected position.

The inductive coil 748 is adapted to heat the metal walls 718 and 722 around the interior chamber 710 but it should be appreciated that additional inductively heatable elements (not shown) can be carried within the interior chamber 710 as in previous embodiments. Further, a piston and spring arrangement having an annular configuration can be provided in the variation of FIG. 11 which would serve the functions described with reference to the device of FIGS. 10A-10B.

Figure 12:
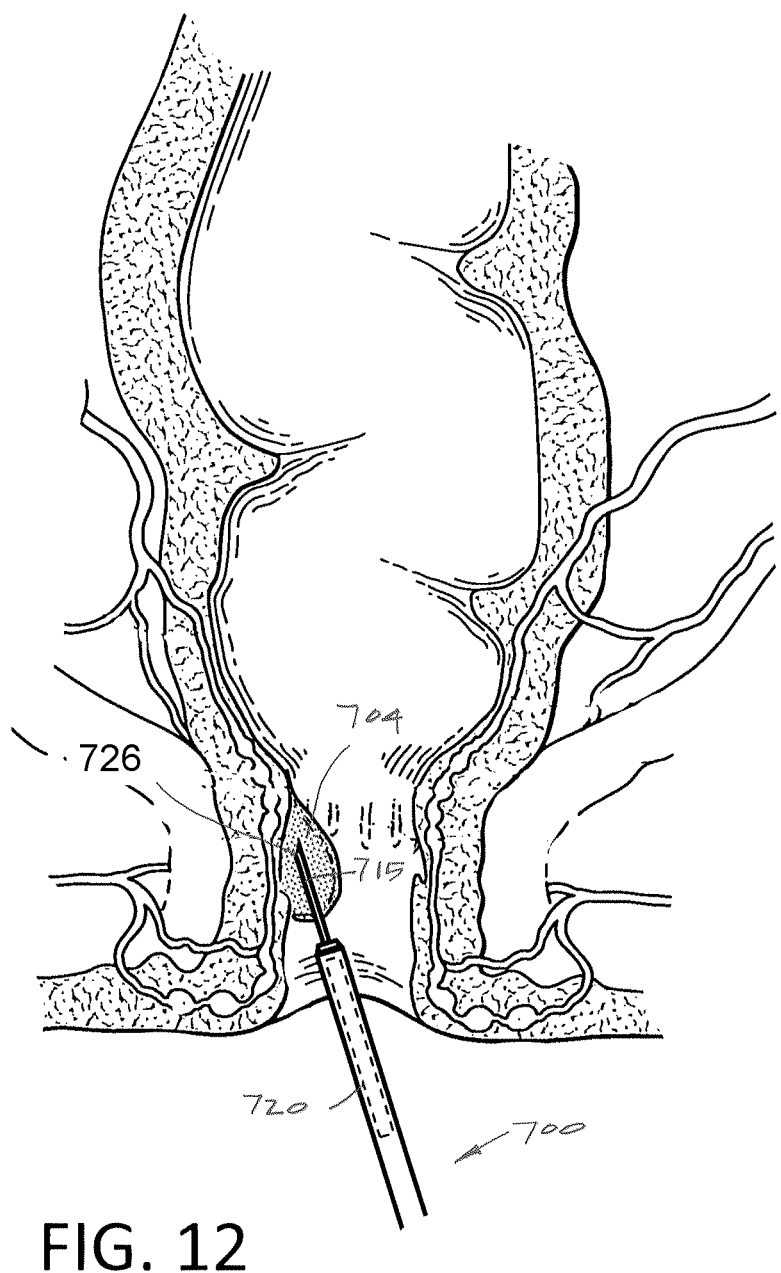
FIG. 12 is a schematic section view of a method of using a probe as in FIGS. 4A, 5, 10A or 11 to treat a patient's hemorrhoid.

FIG. 12 illustrates an ablation procedure with a probe 700 that has a pulsing mechanism as shown in FIG. 11 in a method of treating a hemorrhoid 704. In FIG. 12, the needle portion 715 of the probe 700 is inserted into a patient's hemorrhoid 704 and subcritical water is released in pulses from interior chamber 720 as described above. In the treatment of a hemorrhoid, the needle tip 724 can be moved axially during the pulsed energy delivery. Further, in large hemorrhoids, the needle portion 715 can be inserted at different locations or angled in different directions and thereafter the pulsed flows can be provided to optimize ablation of all regions of the vascular malformation that makes up the hemorrhoid.

Figure 13:
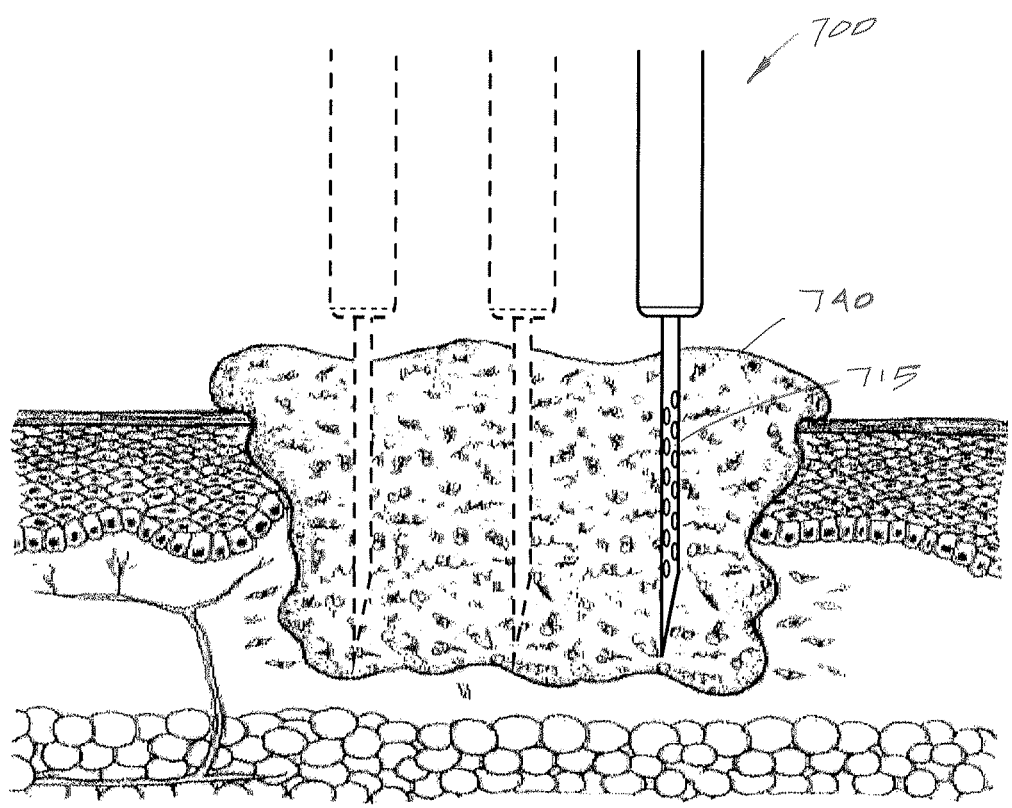
FIG. 13 is a schematic section view of a method of using a probe as in FIGS. 4A, 5, 10A or 11 to treat a keloid in a patient's skin.

FIG. 13 illustrates the treatment of a keloid 740 or abnormal scar tissue with a probe of the type shown in FIG. 11. A keloid can consist of fairly dense tissue, and therefore multiple sticks of the needle portion 715 may be optimal and the pulsed release of subcritical water from interior chamber 710 can cause better energy penetration into the tissue which will be followed by resorption of ablated tissue to reduce and/or eliminate the keloid 740.

Figure 14:
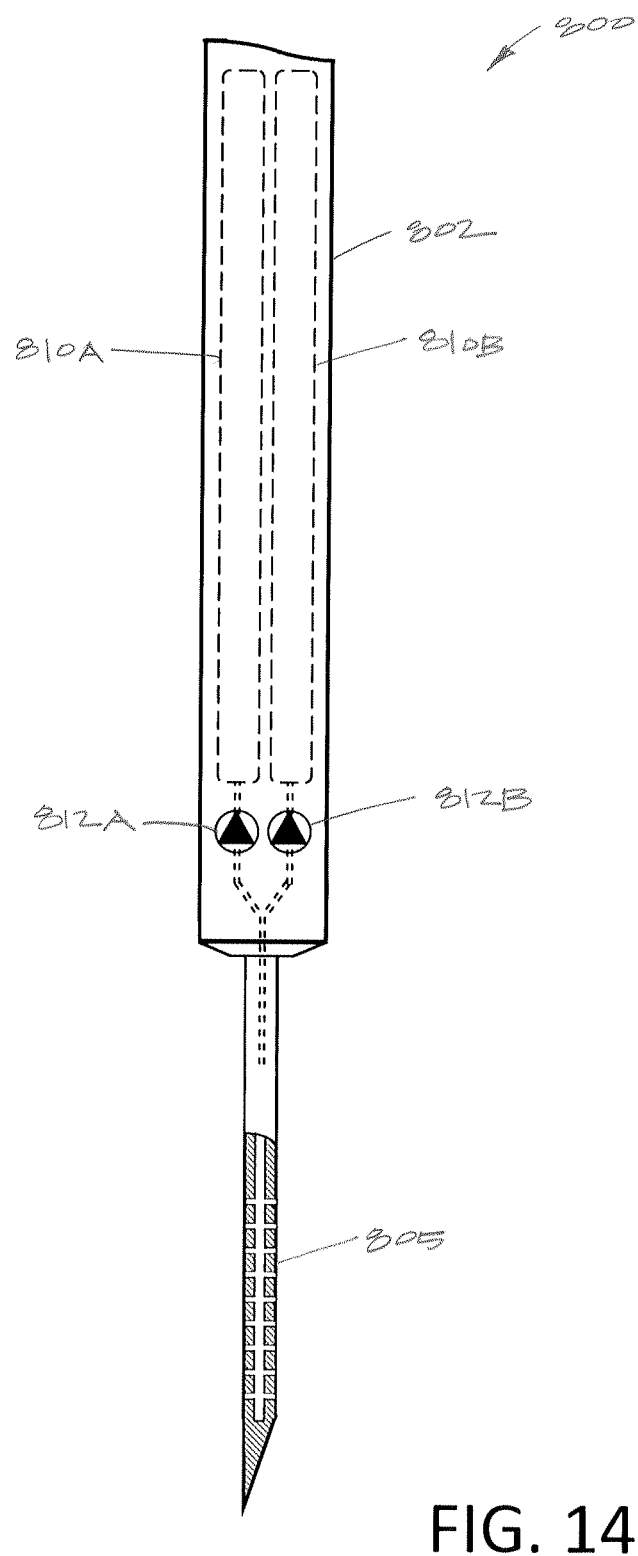
FIG. 14 is a schematic illustration of another probe with a working end that carries a plurality interior chambers configured to carry subcritical water and an independent valve mechanism for each interior chamber.

FIG. 14 schematically illustrates another catheter or probe 800 with a working end 802 extending to a needle portion 805 that is similar to the embodiments described above. In this variation, the probe 800 carries a plurality of interior chambers 810A and 810B and cooperating valve mechanisms 812A and 812B to allow for sequential energy delivery from each interior chamber. In this variation, such interior chambers 810A and 810B can be side-by-side or spaced axially apart within the working end 802. The number interior chambers can range from 2 to 6 or more, and each interior chamber can have an independent heating mechanism of any type described previously or a single heating mechanism can be used to heat all the interior chambers simultaneously to provide subcritical water. In any event, each valve mechanism 812A and 812B can be opened independently of any other valve mechanism. The use of multiple interior chambers 810A and 810B provides for enhanced safety since the failure of any valve can only release energy from a single small chamber rather than a single larger interior chamber. In this variation, the multiple chamber device then provides for an increased total of amount of energy that can be delivered from the probe. Each chamber 810A and 810B can carry a predetermined energy dose which allows for less complex, single-use valves that are openable but not closeable as described above.

Figure 15:
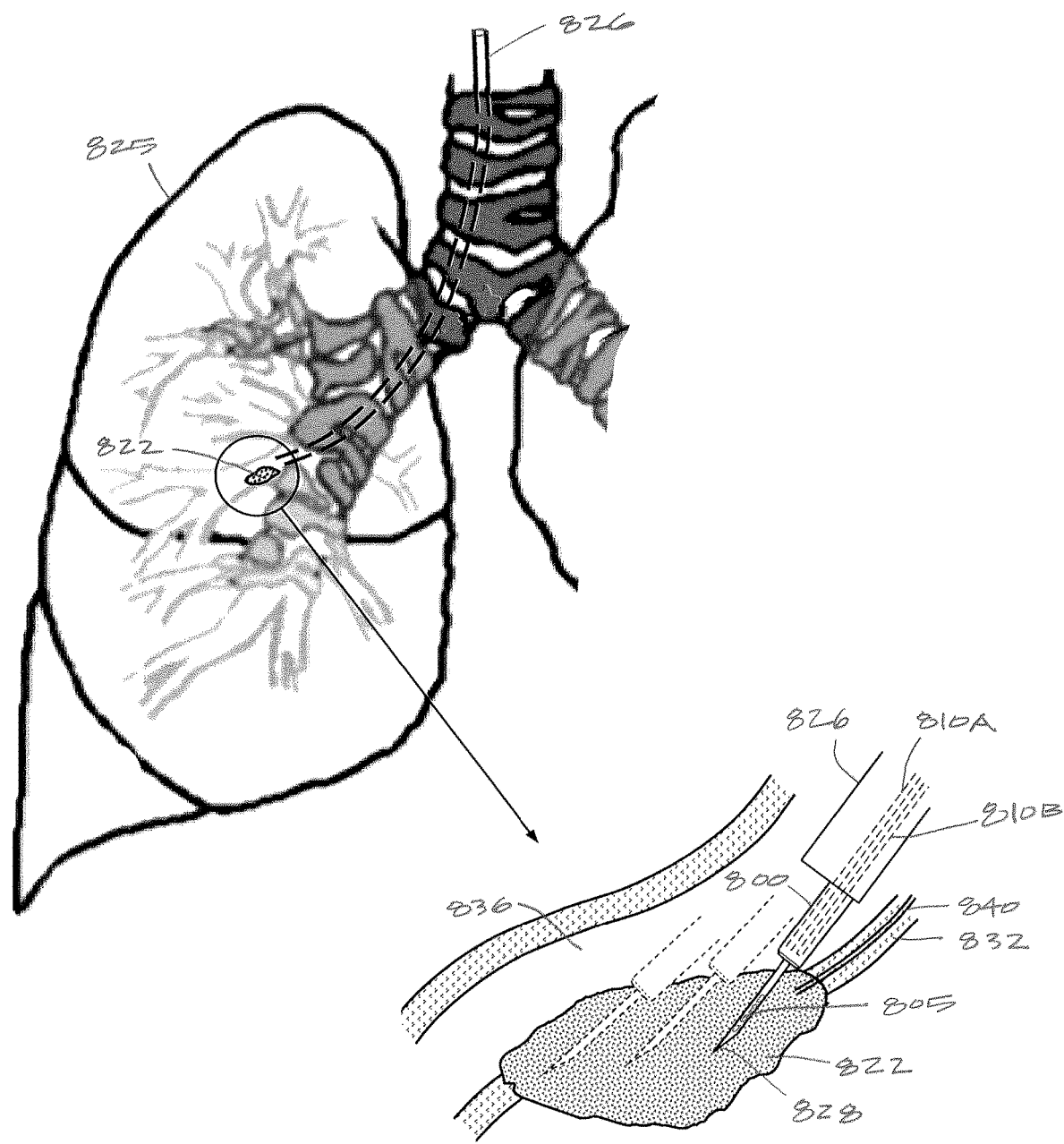
FIG. 15 is a schematic view of a method of using a probe as in FIGS. 4A, 5, 10A or 11 to treat abnormal tissue in a patient's lung, such as a nodule or tumor.

FIG. 15 illustrates a method of using the catheter 800 of FIG. 14 in treating a cancerous nodule 822 in a patient's lung 825. It should be appreciated that an elongated catheter 800 with multiple interior chambers 810A and 810B (FIG. 14) is useful in a treatment which requires time-consuming navigation of the catheter working end 802 to the targeted site and thereafter may require multiple needle sticks. The need for multiple needle sticks may be needed in treating lung cancer sites. In FIG. 15, it can be seen that the working end 802 is extended outwardly from endo scope 826 and the needle portion 805 is inserted into the nodule or tumor 822 in multiple locations as is needed to ablate the entire nodule or multiple nodules. Alternatively, or additionally, the needle tip 828 can be penetrated into the wall 832 around the lumen 836 to ablate blood vessels 840 therein that feed the malignancies.

Figures 16A, 16B:
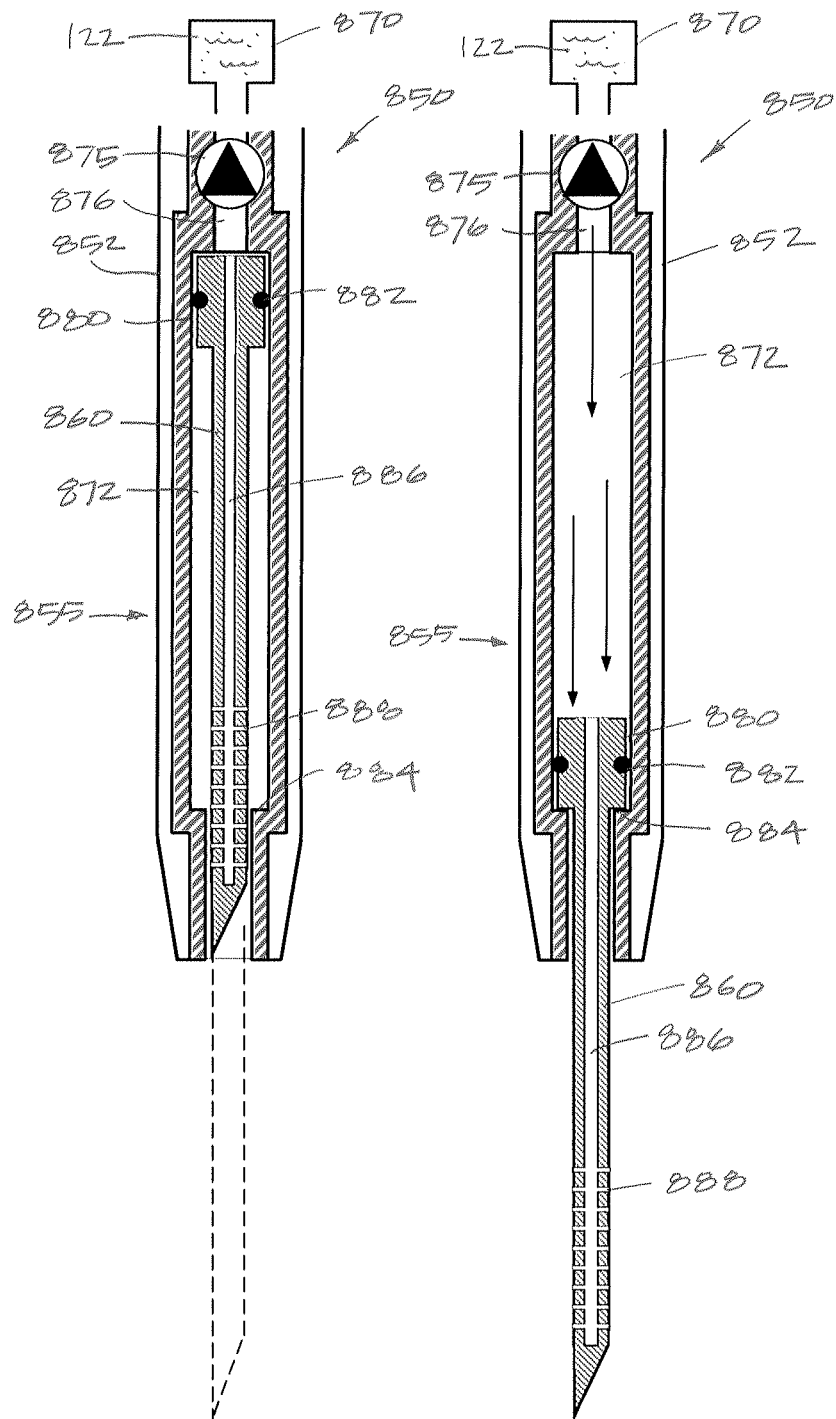
FIG. 16A is a sectional view of a working end of another ablation probe with a needle member that is ballistically extendable from the device body, showing the needle member in an initial non-extended position.
FIG. 16B is another sectional view of the working end of FIG. 16A showing the needle member in an extended position.

FIGS. 16A and 16B illustrate another probe 850 with a probe body 852 and working end 855 that is similar to that of FIGS. 2, 4A, 5, 9, 10A and 11 but which differs in that the working end includes an extendable needle portion 860 that can be extended at a highly accelerated rate from the probe body 852 for penetrating tissue. More particularly, the needle portion 860 can be extended ballistically by the fluid pressure and expelling forces provided by the release of pressurized thermal fluid or subcritical water 122 from the interior chamber 870 shown schematically. In other words, the needle portion 860 can be driven into tissue at a high speed as opposed to inserting the needle portion under manual force. The use of pressure driven needle insertion is useful when the needle is at the end of an elongate probe, for example, as shown in FIG. 11 or other treatments were an endoscope is navigated through a body lumen and the needle portion 860 is carried by elongated catheter or device 850.

Referring to FIG. 16A, it can be seen that the needle portion 860 is in a retracted or non-extended position within a cylindrical channel 872 in the working end 855 of the probe body 852. The release mechanism 875 is shown in flow passageway 876 that leads to channel 872 carrying the extendable needle portion 860. The needle portion 860 has a proximal collar 880 with an o-ring 882 that seals the collar 880 in the cylindrical channel 872. It can be understood that in an extended position, the collar 880 bumps into the distal flange 884 around the channel 872 to thereby limit the distal travel of the needle portion 860.

Now referring to FIG. 16B, the needle portion 860 can be seen in an extended position relative to the probe body 852. It can easily be understood that when the release mechanism 875 releases subcritical water from the interior chamber 870, the high fluid pressure will cause the needle portion 860 to accelerate towards the extended position of FIG. 16B at the same time that fluid flow through the interior passageway 886 of the needle portion to the outflow apertures 888. It can be understood that the fluid pressure will cause the needle portion 860 to accelerate in any design in which the flow passageway 886 in the needle portion 860 restricts the flow of the thermal fluid through the passageway 886 and outflow apertures 888.

Figures 17A, 17B:
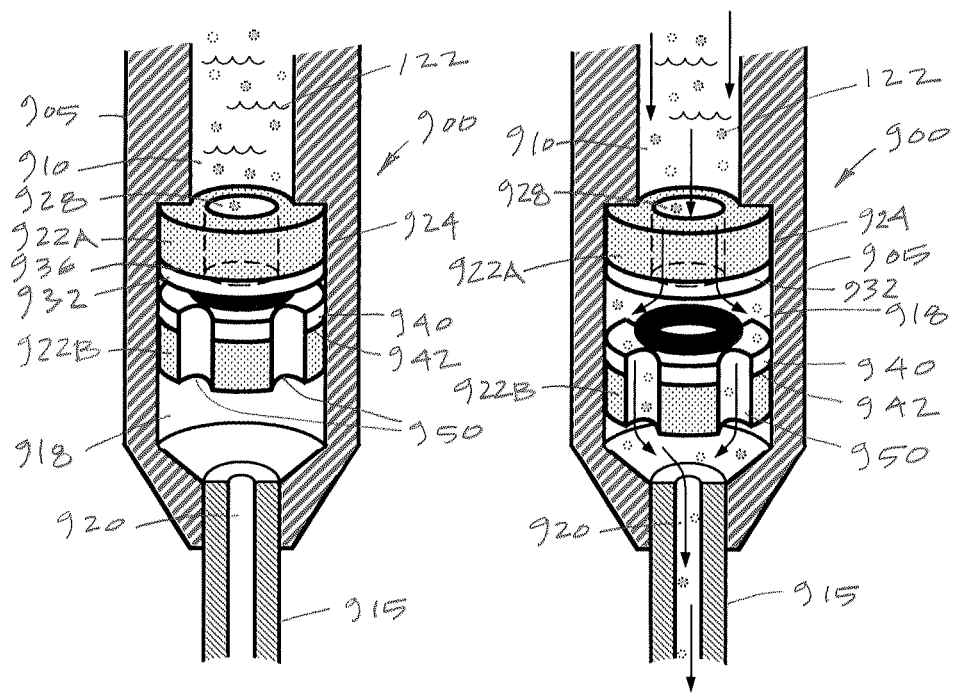
FIG. 17A is a sectional view of another variation of a release mechanism that comprises a magnetically-controlled pressure relief valve shown in a valve-closed position.
FIG. 17B a sectional view of the magnetically-controlled pressure relief valve of FIG. 17A shown in a valve-open position.

FIGS. 17A-17B illustrate another variation of a valve mechanism or subcritical water release mechanism 900 which is space-saving and is suitable for use in the working end of an elongate catheter as in FIG. 14 since no electrical connections are needed to actuate the mechanism. FIG. 17A illustrates a probe body 905 with an interior chamber 910 shown schematically that carries subcritical water 122 as described previously. The probe body 905 extends distally to a needle portion 915. For convenience, a heating mechanism is not shown in FIGS. 17A-17B, but can be any of the heating mechanisms described in previous embodiments above. The valve mechanism 900 consists of a magnetically-controlled pressure relief valve disposed in a cylindrical chamber 918 between the interior chamber 910 and flow passageway 920 in the needle portion 915. As can be seen in FIG. 17A, a first permanent magnet 922A cooperates with a second permanent magnet 922B to provide a valve-closed position. The magnets can be a rare-earth type such as neodymium magnets. In FIG. 17A, the first or proximal magnet 922A is fixed mechanically, or by adhesives, in the proximal end 924 of cylindrical chamber 918. A flow channel 928 extends through the first magnet 922A and an optional polymer washer 932 attached to the distal surface 936 of the magnet 922A.

In FIG. 17A, the second or distal magnet 922B is dimensioned to float or move within the cylindrical chamber 918. A polymer washer 940 is attached to the proximal surface 942 of magnet 922B and a seal or o-ring 945 is coupled to the washer 940. At least one flow channel 950 is formed into an outer perimeter of the distal magnet 932B and washer 940, and the variation of FIG. 17A illustrates four perimeter flow channels 950. Thus, in FIG. 17A, it can be seen that the magnetic attraction between magnets 922A and 922B will provide a valve-closed position and seal the interior chamber 910.

FIG. 17B next depicts an increase in fluid pressure in interior chamber 910 which overcomes the magnetic attraction between magnets 922A and 922B and thereafter the distal magnet 922B is displaced in the distal direction in cylindrical chamber 918 to provide a valve-open position. The magnetic valve 900 can perform optimally in this application since its release or opening is very fast and can be designed to fully open at a precise cracking pressure to provide a fully-open position and a fully-closed position. The fully-open position of FIG. 17B is achieved practically instantly due to the rapid decay of the magnetic field as the fluid flow pushes the second magnet 922 to the open position. This magnetic mechanism differs from spring-based pressure relief valves that require increasing pressure and force to continually compress the spring and open a conventional pressure relief valve.

Figure 18:
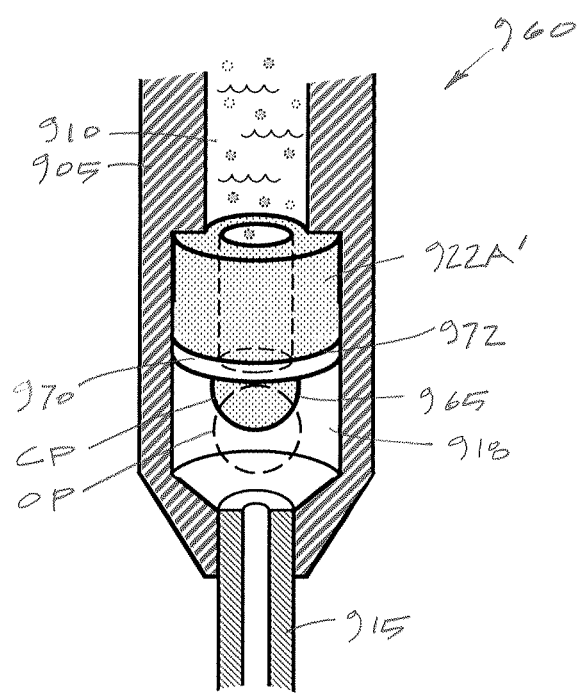
FIG. 18 is a sectional view of another variation of a magnetically-controlled pressure relief valve in a valve-closed position.

In FIG. 18 illustrates another magnetic release mechanism 960 which is similar to that of FIGS. 17A-17B except that the distal magnet 965 is a spherical magnet that is configured to float or move within the cylindrical chamber 918 between a valve-closed position CP and an open position OP. In this variation, the proximal magnet 922A' can have a polymer or elastomeric sealing washer 970 attached to the distal surface of the magnet to provide a seal against the spherical magnet 965. In any of the variations of FIGS. 17A and 18, the walls of the cylindrical chamber 918 can have an insulative layer (not shown), such as a ceramic, to limit heat transfer to the device body 905. Similarly, the magnets 922A, 922B or 922A' and 965 can have a. surface layer of a ceramic or other thermal insulator.

Figure 19A:
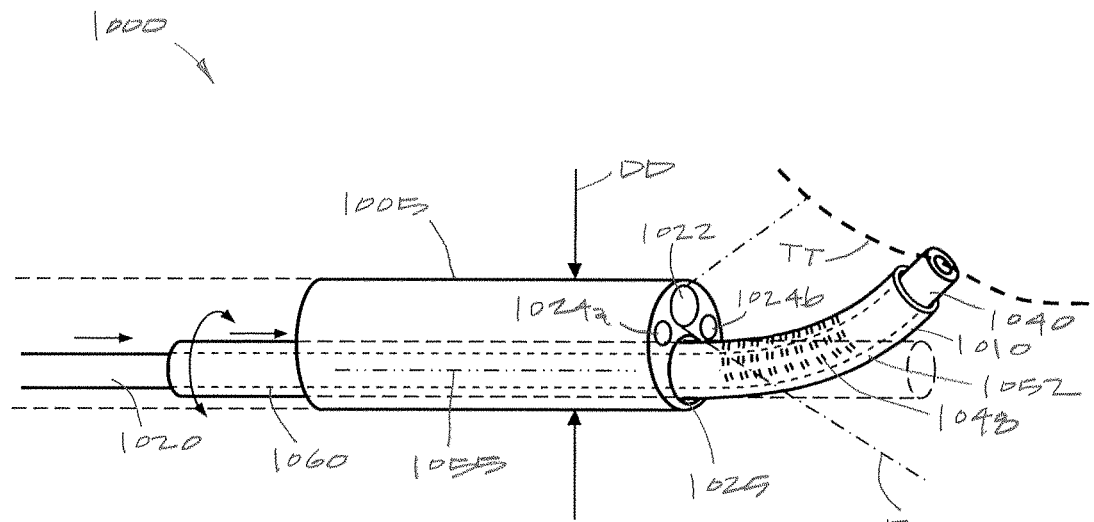
FIG. 19A is a cut-away view of a working end of an integrated ablation system including an endoscope component with a distal imaging sensor, and articulating sleeve component and a flexible ablation catheter or probe similar to that of FIGS. 14 and 16A, with the needle portion in a non-extended position.
Figure 19B:
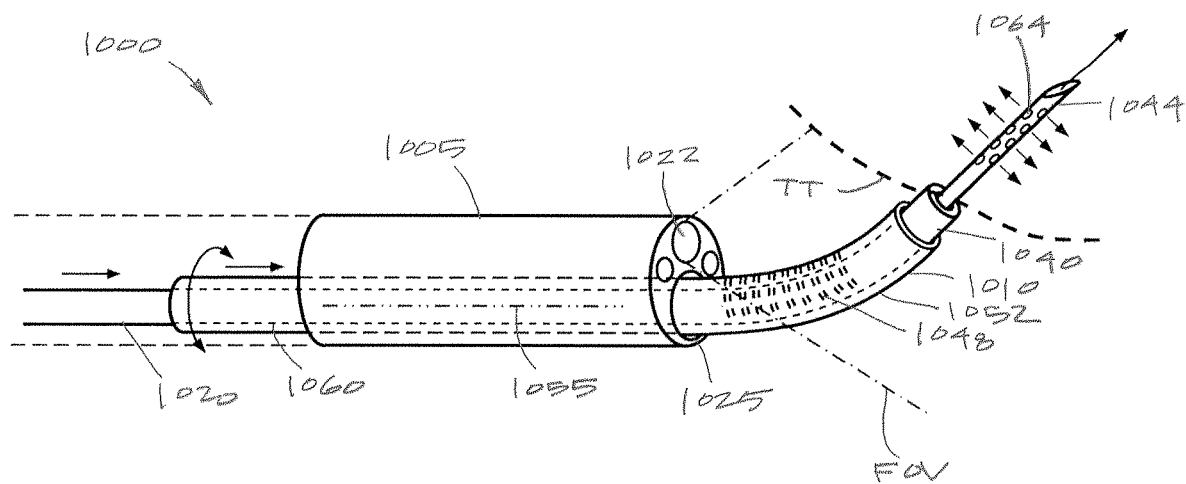
FIG. 19B is another view of the working end of the system of FIG. 19A with the needle portion in an extended position.

FIGS. 19A-19B illustrate another system 1000 corresponding to the invention for performing an ablation procedure, that comprises multiple components, including an endoscopic viewing component or endoscope 1005, an articulating sleeve assembly 1010 and an ablation stick or probe 1020 that is similar to the variations described above. In one variation, the system 1000 has an elongate endoscope 1005 that is less or equal to 6 mm in diameter DD and is often less than 5 mm diameter that carries a distal imaging sensor 1022 having field of view FOV for endoscopic viewing as is known in the art. The imaging sensor 1022 can be angled have any suitable viewing angle from 0° to 70° or more for particular procedures and different angles of field of view. Additionally, the endoscope 1005 may carry one or more channels 1024a and 1024b for fluid inflows and outflows or for pressure sensing. The endoscope 1005 also would carry LEDs or another light transmitting mechanism (not shown). The endoscope 1005 may be disposable and has a working channel 1025 that has a diameter ranging between 2 mm and 4 mm. Thus, the system 1000 allows for navigation within a lumen in the patient's body with an endoscope 1005 that is less than 6 mm in diameter and an ablation probe 1020 with a working end 1040 that can be advanced and rotated relative to an articulating sleeve 1010 to thereby direct a needle portion 1044 (FIG. 19B) in any direction desired to deliver ablative energy to tissue.

As can be understood from in FIG. 19A, the articulating sleeve 1010 can consist of concentric first and second slotted hypotubes indicated at 1048 (collectively) that can be articulated from a proximal handle (not shown) as is known in the art. The articulating region 1052 of the sleeve assembly 1010 can articulate up to 90° or more from its longitudinal axis 1055. Further, the articulating region 1052 can be rotated 360° within the working channel 1025 as well as translated longitudinally relative to endoscope 1005 and the imaging sensor 1022. As can be seen in FIG. 17A, the central channel 1060 in the articulating sleeve assembly 1010 is adapted to receive the elongate, flexible ablation stick or probe 1020 of the type described in FIGS. 16A-16B above. Thus, FIG. 19A depicts initial steps of a method of using the system 1000 wherein (i) the endoscope 1005 is navigated into the interior of a patient's body proximate to targeted tissue TT, (ii) the articulating sleeve assembly 1010 is introduced through the working channel 1025 in the endoscope 1005 and the articulating region 1052 is articulated, and (iii) the ablation probe 1020 is inserted through the central channel 1060 of the sleeve assembly 1010 so that its working end 1040 (with its needle portion 1044 retracted) is in contact with the targeted tissue TT.

FIG. 19B illustrates a subsequent step in a method of ablating the targeted tissue TT wherein a release mechanism, such as the subcritical water release mechanism of FIGS. 17A-17B is used in conjunction with a heating mechanism to cause (i) ballistic extension of the needle portion 1044 into the targeted tissue TT and (ii) flow of the thermal treatment fluid through apertures 1064 in the needle portion 1044 to interface with tissue to cause the ablation. In this variation, the ablation probe 1020 again provides a source of thermal treatment fluid in a specified volume or having a specified energy delivery capacity. In general, the system 1000 of the invention includes an elongated member or endoscope 1005 carrying a distal imaging sensor, and articulated sleeve assembly 1010 that carries a central channel 1060, and a flexible ablation probe 1020 adapted for providing a thermal ablation fluid to interface with tissue wherein the system 1000 is configured to deliver one or more doses of energy where each dose ranges from 5 to 1000 calories. Although the system 1000 is described with separable components, variations include an endoscope 1005 and the articulating sleeve 1010 that are combined into a single disposable component, or an articulating sleeve 1010 and ablation probe that are combined into a single disposable or all three components can be combined and fall within the scope of the invention.

Figure 20A:
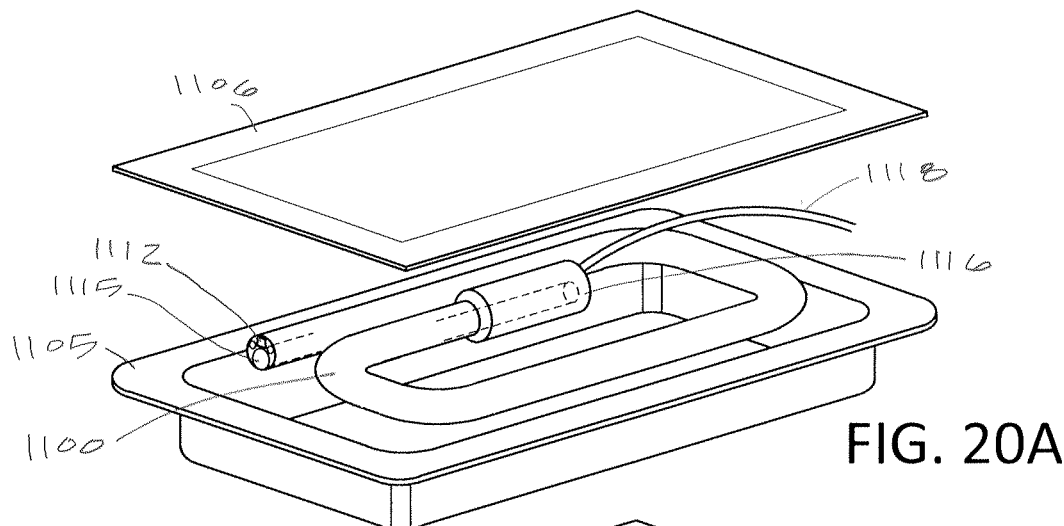
Figure 20B:
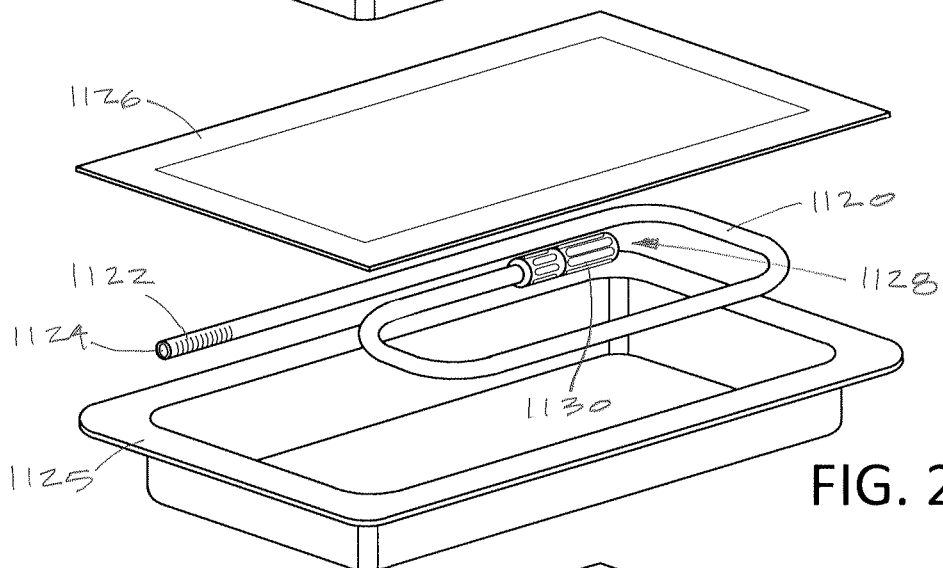
Figure 20C:
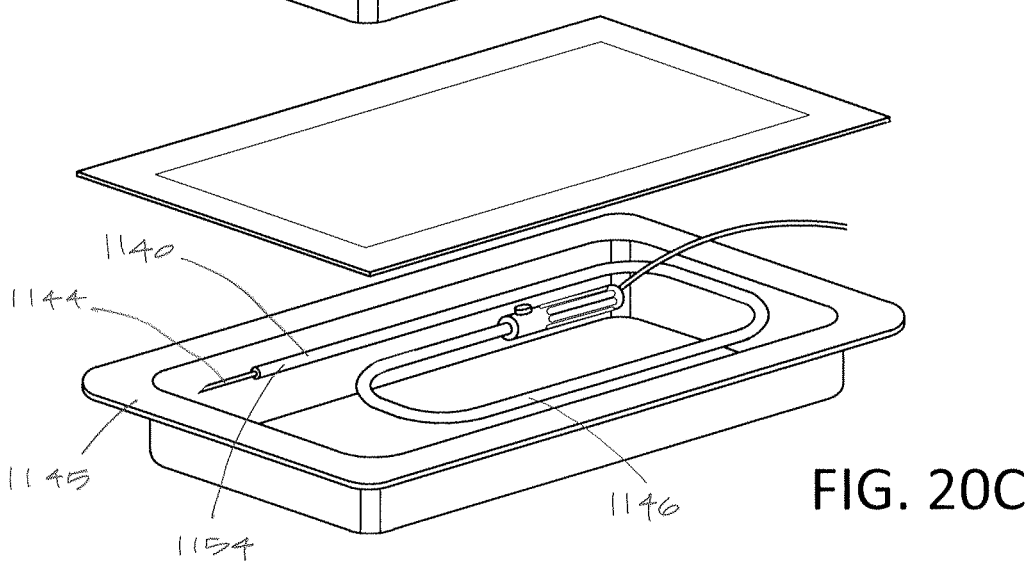

FIGS. 20A-20C illustrate in ablation system that can be assembled from individual functional components that are separately packaged in sterile trays to provide a custom treatment kit. FIG. 20A illustrates an elongated flexible endoscope component 1100 of the type that can be used for accessing a patient's lung or a treatment site in a patient's gastrointestinal tract, which may be an articulating endoscope as is known in the art. The endoscope 1100 is shown in tray 1005 with the tray top 1106 removed. In one variation, the endoscope 1100 has a distal imaging sensor 1112 is a working channel 1115 extending from the handle 1116 through the endoscope. Light fibers and additional fluid flow channels can be provided in the endoscope as is known in the prior art. A multifunctional cable 1118 extends from the endoscope 1000 to a light source, an imaging processor and an image display system as is known in the art.

FIG. 20B then illustrates an elongated articulating catheter 1120 with a distal articulating region 1122 that is dimensioned for introduction through the working channel 1115 in the endoscope 1100 of FIG. 20A. The catheter 1120 has an interior passageway 1124 and is shown in sterile tray 1125 with the tray top 1126 removed. The handle 1128 of the catheter includes an actuator, for example a rotating member 1130, that is configured to articulate the articulating region 1122 of the catheter that extends outwardly from distal end of endoscope 1100 of FIG. 20A within the endoscope's field of view.

Finally, FIG. 20C illustrates an elongated ablation probe 1140 with an extendable needle 1144 shown in an extended position for purposes of description only. The needle assembly is similar to needle types described previously. The ablation probe 1140 in tray 1145 comprises a highly elongated flexible shaft 1146 that can be introduced through the passageway 1124 in the articulating catheter 1120 of FIG. 20B to extend outwardly from the distal end of the catheter 1120. The physician then can rotate and articulate the articulating catheter 1120 which will flex the distal end 1154 of the ablation probe 1140 and orient the needle 1144 at any rotational angle and direction for penetrating the needle 1144 into a targeted site. It can be understood that the ablation probe 1140 can be selected from inventory of probes, based on probe operating parameters and configurations, for example including (i) total energy delivered by subcritical water release, (ii) selected rate of energy delivery over a selected time interval, (iii) needle length for depth of penetration; (iv) needle gauge, (v) needle rigidity or flexibility, (vi) dimensions and orientation of flow outlets in the needle, (vii) acceleration rate of the needle for penetrating tissue, (viii) retractability or non-retractability of the needle, (ix) type of release mechanism for releasing subcritical water from an interior chamber for flow to the needle, and (x) selection of a probe with a single chamber or multiple chambers for delivering subcritical water to a targeted site.

Figure 21A:
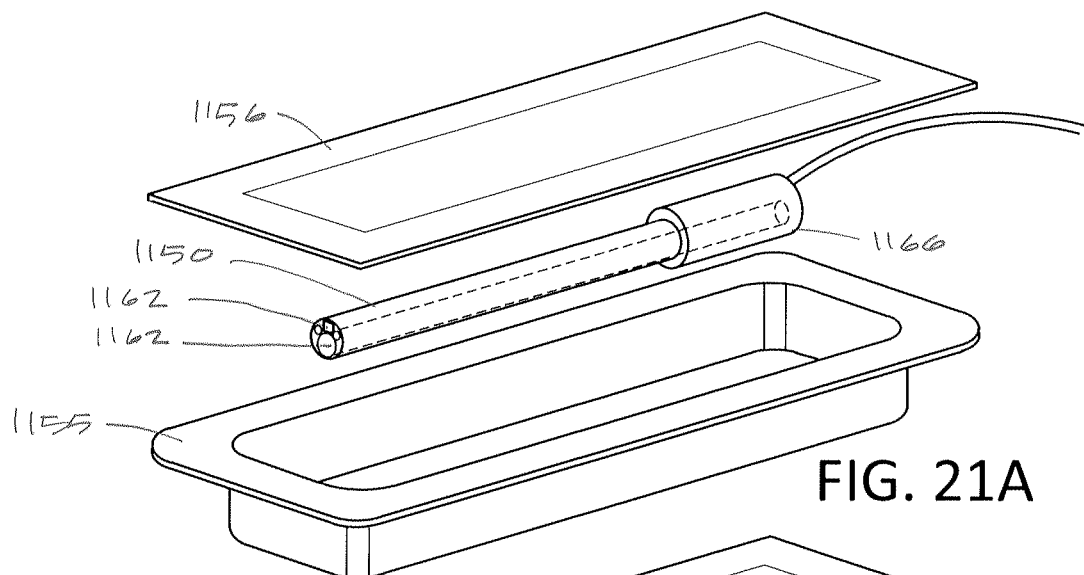
Figure 21B:
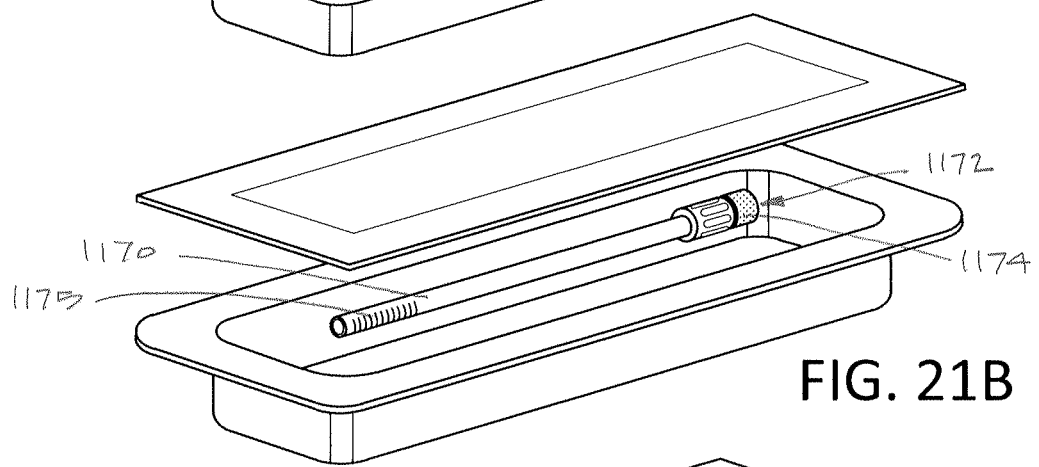
Figure 21C:
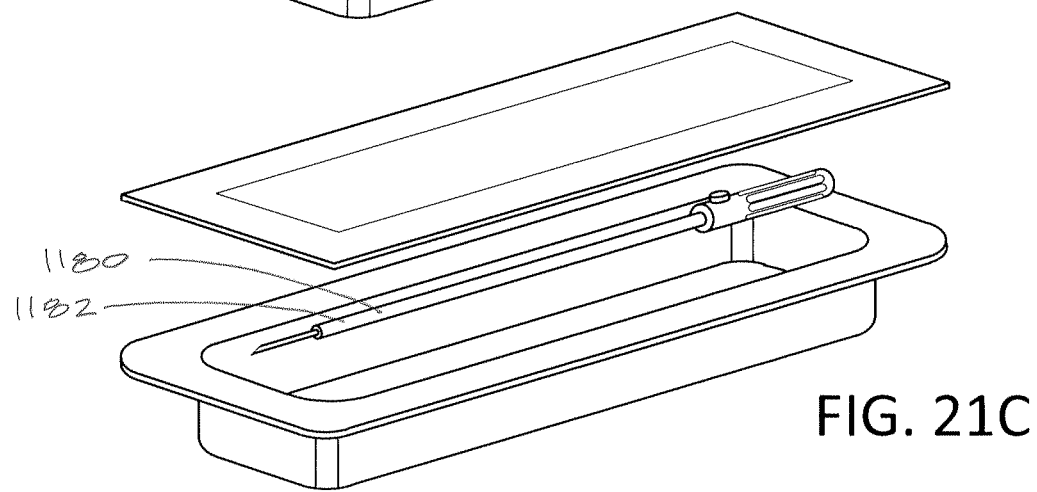

FIGS. 21A-21C illustrate another variation of ablation system or kit that is similar to FIGS. 20A-20C except that FIG. 21A-21C illustrate an endoscope 1150 and other components that are relatively short rather than the elongated flexible endoscope 1100 and kit of FIGS. 20A-20C. In this variation, FIG. 21A illustrates a rigid endoscope 1150 that be used in gynecology, ENT, urology, laparoscopy or the like. The endoscope 1150 is shown in tray 1155 with the tray top 1156 removed. In a variation, the endoscope 1150 has a distal imaging sensor 1162 and a working channel 1165 extending from the handle 1166 through the endoscope.

FIG. 21B depicts a cooperating articulating catheter 1170 that has suitable length for extending through the working channel 1165 of the endoscope 1150. The catheter handle 1172 has an actuator element 1174 for articulating the articulating region 1175 of the catheter as described previously.

FIG. 21C shows an ablation probe 1180 has a flexible distal section 1182 that is adapted to cooperate with the articulating region 1175 of the catheter 1170 of FIG. 21B. Again, the ablation probe 1180 can be selected from an inventory of probes to provide the selected ablation parameters and a needle configuration as described previously with reference to FIG. 20C.

Figures 22A, 22B:
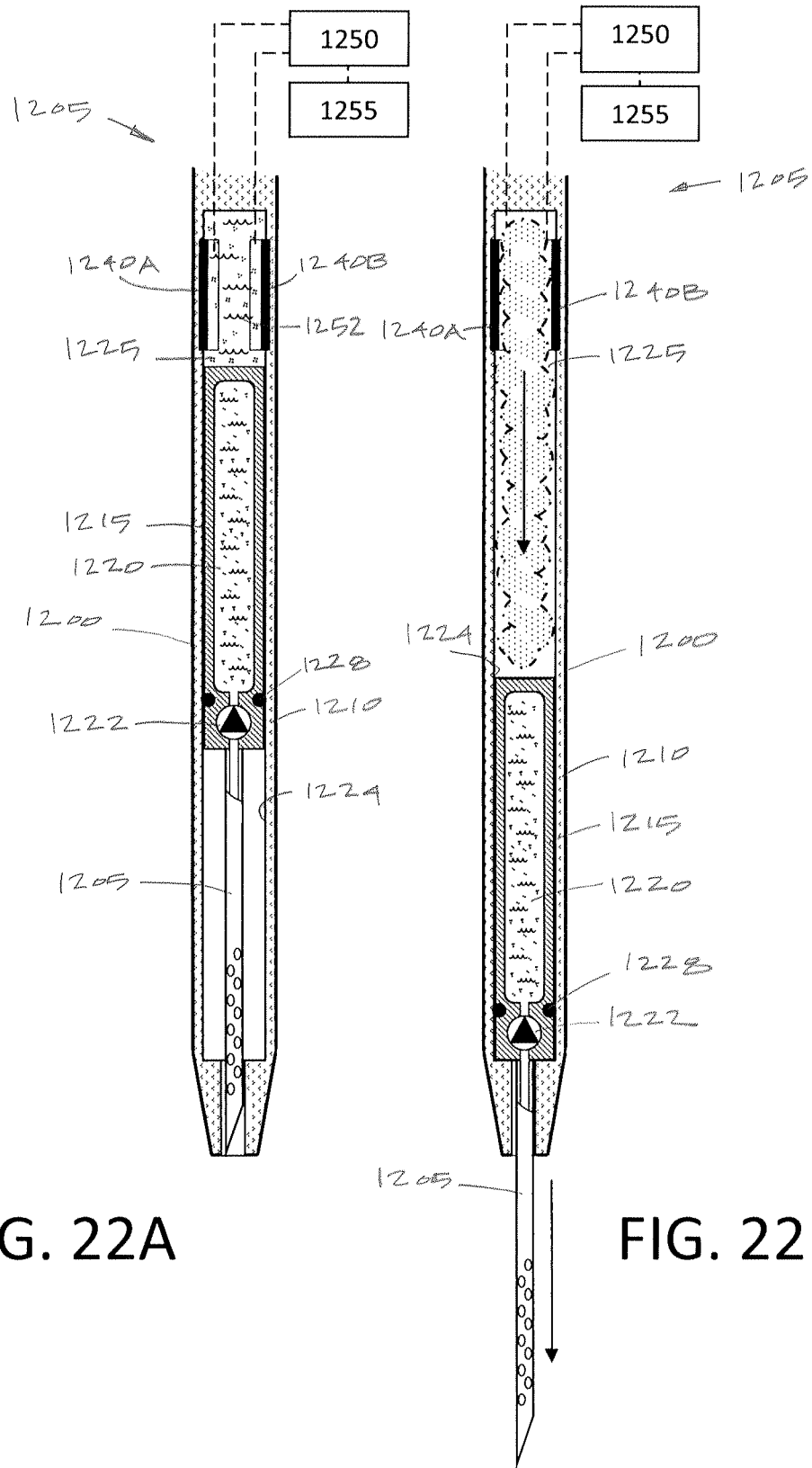
FIG. 22A is a view of the working end of another probe variation with a distal needle portion in a non-extended position as described previously with a fluid-filled chamber and electrode arrangement adapted for ballistic advancement of the needle from a non-extended position to an extended position and wherein a controller can vary the power level delivered to the electrode arrangement to provide a plurality of needle acceleration rates.
FIG. 22B illustrates the needle of FIG. 22A in an extended position following the explosive vaporization of fluid in the fluid-filled chamber to move the needle from the non-extended position to the extended position.

FIG. 22A is a sectional view of a working end 1200 of another variation of ablation probe 1204 with a distal needle 1205 in a non-extended position. In this variation, the probe body 1210 carries a movable needle assembly 1215 that carries the fluid-filled chamber 1220, wherein the needle assembly 1215 comprises a movable component that can be advanced outwardly from the probe body 1210. The needle assembly 1215 further carries a release mechanism 1222 of any type described previously. As can be seen in FIG. 22A, the needle assembly 1215 is movable within a cylindrical bore 1224 of the probe body 1210. For clarity in describing the needle advancement mechanism in this variation, FIGS. 22A-22B do not illustrate the heating mechanism that is used to provide the subcritical water in fluid-filled chamber 1220. However, it should be appreciated that any of the heating mechanisms described in previous embodiments can be integrated into the variation of FIGS. 22A-22B.

In the probe of FIGS. 22A-22B, the needle assembly 1215 is configured for ballistic advancement from the non-extended position of FIG. 22A to the extended position of FIG. 22B. As can be seen in FIG. 22A, a fluid vaporization chamber 1225 is provided in the body 1210 proximal to the needle assembly 1215 and an electrode arrangement comprising opposing polarity electrodes 1240A and 1240B is provided to delivery energy to the fluid vaporization chamber 1225. As can be seen in FIG. 22A, the needle assembly 1215 includes an O-ring 1228 is a fluid seal in cylindrical bore 1224. The electrodes 1240A and 1240B are operatively coupled to an energy source 1250 and a controller 1255 for the delivery of energy to fluid 1252 in chamber 1225. The fluid 1252 can be sterile water in the energy delivery from the energy source 1250 will be sufficient to explosively vaporize the fluid 1252 to thereby instantly accelerate the needle assembly 1215 distally in the probe body. It can be understood that the phase transition of the fluid 1252 from a liquid to a gas can increase the fluid volume by 1000× or more to thereby move the needle assembly 1215 to the extended position of FIG. 22B. The probe body 1210 further can have a pressure relief valve (not shown) communicating with the vaporization chamber 1225 to prevent overpressures therein. FIG. 22B illustrates the needle 1205 of FIG. 22A in an extended position following the explosive vaporization of fluid 1252 in the vaporization chamber 1225 to move the needle from the non-extended position to the extended position.

Still referring to FIGS. 22A-22B, the controller 1255 is configured to allow the operator to select among a plurality of lower and higher energy levels that can be delivered from the energy source 1250 to the fluid 1252 in the vaporization chamber 1225 wherein each energy level will cause a different amount of vapor expansion which in turn provides for a selected, different acceleration rate of the needle 1205 into tissue. Such differing acceleration rates are useful depending on the selection of needle length and needle gauge as well as the characteristics of the targeted tissue, such as tissue density and different tissue layers that may need to be penetrated.

In general, a method of needle injection responding to the invention comprises providing an injector body that carries a distal needle that is movable between a non-extended position and an extended position relative to the injector body, wherein a fluid-filled chamber is provided in the injector body proximate to said needle, and causing explosive vaporization of a fluid in said fluid-filled chamber to thereby move the needle from the non-extended position to the extended position. While the embodiment of FIGS. 22A-22B show an electrical source coupled to an electrode arrangement to cause the vaporization of the fluid 1152 in a chamber, it should be appreciated that any energy source may be used for example an RF source, a laser source, a microwave source, an ultrasound source or a resistive heating mechanism.

Figures 23A, 23B:
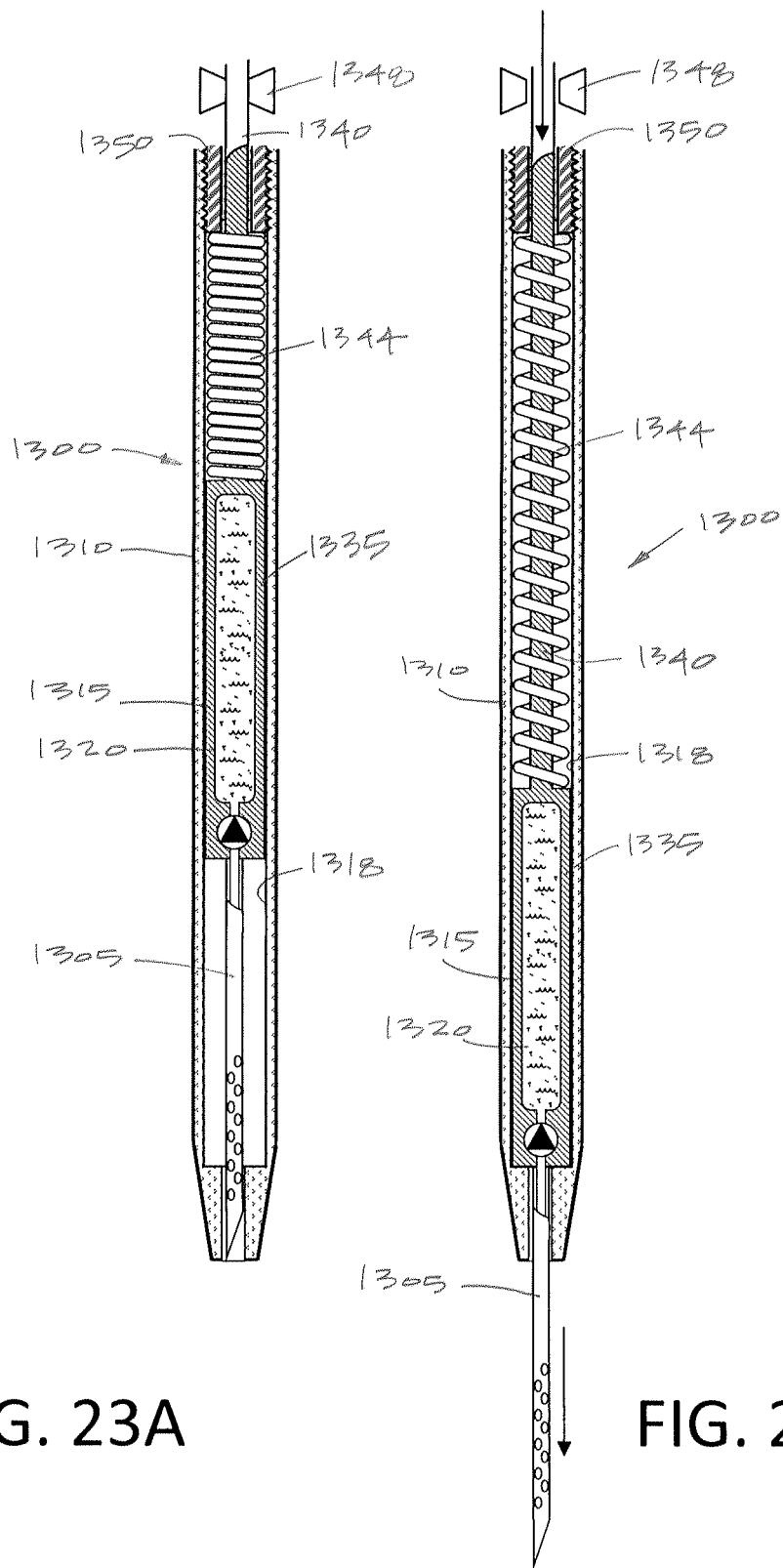
FIG. 23A is a view of the working end of another probe similar to that of FIG. 21A with a distal needle in a non-extended position in a spring mechanism adapted for advancing the needle two and extended position from the non-extended position together with an adjustment mechanism that can adjust the spring mechanism to provide a plurality of needle acceleration rates.
FIG. 23B illustrates the needle of FIG. 23A in an extended position following the release of a walking mechanism that allows the spring mechanism to move the needle from the non-extended position to the extended position.

FIG. 23A is a view of the working end 1300 of another ablation probe which is similar to that of FIG. 22A with a distal needle 1305 in a non-extended position. In this variation, a spring mechanism is adapted for advancing the needle 1305 to the extended position from the non-extended position together with an adjustment mechanism that can adjust the spring mechanism to provide a plurality of needle acceleration rates.

In the variation of FIGS. 23A-23B, the probe body 1310 again carries a movable needle assembly 1315 that carries an interior chamber 1320 for containing the subcritical water. The needle assembly 1315 is movable in a cylindrical bore 1318 in the probe body 1310. For clarity in describing the needle advancement mechanism, FIGS. 23A-23B do not illustrate the heating mechanism for providing the subcritical water in filled chamber 1320, which can be any of the previously described heating mechanisms.

FIGS. 23A-23B further show that the housing component 1335 of the needle assembly 1315 that surrounds the interior chamber 1320 is coupled to an elongated shaft 1340 that extends proximally to a handle portion (not shown) of the probe body 1310. The elongated shaft 1340 can be flexible or rigid depending on the configuration of the probe body 1310. As can be seen in FIG. 23A, a helical spring 1344 is disposed around the shaft 1340 in a compressed condition and is adapted to urge the needle assembly 1315 in the distal direction when tension on the helical spring 1344 is released. It can be understood that the shaft 1340 in a proximal portion of the probe 1310 has can have a locking-release mechanism indicated schematically at 1348 for locking the shaft 1340 in a cocked position as shown in FIG. 23A. Any type of lock-release mechanism 1348 can be used to retain and release the shaft 1340. FIG. 23B shows the needle assembly 1315 and shaft 1340 after the lock-release mechanism 1348 has released the shaft 1340 to thereby allow the helical spring 1344 to urge the needle assembly 1315 to the needle-extended position. In this variation, it can be understood that the needle assembly 1315 could be returned to, and locked in, the cocked position of FIG. 23A for one or more additional uses. In such a variation, the needle assembly 1315 that have multiple interior chambers in release mechanism as shown in the variation of FIG. 14. In contrast, the previous embodiment of FIGS. 22A-22B which is a ballistic needle advancement mechanism is adapted for a single use.

In another aspect, still referring to FIGS. 23A-23B, the probe body 1310 includes a spring adjustment mechanism which can comprise a threaded body 1350 or any other movable body that can alter the spring tension when the needle assembly 1315 and spring 1344 are moved to the non-extended, or cocked, position of FIG. 23A. It can be understood that the threaded body 1350 can move longitudinally within the probe body 1310 to change the compressed length of the helical spring 1344 which thereby in turn can allow for adjustment of the acceleration rate of the needle assembly 1315 when the lock-release mechanism 1348 releases the needle assembly 1315 to penetrate the needle 1305 into tissue. FIG. 23B illustrates the needle 1305 in an extended position following the release of the lock-release mechanism 1348 that allows the spring 1344 to move the needle from the non-extended position to the extended position.

FIGS. 24-26B illustrate another system 1400 that is similar to previous systems in some aspects in that an ablation device or stick 1405 is provided with a first energy source 1410 for providing a subcritical critical liquid 1412 in an interior chamber 1415 of the shaft portion 1416 of the ablation stick 1405 that communicates with a flow outlet 1420 in a needle portion 1422 of the device. However, the system 1400 of FIG. 24 differs from previous embodiments in that the ablation stick 1405 is adapted to deliver greater ablative energy to tissue by ejecting such a subcritical liquid media from the flow outlet 1420 of the needle 1422 and contemporaneously coupling electrical energy from a second energy source 1425 to the media flow to thereby ionize such a media flow wherein the ionized media flow then can deliver enhanced ablative energy to tissue in a targeted site.

Figure 24:
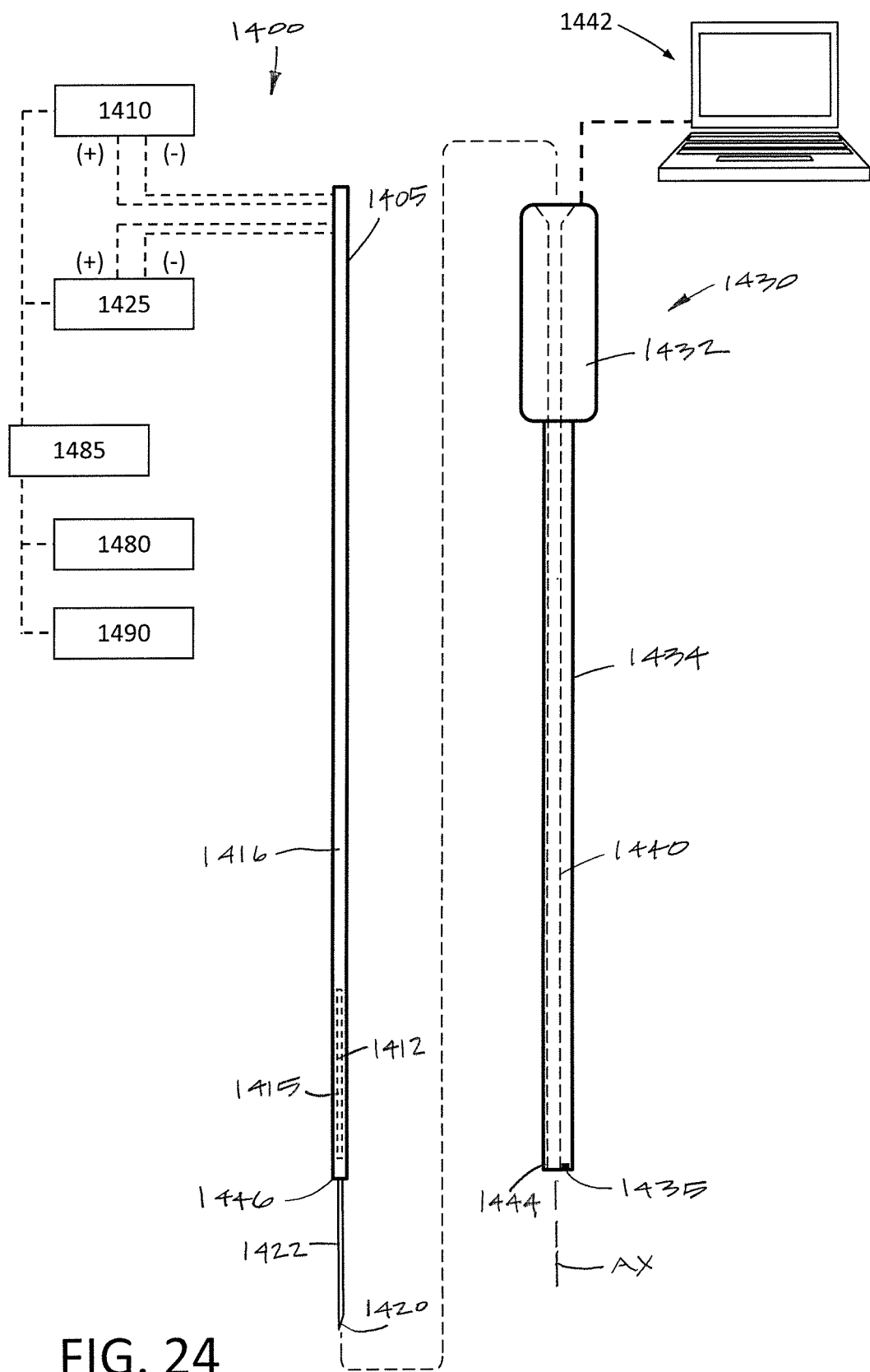
FIG. 24 is a schematic view of another system variation that includes an ablation stick and endoscope where the ablation stick again has an interior chamber configured for containing subcritical water, a valve mechanism for releasing subcritical water from the interior chamber to provide a media flow through a flow outlet in a needle member as in previous embodiments, and further includes a second energy source coupled to an electrode arrangement adapted to ionize the media flow from the flow outlet to enhance energy delivery to ablate targeted tissue.

Still referring to FIG. 24, the system 1400 furthers include an endoscope 1430 that can be similar to any endoscopes illustrated in previous embodiments. In FIG. 24, the endoscope 1430 is shown in a rigid version with a handle portion 1432 and elongated shaft 1434 that carries a distal imaging sensor 1435. In another variation (not shown), the endoscope can be configured with an articulating distal portion as described above. The endoscope 1430 has a working channel 1440 for receiving the ablation stick 1405 similar to previously described embodiments. A video display or monitor 1442 of any type can be coupled to the endoscope 1430. The endoscope 1430 also can carry LEDs as described previously as well as one or more flow channels for providing irrigation to and from a treatment site as is known in the art.

In the variation shown in FIG. 24, the ablation stick 1405 consists of a basic, simple configuration wherein the physician would introduce or stab the needle portion 1422 into a targeted tissue site under endoscopic vision as might be done in a treatment of submucosal fibroids or similar targeted tissue in a body lumen or body cavity. In other variations described below, the distal portion of the ablation stick 1405 may include a spring mechanism for causing the needle portion 1422 to penetrate targeted tissue.

In one variation, the distal end 1444 of the working channel 1440 can include features that cooperate with the distal end 1446 of the shaft portion 1416 of the ablation stick 1405 for maintaining or locking the shaft portion 1416 of the ablation stick in relation to the distal end of the endoscope 1430. Such a feature can comprise a simple stop collar to prevent the shaft 1416 of the ablation stick 1405 from extending outwardly from the endoscope 1430 while permitting the needle portion 1420 to be advanced. In another variation, the threaded mechanism may be used to lock the distal end 1446 of the shaft portion 1416 into the distal end 1444 of the working channel 1440.

Figure 25A:
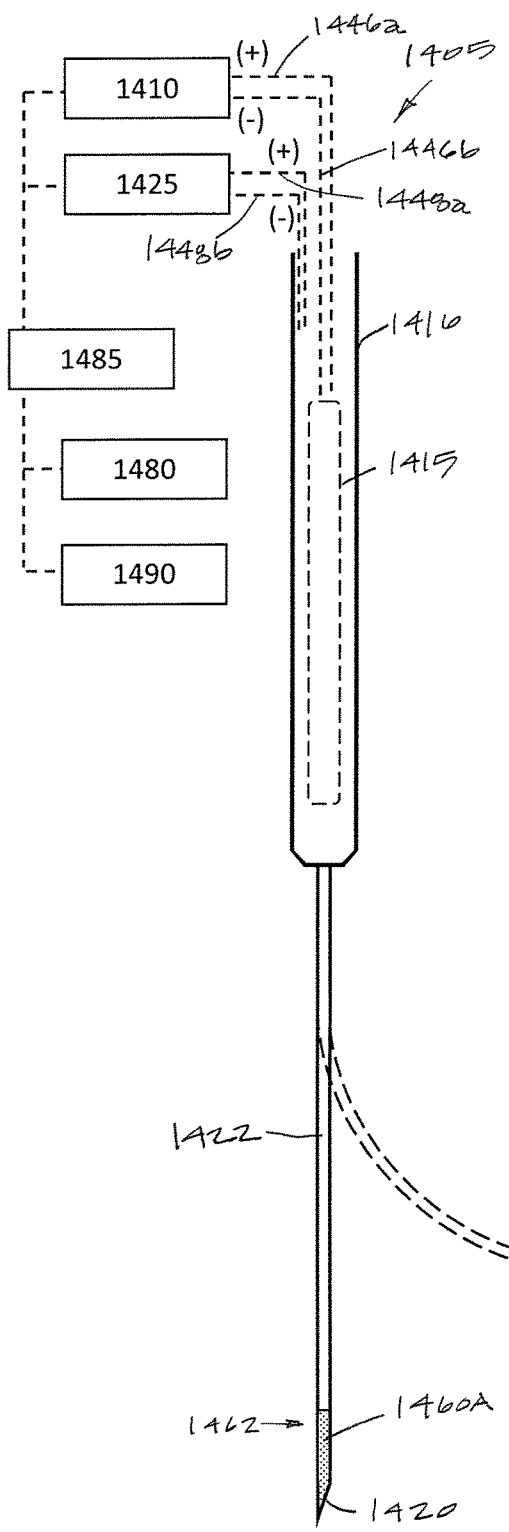
FIG. 25A is an enlarged view of the distal region of the ablation stick of FIG. 24 showing the interior chamber, the valve, and a flexible polymer needle member.

Now referring to FIGS. 24 and 25A, it can be seen that ablation device or stick 1405 again includes an elongate needle portion 1422 which can have any suitable length ranging from about 2 mm to 50 mm for penetrating targeted tissue. In the variation shown in FIG. 25A, the elongated needle portion 1422 can be a rigid needle member or a flexible needle member of a polymer such as PEEK which extends distally from the shaft portion 1416 of the ablation stick 1405. A flexible needle portion 1422 shown in FIG. 25A can thus be adapted to be advanced through a curved channel in an endoscope or other introducer member to advance the needle portion 1422 at an angle relative to the axis AX of such an endoscope 1430 or introducer (FIG. 24) as will be described in later embodiments.

Figure 25B:
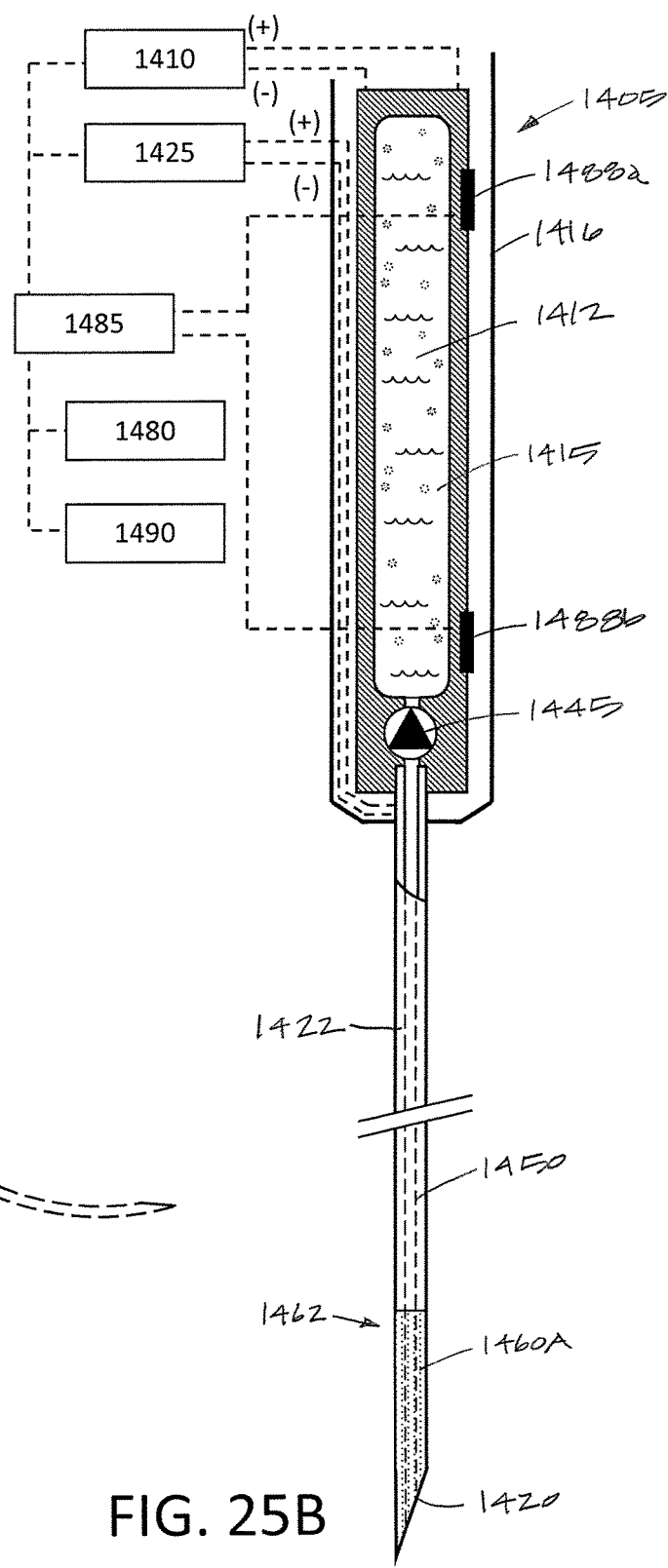
FIG. 25B is an enlarged sectional view of the distal region of the ablation stick of FIG. 25B showing the interior chamber, temperature sensors coupled to the interior chamber, the valve, and a electrode arrangement carried at the distal end of the needle member.

Referring to FIGS. 25A and 25B, the needle portion 1422 has a single flow outlet 1420 that is provided in the distal-most tip of the needle portion 1422. However, it should be appreciated that other variations can be provided with a plurality of ports disposed around the distal end of the needle portion 1422 as described previously.

As can be seen in FIGS. 24, 25A and 25B, the shaft portion 1416 of the ablation stick 1405 includes an interior chamber 1415 that is configured to contain the subcritical liquid 1412 until the valve 1445 of any suitable type is opened as described previously. The first electrical source 1410 is configured to deliver energy through electrical leads 1446a and 1446b to the interior chamber 1415 to provide the subcritical liquid as described previously.

Figures 26A, 26B:
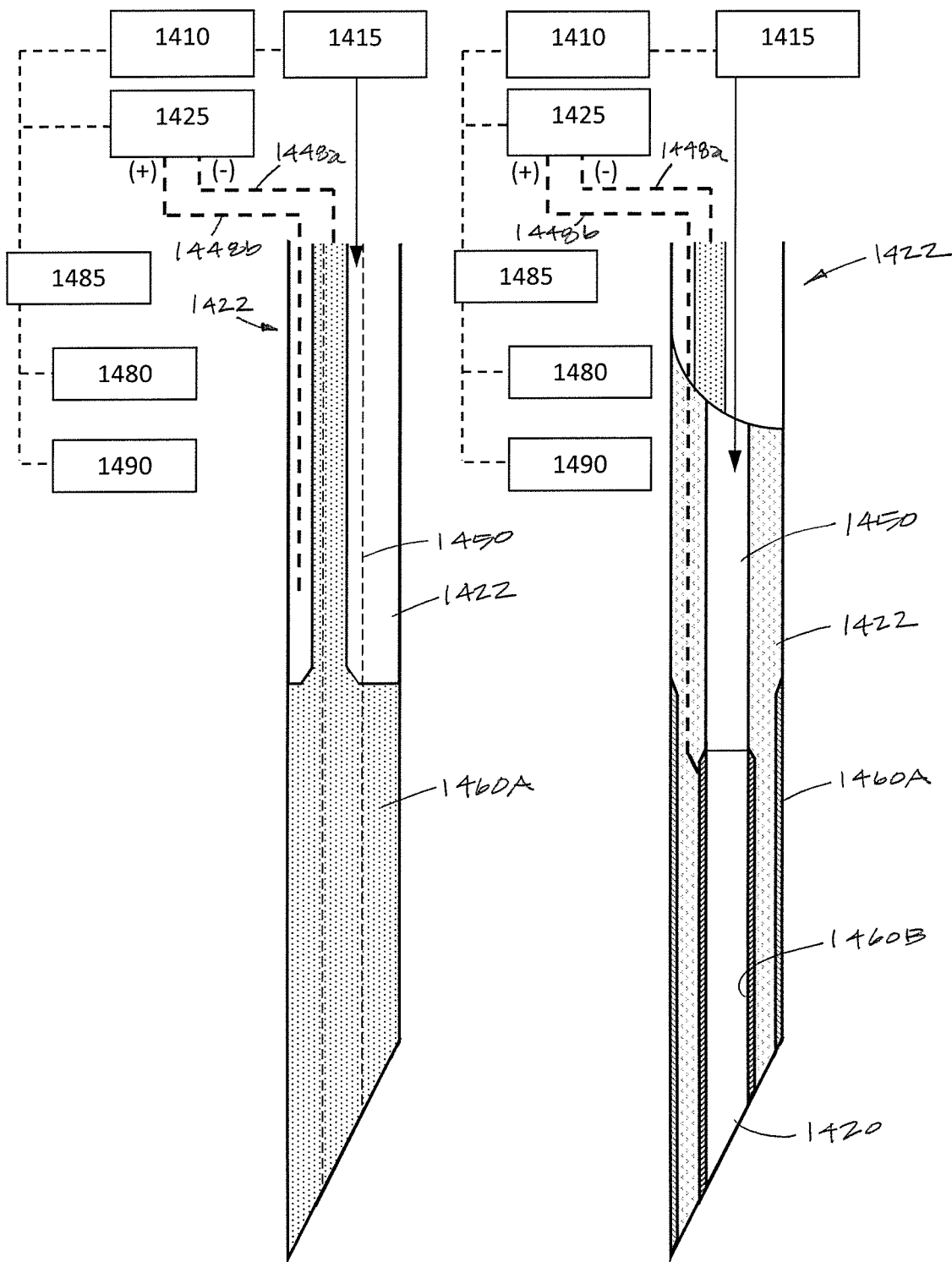
FIG. 26A is a further enlarged view of the distal and of the needle member showing a first electrode.
FIG. 26B is a sectional view of the distal and of the needle member FIG. 26A showing the first and second electrodes carried by the needle tip.

Still referring to FIGS. 24-25B, the second energy source 1425 is configured to deliver electrical energy to the sub-critical media flow exiting the flow outlet 1420 of channel 1450 in the needle portion 1422. More in particular, FIGS. 25B, 26A and 26B shows the second independent electrical source 1425 and electrical leads 1448a and 1448b that extend through the shaft portion 1416 of the ablation stick 1405 to first and second electrodes 1460A and 1460B carried by the distal region 1462 of the needle portion 1422 (FIGS. 26A-26B). In the elevational view of FIG. 26A, it can be seen that the first electrode 1460A comprises a conductive plating carried on the exterior of a dielectric needle portion 1422. This electrode 1460A can comprise an electroless plating or a thin-wall conductive sleeve. The sectional view of FIG. 26B shows that the second electrode 1460B is disposed around the surface of the interior flow channel 1450 of the needle portion 1420 and consists of a similar conductive plating or thin-wall sleeve. The electrical leads 1448a and 1448b that extend to the first and second electrodes 1460A and 1460B can also comprise conductive plating elements as are known in the art. Thus, it can be seen how the spaced apart first and second polarity electrodes 1460A and 1460B can deliver electrical energy to flow media that exits the distal flow outlet 1420 of the flow channel 1450 in the needle portion 1422.

Figure 27:
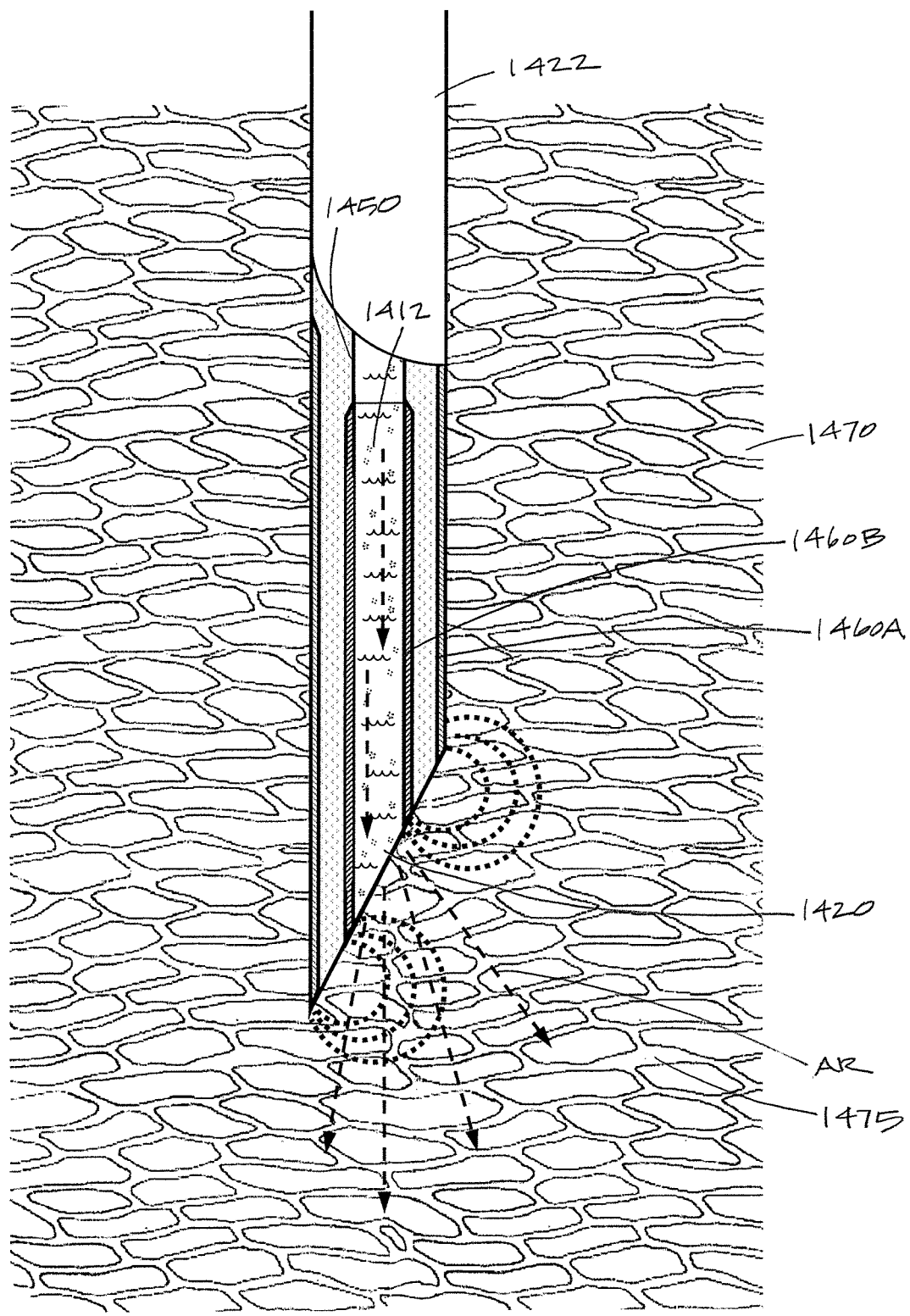
FIG. 27 is a schematic view the needle tip of FIG. 20 6B in tissue illustrating a flow of subcritical media through the needle member and energy being delivered from electrode arrangement to ionize the media flow outwardly from the flow outlet.

FIG. 27 next illustrates a cut-away view of the distal portion the needle portion 1420 similar to that of FIG. 26B embedded in the targeted tissue site 1470 with a flow of subcritical liquid media 1412 through the interior flow channel 1450 in the needle portion 1422 until such media exits the flow outlet 1420 and electrical energy is delivered to said media flow by the spaced apart electrodes 1460A and 1460B to thereby ionize such a media flow. The arrows AR then illustrate the ionized media flow outward into the targeted tissue 1470 which generally may propagate in extracellular spaces 1472 which are shown schematically between cellular structures 1475 (not-to-scale). By this means, the heat from the ionized media flow as well as the energy delivered by actively moving ions of the ionized flow can enhance the ablative energy applied to the targeted tissue 1470.

In the operation of the ablation stick 1405 of FIGS. 24-26B, it can be understood that the physician initially positions the needle portion 1422 in the targeted site, and prior to or subsequent to such positioning of the needle portion activates the first electrical source 1410 with a switching mechanism indicated at 1480 which is typically coupled to a controller 1485. Such a switch mechanism 1480 can be disposed on the ablation stick 1405 or in the electrical conduit coupling the electrical source 1410 to the ablation stick. Further, in one variation, one or more temperature sensors 1488a and 1488b (FIG. 25B) are positioned about the interior chamber 1415 to monitor and control fluid temperatures within the interior chamber 1415. Such temperature sensors 1488a and 1488b are configured to send signals to the controller 1485 which then can modulate energy delivery from the first electrical source 1410 to maintain over time a targeted temperature in the interior chamber 1415 to thereby provide the subcritical liquid at the desired temperature and pressure as described previously. Further, the controller 1485 may be adapted to control and maintain the temperature at a two or more preselected temperatures to thus provide different amounts of delivered energy.

As can be understood from FIGS. 24-26B, a second switch mechanism 1490 is coupled to the controller 1485 and ablation stick 1405 which is adapted to activate the second electrical source 1425 deliver electrical energy to electrodes 1460A and 1460B to ionize the media flow from outlet 1420 in the needle portion 1422. In one variation, the valve 1445 and the second switch mechanism 1490 are controlled by the controller 1485 to energize the electrodes 1460A and 1460B contemporaneously with the opening of the valve 1445, or energizing the electrodes 1460A and 1460B slightly before the opening of the valve 1445. The valve 1445 can be any of the types described previously or can be a specialized pressure relief valve.

Figures 28A, 28B:
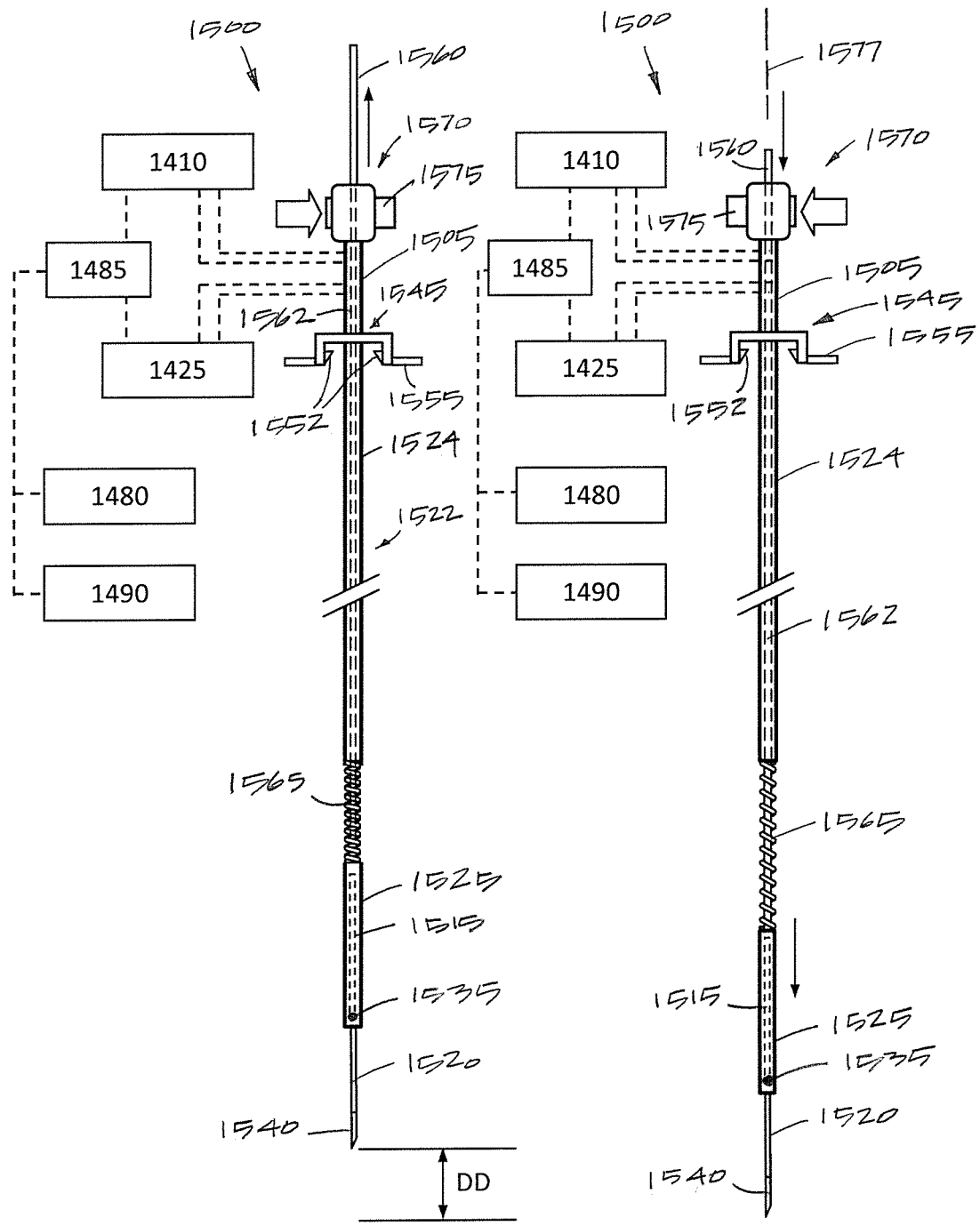
FIG. 28A is an illustration of another variation of ablation stick that is similar to the embodiment shown in FIG. 24 except that the ablation stick further includes a spring mechanism for advancing the needle member into tissue upon release of a lock-release mechanism with a needle member is in a cocked position.
FIG. 28B is another variation view of the ablation stick of FIG. 28A after actuation of the lock-release mechanism to thereby allow this spring to advance the needle member in the distal direction.

FIGS. 28A-30B illustrate another embodiment of an ablation system 1500 with an ablation stick or device 1505 with an interior chamber 1515 configured to provide subcritical liquid and electrodes as in the device of FIGS. 24-26B for ionizing a media flow from the stick. The ablation stick 1505 thus is similar to that of the ablation stick 1405 of FIGS. 24-26B, except that the device 1505 of FIGS. 28A and 28B includes a spring mechanism for advancing the needle portion 1520 an extension distance DD into a targeted tissue site. As can be seen in FIG. 28A, the ablation stick 1505 has a shaft 1522 including a proximal shaft portion 1524 and a spring-loaded distal shaft portion 1525 wherein the proximal shaft portion 1524 can be maintained in a fixed position relative to endoscope 1530 (FIG. 30A) or an introducer. The spring-loaded distal shaft portion 1525 then can be actuated to project distally and outwardly from a working channel 1532 in the endoscope 1530 (see FIG. 30A). As can be seen in FIG. 28A, the spring-loaded distal shaft portion 1525 carries the interior chamber 1515 for providing subcritical liquid, the valve 1535 and needle portion 1520.

A first electrical source 1410, a second electrical source 1425 and controller 1485 are shown in FIGS. 28A-28B and 30A-30B which are adapted to function the same manner as described previously. More in particular, referring to FIG. 28A, it can be seen that the ablation stick 1505 again has first electrical source 1410 operatively coupled to interior chamber 1515 for providing subcritical liquid 1412. The ablation stick 1515 shown in FIGS. 28A-28B and 30A-30B further has second electrical source 1425 which is adapted to energize an electrode arrangement 1540 in the distal tip of needle member 1520 for ionizing the media flow as described previously.

In FIGS. 28A and 30A it can be seen that the ablation stick 1505 further includes an engagement mechanism or latch connector 1545 for connecting the proximal shaft portion 1524 of the ablation stick 1505 to handle 1548 of the endoscope 1530. Such a connector is shown as a flexible snap-fit mechanism that has tab elements 1552 that snap into groove 1554 in the endoscope handle 1548. The tab elements 1555 can be flexed to remove the ablation stick 1505 from the endoscope handle 1548.

Figure 29A:
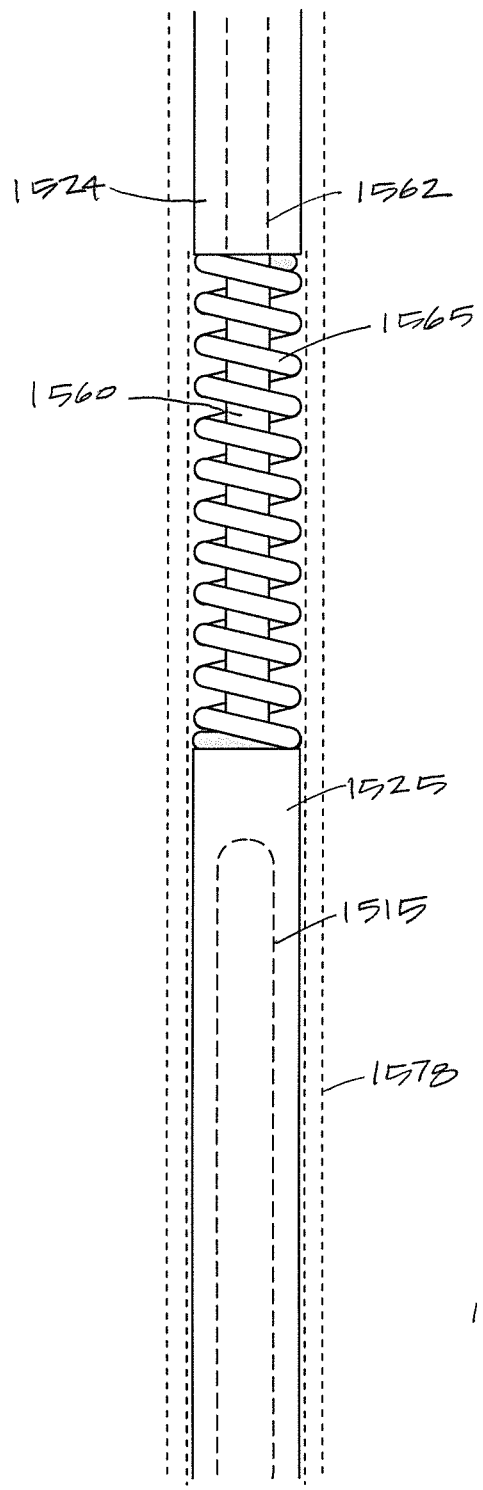
FIG. 29A is an enlarged view of the central portion of the ablation stick of FIG. 28A showing the spring in a cocked position.
Figure 29B:
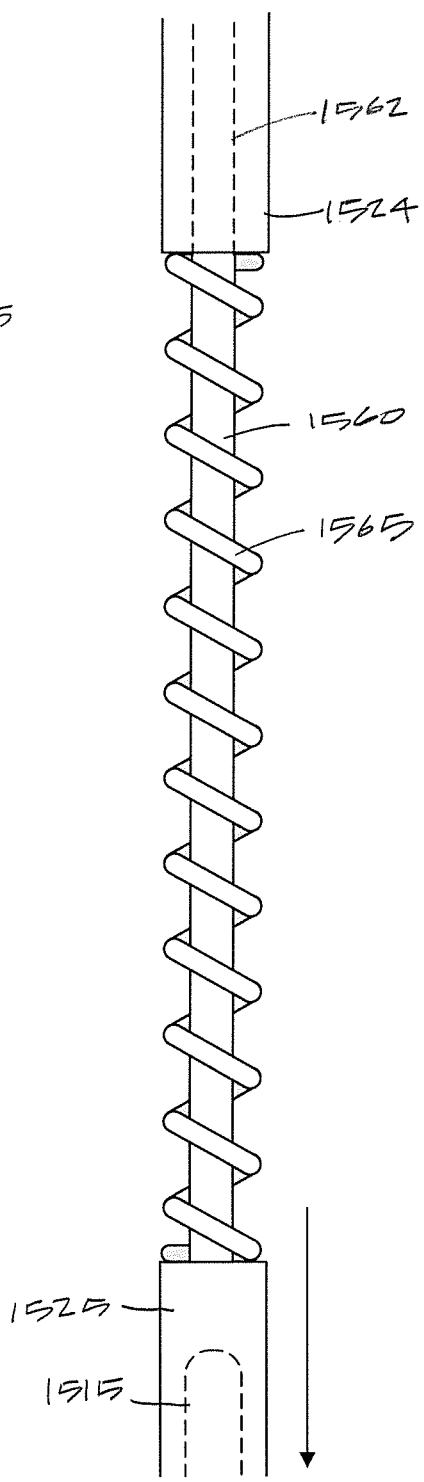
FIG. 29B is an enlarged view of the central portion of the ablation stick of FIG. 28B after actuation of the lock-release mechanism and release of the spring to advance the needle member in the distal direction.

In FIGS. 28A and 29A, it can be seen that distal shaft portion 1525 which carries the interior chamber 1515 is coupled to an elongate extension member 1560 that extends through bore 1562 in the proximal shaft portion 1524. In FIG. 28A, the spring 1565 is compressed as the extension member 1560 is moved proximally and a lock-release mechanism 1570 coupled to the proximal end 1572 of proximal shaft portion 1524 is used to lock the extension member 1560 in a cocked position. The lock-release mechanism 1570 can comprise a moveable locking element 1575 that can be finger-actuated to move transversely in a first direction relative to axis 1577 of the extension member 1560 to thereby grip and engage the extension member 1560 as illustrated in FIG. 28A. FIGS. 28B and 30B illustrate the locking element 1575 after being actuated transversely in a second direction relative to axis 1577 to thereby release its grip on extension member 1560 and thereby cause the needle portion 1520 to spring outwardly or the distal direction to thereby penetrate tissue. As can be seen in FIGS. 28B, 29B and 30B, the spring 1565 is released from its compressed position of FIGS. 28A, 28B and 29B at moves to a repose extended position that the projects the needle portion 1520 distally. FIG. 29A shows that a thin outer sleeve 1578 can be provided to cover the spring 1565 while still allowing movement of the distal shaft portion 1525.

FIGS. 30A and 30B show the assembly of the ablation stick 1505 of FIGS. 28A-28B with the endoscope 1530 showing a mode of operation of the system. In FIG. 30A, it can be seen that the latch connector 1545 has coupled the ablation stick 1505 to handle 1548 of endoscope 1530 to thereby provide a fixed relationship between the ablation stick 1505 and the endoscope. It should be appreciated again that the endoscope can be a rigid endoscope or an elongated flexible or articulating endoscope. FIG. 30B shows the release of the lock-release mechanism 1570 which allows the needle portion 1520 to be advanced outwardly from the distal end 1582 of the endoscope 1530 to penetrate tissue an extension distance of DD.

Figure 31A:
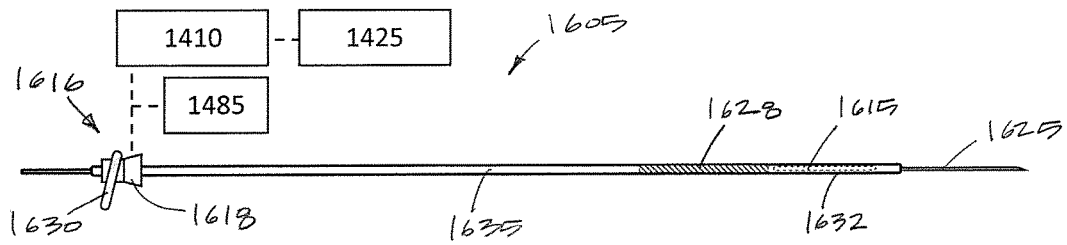
FIG. 31A is an illustration of another variation of ablation stick that is similar to the embodiment shown in FIG. 30A with a latch mechanism for coupling the ablation stick to an endoscope.
Figure 31B:
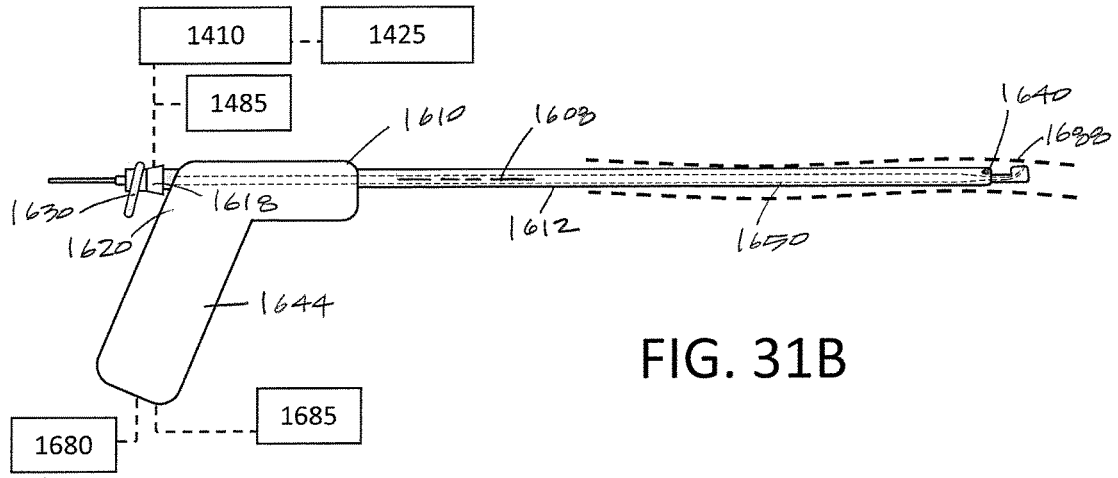
FIG. 31B is a side view of another variation of endoscope with the ablation stick of FIG. 31A coupled thereto, where the endoscope has a elongated shaft and carries a distal imaging sensor together with an extension portion with a curved needle channel for directing a flexible polymer needle outwardly at an angle relative to the axis of the endoscope.
Figure 31C:
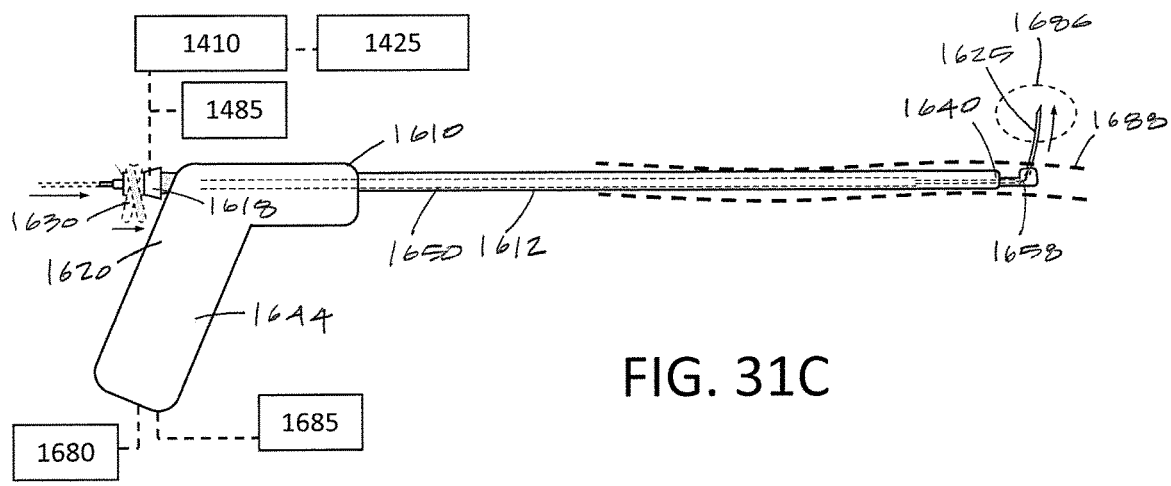
FIG. 31C is another view of the endoscope of FIG. 31 B with a flexible needle having been actuated and extending outwardly from the curved needle channel.
Figure 32:
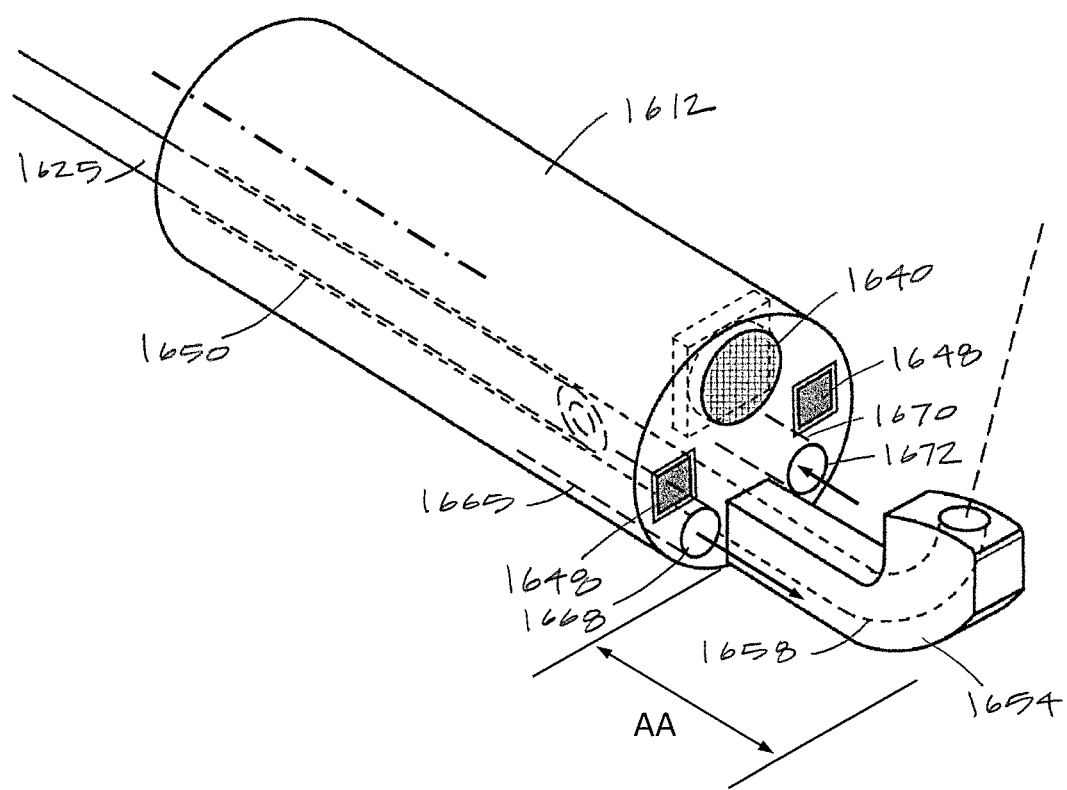
FIG. 32 is a perspective view of the distal end of the endoscope of FIG. 31B showing the imaging sensor, LEDs, the curved needle channel, an inflow channel and an outflow channel for irrigating a treatment site.

Now turning to FIGS. 31A-31C and 32, another variation of ablation stick 1605 and specialized introducer and endoscope 1610 is shown that is adapted to penetrate the needle member into tissue at an angle relative to the axis 1608 of the endoscope shaft 1612. FIG. 31A illustrates the ablation stick 1605 separate from the endoscope 1610 wherein the ablation stick is similar to the embodiments described previously, with first and second energy sources 1410 and 1425 for providing a subcritical liquid in an interior chamber 1615 for ejecting from a needle member 1625. The ablation stick 1605 has a proximal portion 1616 that includes a latch mechanism 1618 for latching onto the handle 1620 of the endoscope 1610. The ablation stick in this variation has an elongated flexible needle member 1625 that is spring-loaded by spring 1628 of the type described previously. A lock release mechanism 1630 is provided to release the distal portion 1632 of the shaft 1635 of the ablation stick 1605 allowing the needle member 1625 to penetrate tissue. Typically, the endoscope 1610 is adapted for single use and carries an imaging sensor 1640 in its distal end as described in previous embodiments (see FIG. 32). The endoscope 1610 has a handle or grip 1644 that can be a pistol grip or an in-line grip that is coupled to the endoscope shaft 1612. The endoscope shaft again carries a distal LEDs 1648 and a channel 1650 which accommodates the ablation stick 1605 and needle member 1625. As can be seen best in FIG. 32, the distal end of the endoscope shaft 1612 includes an extension member 1654 that extends distally a distance AA beyond the imaging sensor 1640. The extension distance AA may range from about 5 mm to 20 mm and more often is between about 8 mm and 15 mm. In FIG. 32, it can be seen that the channel 1650 has a distal portion comprising a curved needle channel 1658 that is adapted to receive and direct the flexible needle 1625 to extend outwardly at a selected angle that can range from 30° to 90° relative to the axis 1660 of the endoscope shaft 1612. Thus, as can been understood from FIGS. 31C and 32, the positioning and extension of the needle 1625 into tissue is within the field of view of the imaging sensor 1640.

Referring to FIGS. 31B, 31C and 32, the endoscope shaft 1612 also is adapted to provide fluid flows to a treatment site with a fluid inflow channel 1665 extending to port 1668 and a fluid outflow channel 1670 extending proximally from outflow port 1672. As can be seen in FIG. 31B, a fluid source 1680 is adapted to provide fluid inflows and can comprise a saline bag or other suitable fluid source. Such a fluid inflow can be provided by gravity flow or by a pump system as is known in the art. Similarly, the fluid outflows can optionally be assisted by a pump and collected in reservoir 1685.

FIG. 31B shows the ablation stick 1605 inserted into the endoscope 1610 with the latch mechanism 1618 engaging the endoscope. In FIG. 31B, the ablation stick 1605 is in the needle-cocked position wherein the spring 1628 is compressed and ready for release to inject the needle member 1625 into tissue. FIG. 31B schematically shows the endoscope shaft 1612 introduced in a treatment site 1686 body lumen 1688 in phantom view. FIG. 31C shows the lock-release mechanism 1630 being actuated to release the needle member 1625 to penetrate targeted tissue 1690. As can be seen in FIG. 31C, the elongated flexible needle 1625 is advanced outward from the distal curve channel 1658 of the endoscope 1610 and extension member 1654.

Of particular interest, referring to FIGS. 31B, 31C and 32, the endoscope shaft 1612 has an insertion profile that is less than 7 mm in diameter and often less than 6 mm in diameter and any suitable length for introduction into a body lumen. In some cases, the diameter can be less than 5 mm in diameter which is made possible by the small size of the digital imaging sensor 1640. In such variations, the imaging sensor 1640, the LEDs 1648, the inflow and outflow channels 1665 and 1670 all can be accommodated together with the needle channel 1658 in the small diameter endoscope shaft 1612.

Thus, a method corresponding to the invention is shown in FIG. 33 and comprises (i) introducing an endoscope shaft with a distal imaging sensor through a body lumen to a site, wherein the insertion profile of the endoscope shaft is less than 7 mm in cross section and the endoscope shaft has a channel therein with a curved distal section for directing a flexible needle advanced therethrough; (ii) inserting a injector into the channel, the injector having an interior chamber communicating with a flow outlet in a needle member, the interior chamber containing a pre-selected volume of conductive liquid; (iii) observing the site with the imaging sensor and actuating the injector to advance the needle member through the curved channel and the lumen wall into targeted tissue; and (iv) ejecting subcritical liquid from the interior chamber to provide a subcritical liquid flow through the flow outlet and coupling electrical energy to said flow to ionize the flow wherein the ionized flow delivers ablative energy to the targeted tissue.

As described above, an energy source for providing the subcritical liquid in an interior chamber of an ablation stick of the types shown in FIGS. 1B, 2, 4A, 5, 10A, 11, 14, 16A, 22A and 23A can be a source of stored energy such as a battery, capacitor or supercapacitor.

Figure 34:
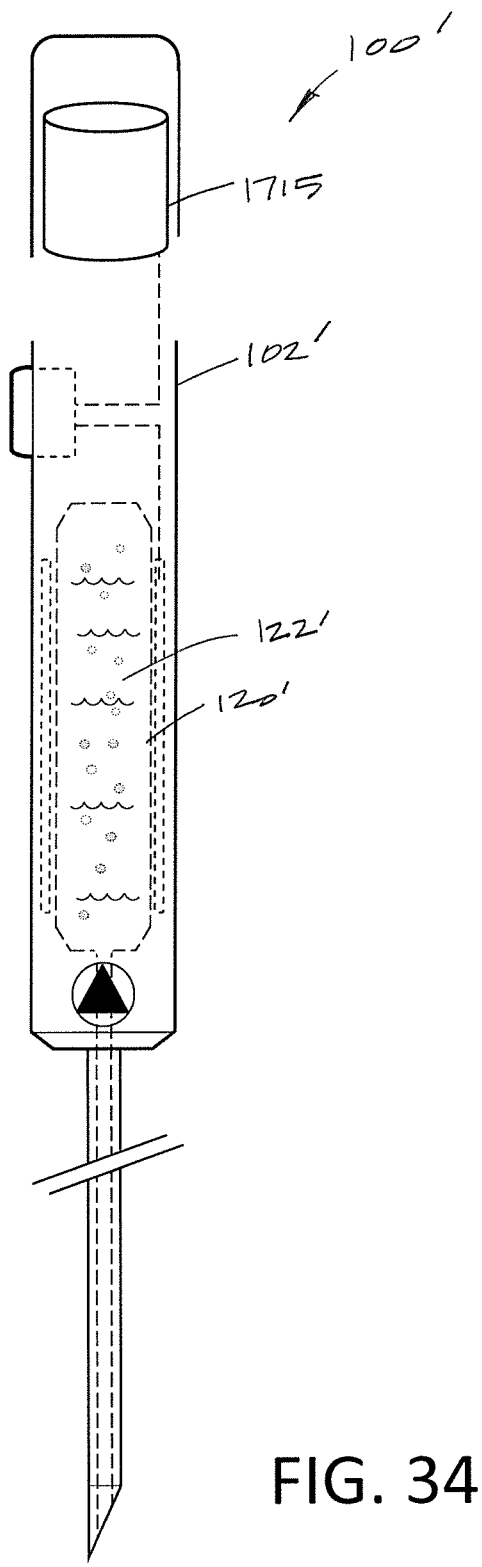
FIG. 34 is another variation of an ablation probe similar to that of FIG. 2 that carries a battery or capacitor in a proximal shaft portion of the probe for providing subcritical liquid in an interior chamber of the probe.

FIG. 34 illustrates an ablation stick 100' with interior chamber 120' that is similar to the embodiment of FIG. 2 except that the shaft portion 102' of the ablation stick of FIG. 34 carries a stored electrical energy component 1715 which can comprise at least one battery, capacitor, supercapacitor or the like. It has been found that the power requirements for providing subcritical liquid 122' in a small volume in interior chamber 120' is quite small and can be provided by a such a battery, capacitor or supercapacitor.

Figures 35, 36:
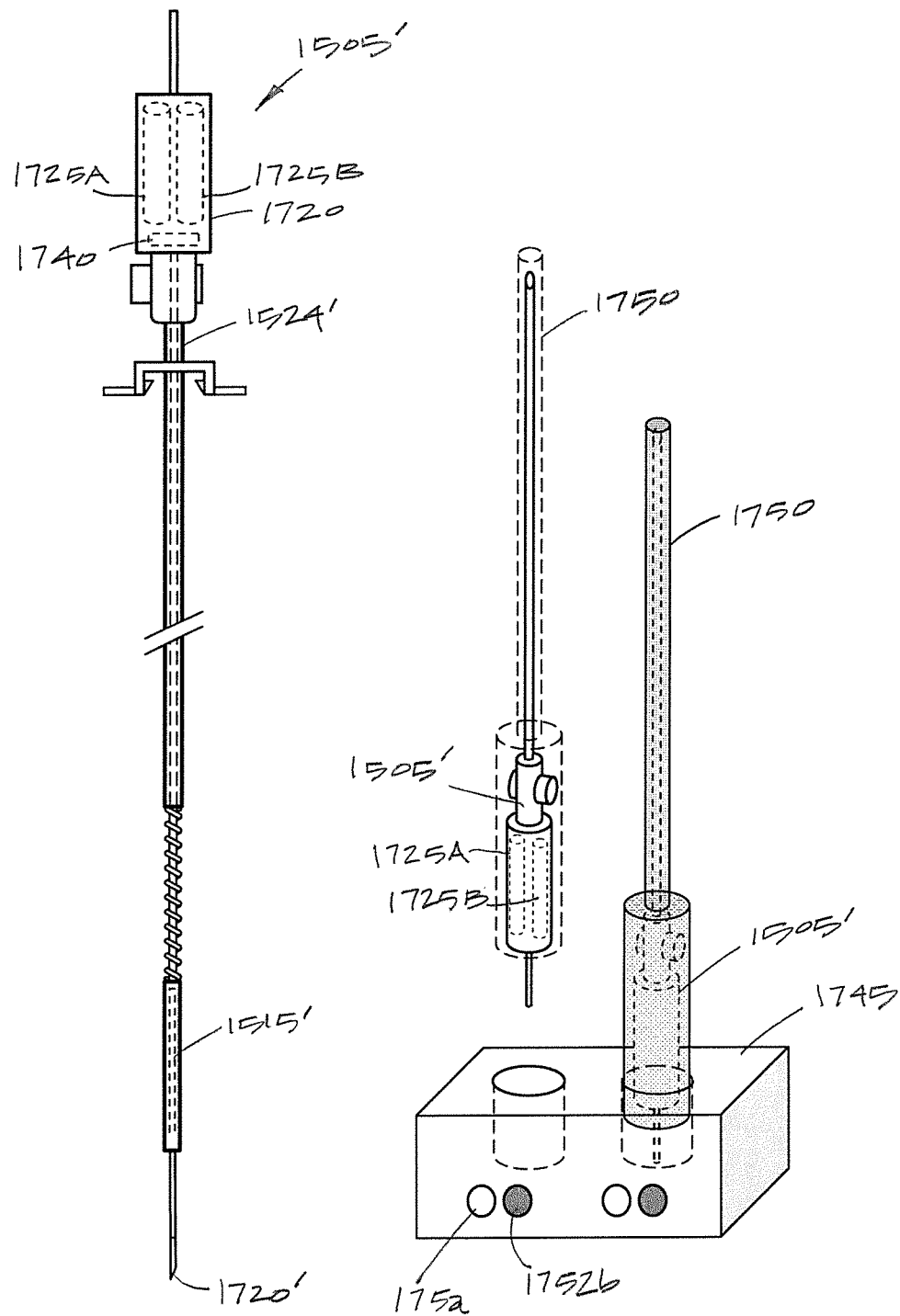
FIG. 35 is another variation of an ablation probe similar to that of FIG. 28A that carries first and second batteries or capacitors in a proximal portion of the probe for (i) providing subcritical liquid in an interior chamber of the probe and (ii) providing electrical energy for ionizing a media flow outward from a flow outlet in a needle member of the probe.
FIG. 36 is a schematic view of a base station for charging a probe of the types shown in FIGS. 34 and 35.

FIG. 35 illustrates another variation ablation stick 1505' that is similar to that of FIG. 28A except that the proximal shaft portion 1524' includes a housing 1720 that carries first and second stored energy components, 1725A and 1725B, that again can comprise one or more batteries, capacitors or super capacitors. In this variation, the housing 1720 also can carry a controller microchip 1740 for controlling energy delivery from the stored energy components, 1725A and 1725B, during operation. In the ablation stick 1505' shown in FIG. 35, the first stored energy component 1725A is adapted to deliver energy to the interior chamber 1515' to provide the subcritical liquid therein. The second stored energy component 1725B is configured to be actuated to deliver electrical energy to the electrode arrangement about the flow outlet 1720' to thereby ionize the media flow exiting the flow outlet 1420' as described previously (see FIGS. 26A-27). The proximal portion of the ablation stick 1505' also can carry one or more actuators or switches (not shown) coupled to the controller microchip 1740 and/or the stored energy components, 1725A and 1725B to actuate the system for use in a procedure.

The 36 illustrates the ablation stick of FIG. 35 in preparation for use when at least one of the stored energy components, 1725A and 1725B, such as a capacitor or super capacitor, is charged by a base station 1745 in which the ablation stick is docked. As can be seen in FIG. 36, the ablation stick 1505' may be housed for convenience and safety in a thin protective sheath 1750. The base station or docking station 1745 can further include indicators, such as LEDs 1752a and 1752b, that indicate whether the first and second stored energy sources 1725A and 1725B are charging or have a complete charge and thus the probe is ready for use in a medical procedure. It should be appreciated that such a docking station 1745 can have from 1 to 10 or more spaces for docking an ablation stick as a medical procedure may require more than one ablation stick to complete the procedure.

While various treatments have been described above in ablating nerves, malignant tissue, hemorrhoids and scar tissue, it should be appreciated that the method of the invention includes the treatment of any tissue in a patient's body including tissues of a sinus, a nasal passageway, an oral cavity, a blood vessel, an arteriovascular malformation, a heart, an airway, a lung, a bronchus, a bronchiole, a lung collateral ventilation pathway, a larynx, a trachea, a Eustachian tube, a uterus, a vaginal canal, cervical tissue, a fallopian tube, a liver, an esophagus, a tongue, a stomach, a duodenum, an ileum, a colon, a rectum, a bladder, a prostate, a urethra, a ureter, a vas deferens, a kidney, a gall bladder, a pancreas, a bone, an interior of a bone, a joint capsule, a tumor, a plexus of dilated veins, a fibroid, a neoplastic mass, brain tissue, skin, lymph nodes, adipose tissue, sweat glands, a keloid, scar tissue, muscle tissue, epidermal tissue, connective tissue, hyperplastic tissue, hypertrophic tissue, an ovary, a wart, a cyst, a cornea and a retina as examples.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for delivering thermal energy to a tissue, the system comprising:
   a probe having an interior chamber containing a volume of a conductive liquid;
   a first energy source configured to rapidly heat the conductive liquid to convert the conductive fluid into a subcritical conductive liquid;
   a valve in fluid communication between the interior chamber and a flow outlet, where the valve comprises a closed configuration to seal the interior chamber during heating of the conductive liquid and an open configuration that ejects the subcritical conductive liquid out of the flow outlet to the tissue; and a second energy source adapted to apply energy to the subcritical conductive liquid at the flow outlet to ionize the subcritical conductive liquid.

2. The system of claim 1, further comprising a controller configured to control operation of the first energy source.

3. The system of claim 2, wherein the controller includes an algorithm adapted to modulate the first energy source in applying energy to conductive liquid in the interior chamber to provide a pre-selected fluid temperature.

4. The system of claim 3, further comprising a temperature sensor adapted to send signals to the controller indicating the temperature of conductive liquid in the interior chamber.

5. The system of claim 2 wherein the controller is further configured to control operation of the second energy source.

6. The system of claim 1 wherein the value comprises a component that opens at a predetermined pressure in the interior chamber.

7. The system of claim 1 wherein at least one of the first and second energy sources is electrical.

8. The system of claim 7 wherein at least one of the first and second energy sources is powered by a stored energy component.

9. The system of claim 8 wherein the stored energy component is at least one of a battery and a capacitor.

10. The system of claim 9 wherein the stored energy component is carried within the elongate probe.

11. The system of claim 9 wherein the stored energy component is coupled to the elongate probe by a cable.

12. The system of claim 1 wherein the probe includes working end at the flow outlet.

13. The system of claim 1 wherein the second energy source is coupled to an electrode arrangement adapted to deliver energy to the flow proximate to the flow outlet.

14. The system of claim 1, where the volume of the interior chamber is between 0.005 ml and 5 ml.

15. The system of claim 1 wherein the controller and first energy source are adapted apply energy to the conductive liquid in the interior chamber to reach a temperature of at least 150° C.

16. The system of claim 1 wherein the controller and second energy source are adapted apply pre-determined energy to the flow about the flow outlet to ionize the flow.

* * * * *